(12) United States Patent
Anderson et al.

(10) Patent No.: US 8,105,338 B2
(45) Date of Patent: *Jan. 31, 2012

(54) STERILE SURGICAL ADAPTOR

(75) Inventors: S. Christopher Anderson, San Francisco, CA (US); Joseph P. Orban, III, Norwalk, CT (US); Bruce Michael Schena, Menlo Park, CA (US); Thomas G. Cooper, Menlo Park, CA (US); Roman L. Devengenzo, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/717,502

(22) Filed: Mar. 4, 2010

(65) Prior Publication Data

US 2010/0163057 A1  Jul. 1, 2010

Related U.S. Application Data

(63) Continuation of application No. 11/395,418, filed on Mar. 31, 2006, now Pat. No. 7,699,855, which is a continuation-in-part of application No. 11/314,040, filed on Dec. 20, 2005, now Pat. No. 7,666,191, which is a continuation-in-part of application No. 10/922,346, filed on Aug. 19, 2004, now Pat. No. 7,357,774, which is a continuation of application No. 10/004,399, filed on Oct. 30, 2001, now abandoned, which is a continuation of application No. 09/406,360, filed on Sep. 28, 1999, now Pat. No. 6,346,072, which is a continuation of application No. 08/975,617, filed on Nov. 21, 1997, now Pat. No. 6,132,368.

(60) Provisional application No. 60/033,321, filed on Dec. 12, 1996.

(51) Int. Cl.
  *A61B 19/00* (2006.01)
(52) U.S. Cl. .......................................... 606/130; 606/1
(58) Field of Classification Search .................. 600/101, 600/102, 114, 121; 606/1, 130; 128/852
See application file for complete search history.

(56) References Cited

U.S. PATENT DOCUMENTS

| | | | |
|---|---|---|---|
| 4,647,643 | A | 3/1987 | Zdrahala et al. |
| 5,018,266 | A | 5/1991 | Hutchinson et al. |
| 5,184,601 | A | 2/1993 | Putman |
| 5,413,573 | A | 5/1995 | Koivukangas |
| 5,441,042 | A | 8/1995 | Putman |
| 5,498,230 | A | 3/1996 | Adair |
| 5,631,973 | A | 5/1997 | Green |
| 5,785,643 | A | 7/1998 | Lynn |
| 5,876,328 | A | 3/1999 | Fox et al. |
| 5,931,832 | A | 8/1999 | Jensen |
| 6,102,044 | A | 8/2000 | Naidyhorski |
| 6,102,850 | A | 8/2000 | Wang et al. |

(Continued)

OTHER PUBLICATIONS

FR0611141 Preliminary Search Report Notification and Written Opinion, dated Aug. 4, 2009, 5 pages.

(Continued)

*Primary Examiner* — John P Leubecker

(57) ABSTRACT

A sterile adaptor, a sterile drape with the integrated sterile adaptor, and a telerobotic surgical system including the sterile drape with a drape interface are provided. The adaptor, drape, and system allow for draping portions of a telerobotic surgical system to maintain a sterile barrier between the sterile surgical field and the non-sterile robotic system while also providing an interface for transferring mechanical and electrical energy and signals between a robotic arm and a surgical instrument in the sterile field.

20 Claims, 43 Drawing Sheets

U.S. PATENT DOCUMENTS

| | | |
|---|---|---|
| 6,132,368 A | 10/2000 | Cooper |
| 6,331,181 B1 | 12/2001 | Tierney et al. |
| 6,346,072 B1 | 2/2002 | Cooper |
| 6,491,701 B2 | 12/2002 | Tierney et al. |
| 6,770,081 B1 | 8/2004 | Cooper et al. |
| 7,122,032 B2 | 10/2006 | Shinmura et al. |
| 7,357,774 B2 | 4/2008 | Cooper |
| 7,699,855 B2 * | 4/2010 | Anderson et al. ............. 606/130 |
| 2002/0072736 A1 | 6/2002 | Tierney et al. |
| 2002/0091374 A1 | 7/2002 | Cooper |
| 2003/0085147 A1 | 5/2003 | Gabriele |
| 2003/0153810 A1 | 8/2003 | Bertolero et al. |
| 2004/0049205 A1 | 3/2004 | Lee et al. |
| 2006/0161136 A1 | 7/2006 | Anderson et al. |
| 2006/0161138 A1 | 7/2006 | Orban et al. |
| 2007/0070157 A1 | 3/2007 | Wang |

OTHER PUBLICATIONS

PCT/US06/62364 International Search Report, mailed Jun. 12, 2006, 3 pages.

PCT/US06/62364 Written Opinion of the International Searching Authority, mailed Jun. 12, 2006, 4 pages.

U.S. Appl. No. 60/033,321, filed Dec. 12, 1996; Cooper, Thomas G.

U.S. Appl. No. 60/752,472, filed Dec. 20, 1996; Anderson, S. Christopher et al.

U.S. Appl. No. 60/752,755, filed Dec. 20, 1996; Devengenzo, Roman L. et al.

Vertut, Jean et al., "Robot Technology: Teleoperation and Robotics Evolution and Development—vol. 3A", English translation Prentice-Hall, Inc., Inglewood Cliffs, NJ; USA 1986, vol. 3A, 332 pages.

* cited by examiner

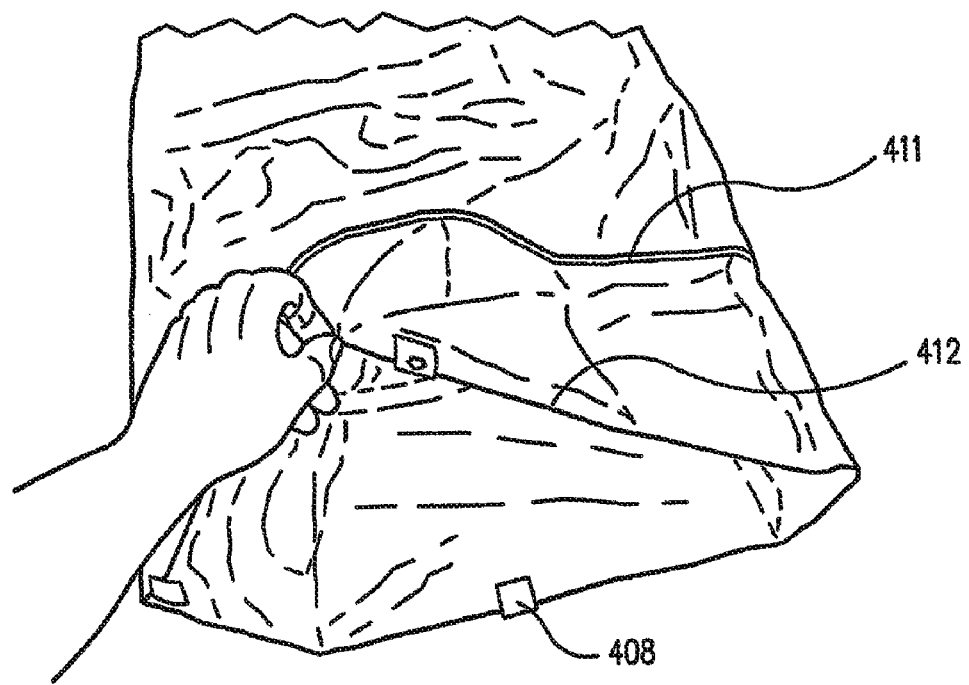
FIG. 11G1
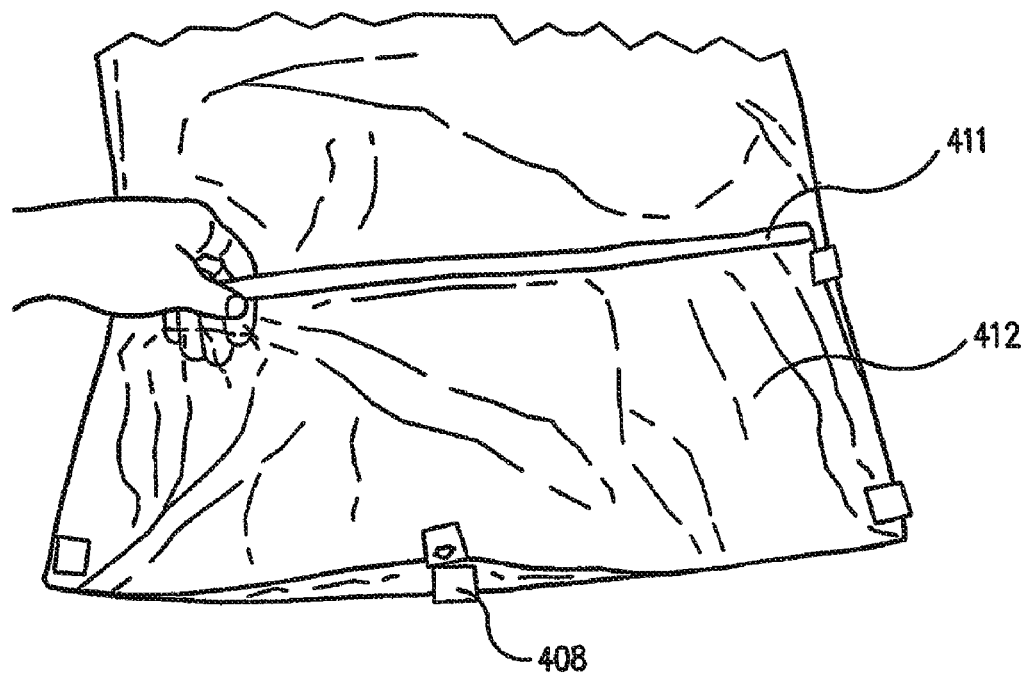
FIG. 11G2

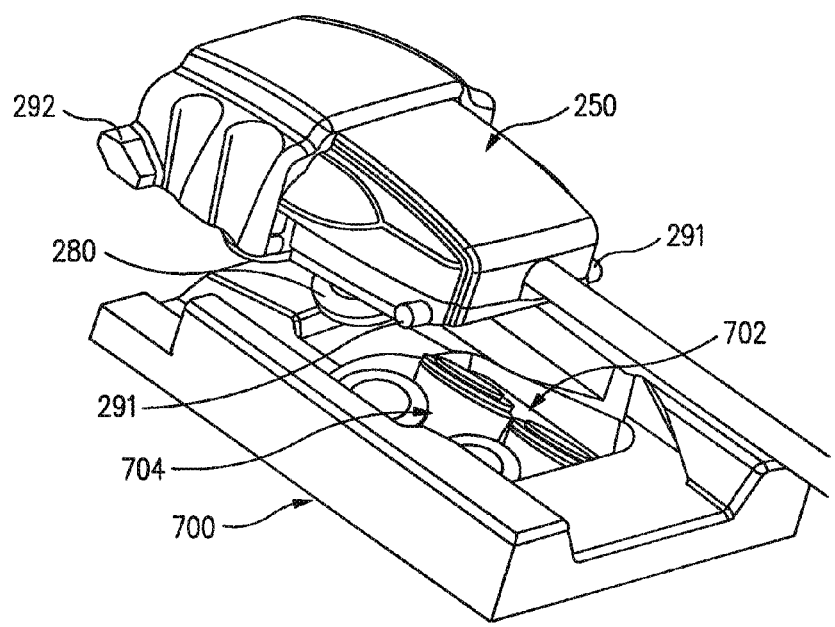
FIG. 19
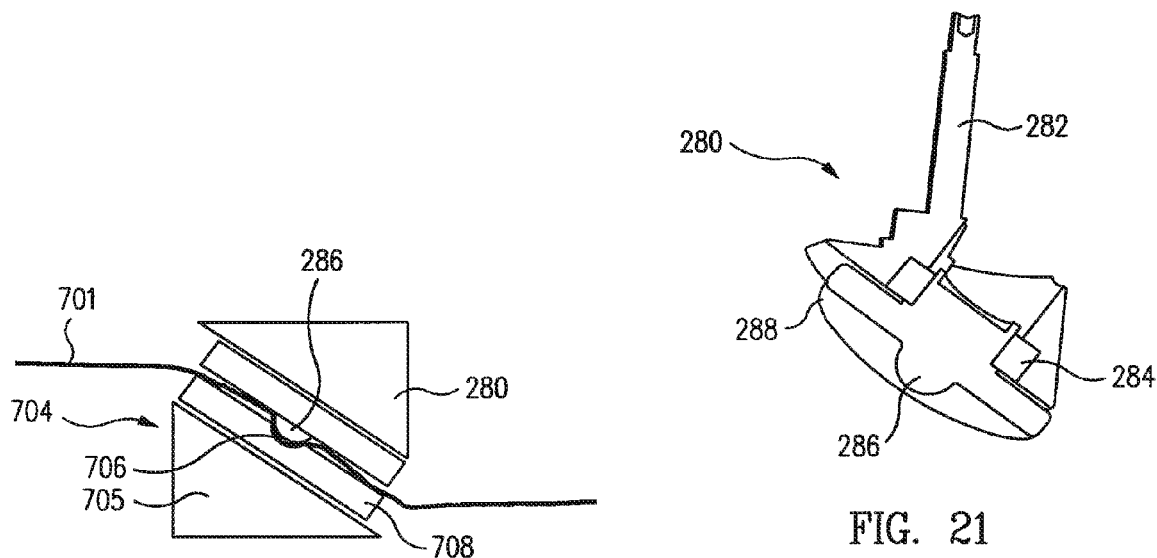
FIG. 20
FIG. 21

STERILE SURGICAL ADAPTOR

CROSS-REFERENCE TO RELATED APPLICATIONS

This application claims the benefit of U.S. Provisional Application No. 60/752,472, filed Dec. 20, 2005, the full disclosure of which is hereby incorporated by reference for all purposes.

This application is a continuation of U.S. patent application Ser. No. 11/395,418, filed Mar. 31, 2006, now U.S. Pat. No. 7,699,855, which is a continuation-in-part of U.S. patent application Ser. No. 11/314,040, filed Dec. 20, 2005, now U.S. Pat. No. 7,666,191, which is a continuation-in-part of U.S. patent application Ser. No. 10/922,346, filed Aug. 19, 2004, now U.S. Pat. No. 7,357,774, which is a continuation of U.S. patent application Ser. No. 10/004,399, filed Oct. 30, 2001, now abandoned, which is a continuation of U.S. patent application Ser. No. 09/406,360, filed Sep. 28, 1999, now U.S. Pat. No. 6,346,072, which is a continuation of U.S. patent application Ser. No. 08/975,617, filed Nov. 21, 1997, now U.S. Pat. No. 6,132,368, which claimed priority to U.S. Provisional Application No. 60/033,321, filed Dec. 12, 1996, the full disclosures of which are hereby incorporated by reference for all purposes.

This application is also a continuation-in-part of pending U.S. patent application Ser. Nos. 11/240,087 and 11/240,113, both filed Sep. 30, 2005, the full disclosures of which are hereby incorporated by reference for all purposes.

This application is related to U.S. Provisional Application No. 60/752,755, filed Dec. 20, 2005, the full disclosure of which (including all references incorporated by reference therein) is incorporated by reference herein for all purposes.

TECHNICAL FIELD

The present invention relates generally to surgical robot systems and, more particularly, to a disposable sterile adaptor of a sterile drape for covering portions of the surgical robot system.

BACKGROUND

In robotically-assisted or telerobotic surgery, the surgeon typically operates a master controller to remotely control the motion of surgical instruments at the surgical site from a location that may be remote from the patient (e.g., across the operating room, in a different room or a completely different building from the patient). The master controller usually includes one or more hand input devices, such as joysticks, exoskeletal gloves or the like, which are coupled to the surgical instruments with servo motors for articulating the instruments at the surgical site. The servo motors are typically part of an electromechanical device or surgical manipulator ("the slave") that supports and controls the surgical instruments that have been introduced directly into an open surgical site or through trocar sleeves into a body cavity, such as the patient's abdomen. During the operation, the surgical manipulator provides mechanical articulation and control of a variety of surgical instruments, such as tissue graspers, needle drivers, electrosurgical cautery probes, etc., that each perform various functions for the surgeon, e.g., holding or driving a needle, grasping a blood vessel, or dissecting, cauterizing or coagulating tissue.

This new method of performing telerobotic surgery through remote manipulation has, of course, created many new challenges. One such challenge results from the fact that a portion of the electromechanical surgical manipulator will be in direct contact with the surgical instruments, and will also be positioned adjacent the operation site. Accordingly, the surgical manipulator may become contaminated during surgery and is typically disposed of or sterilized between operations. From a cost perspective, it would be preferable to sterilize the device. However, the servo motors, sensors, encoders, and electrical connections that are necessary to robotically control the motors typically cannot be sterilized using conventional methods, e.g., steam, heat and pressure, or chemicals, because the system parts would be damaged or destroyed in the sterilization process.

A sterile drape has been previously used to cover the surgical manipulator and has included holes through which an adaptor (for example a wrist unit adaptor or a cannula adaptor) would enter the sterile field. However, this disadvantageously requires detachment and sterilization of the adaptors after each procedure and also causes a greater likelihood of contamination through the holes in the drape.

Yet another challenge with telerobotic surgery systems is that a surgeon will typically employ a large number of different surgical instruments/tools during a procedure. Since the number of manipulator arms are limited due to space constraints and cost, many of these surgical instruments will be attached and detached from the same manipulator arm a number of times during an operation. In laparoscopic procedures, for example, the number of entry ports into the patient's abdomen is generally limited during the operation because of space constraints as well as a desire to avoid unnecessary incisions in the patient. Thus, a number of different surgical instruments will typically be introduced through the same trocar sleeve during the operation. Likewise, in open surgery, there is typically not enough room around the surgical site to position more than one or two surgical manipulators, and so the surgeon's assistant will be compelled to frequently remove instruments from the manipulator arm and exchange them with other surgical tools.

What is needed, therefore, are improved telerobotic systems and methods for remotely controlling surgical instruments at a surgical site on a patient. In particular, these systems and methods should be configured to minimize the need for sterilization to improve cost efficiency while also protecting the system and the surgical patient. In addition, these systems and methods should be designed to minimize instrument exchange time and difficulty during the surgical procedure. Accordingly, a sterile adaptor and a system for robotic surgery having improved efficiency and cost-effectiveness is highly desirable.

SUMMARY

The present invention provides a sterile adaptor, a sterile drape with the integrated sterile adaptor, and a telerobotic surgical system including the sterile drape with a drape interface. The present invention allows for draping portions of a telerobotic surgical system to maintain a sterile barrier between the sterile surgical field and the non-sterile robotic system while also providing an interface for transferring mechanical and electrical energy and signals between a robotic arm and a surgical instrument in the sterile field.

In accordance with an embodiment of the present invention, an instrument sterile adaptor is provided, comprising an exterior surface for operably coupling to a sterile surgical instrument in a sterile field, an interior surface for operably coupling to a non-sterile manipulator arm of a robotic surgical system, and a drape interface for transmitting torque therethrough from the manipulator arm to the surgical instrument.

In accordance with an embodiment of the present invention, a sterile drape to cover a non-sterile portion of a robotic surgical system is provided, the sterile drape comprising an exterior surface adjacent to a sterile field for performing a surgical procedure, and an interior surface for receiving the non-sterile portion of the robotic surgical system. The sterile drape further includes a sterile adaptor for interfacing between a non-sterile manipulator arm of the robotic surgical system and a surgical instrument in the sterile field, the sterile adaptor including a drape interface for transmitting torque therethrough from the manipulator arm to the surgical instrument.

In accordance with another embodiment of the present invention, a robotic surgical system for performing a procedure within a sterile field is provided, the system comprising a manipulator arm in a non-sterile field, a surgical instrument in the sterile field, and a sterile drape covering the manipulator arm to shield the manipulator arm from the sterile field, the sterile drape including a drape interface for transmitting torque therethrough from the manipulator arm to the surgical instrument.

Advantageously, the present invention provides for improved installation and interfacing of a surgical instrument with a manipulator arm, improved robustness of the sterile field, and increased visualization of the patient by reducing the size of the drapes with more form fitting features. By providing a disposable adaptor, cost is reduced by the use of less expensive materials, while at the same time robustness and dependability of the apparatus is increased.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 11A-11L are views of a patient side manipulator (PSM) drape with integrated instrument sterile adaptor in accordance with an embodiment of the present invention.

FIG. 19 illustrates another ISA in accordance with an embodiment of the present invention.

FIG. 20 illustrates the interface of a sterile drape between an instrument input and an ISA input in accordance with this embodiment of the present invention.

FIG. 21 illustrates an instrument input in accordance with this embodiment of the present invention.

Figure 1:
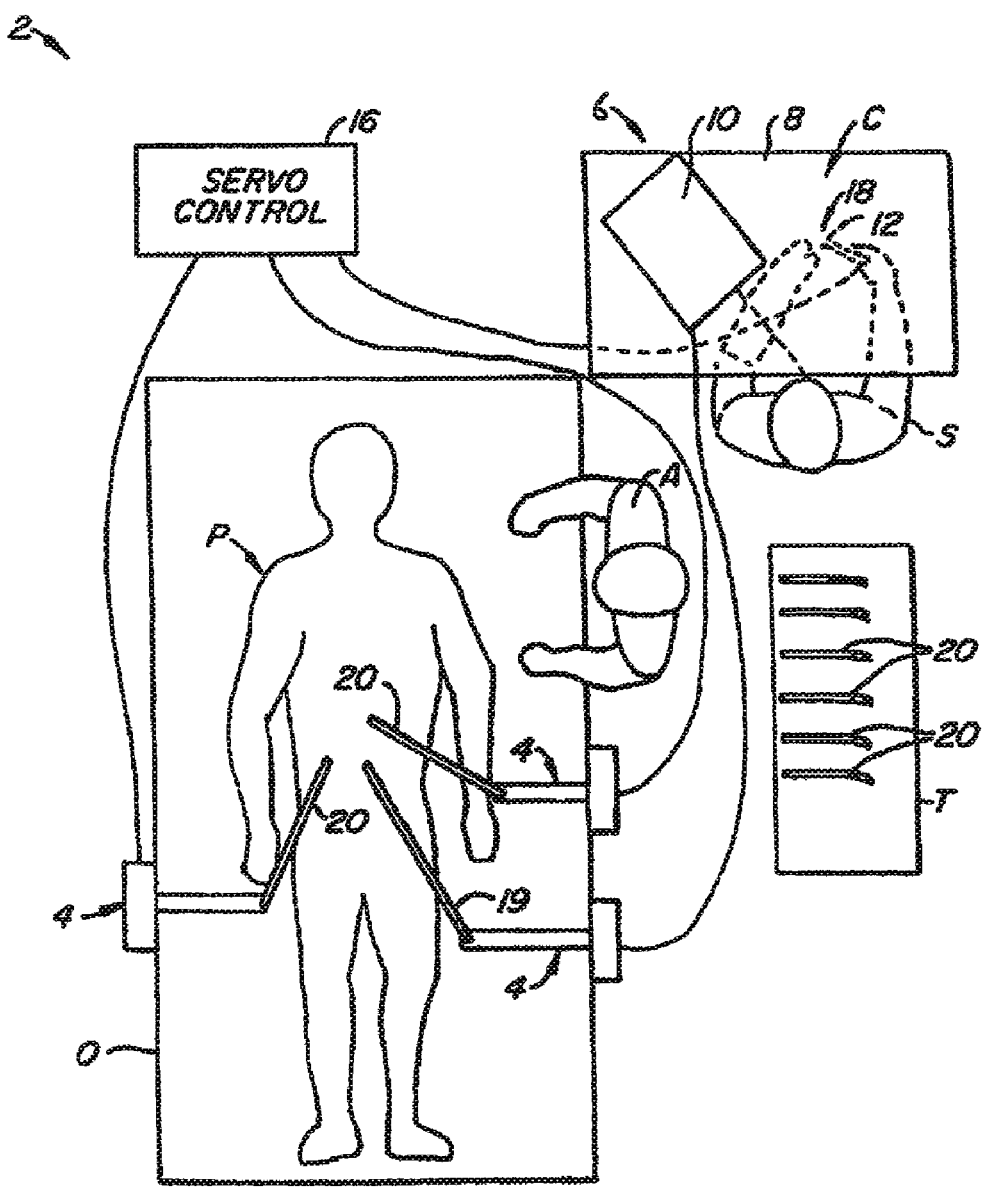
FIG. 1 is a schematic view of an operating room, illustrating a telerobotic surgical system and method in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system and method for performing robotically-assisted surgical procedures on a patient, particularly including open surgical procedures, neurosurgical procedures, such as stereotaxy, and endoscopic procedures, such as laparoscopy, arthroscopy, thoracoscopy and the like. The system and method of the present invention is particularly useful as part of a telerobotic surgical system that allows the surgeon to manipulate the surgical instruments through a servomechanism from a remote location from the patient. To that end, the manipulator apparatus or slave of the present invention will usually be driven by a kinematically-equivalent master to form a telepresence system with force reflection. A description of a suitable slave-master system can be found in U.S. patent application Ser. No. 08/517,053, filed Aug. 21, 1995, the complete disclosure of which is incorporated herein by reference for all purposes.

Referring to the drawings in detail, wherein like numerals indicate like elements, a telerobotic surgical system 2 is illustrated according to an embodiment of the present invention. As shown in FIG. 1, telerobotic system 2 generally includes one or more surgical manipulator assemblies 4 mounted to or near an operating table O, and a control assembly 6 for allowing the surgeon S to view the surgical site and to control the manipulator assemblies 4. The system 2 will also include one or more viewing scope assemblies 19 and a plurality of surgical instrument assemblies 20 adapted for being removably coupled to manipulator assemblies 4 (discussed in detail below). Telerobotic system 2 usually includes at least two manipulator assemblies 4 and preferably three manipulator assemblies 4. The exact number of manipulator assemblies 4 will depend on the surgical procedure and the space constraints within the operating room among other factors. As discussed in detail below, one of the assemblies 4 will typically operate a viewing scope assembly 19 (e.g., in endoscopic procedures) for viewing the surgical site, while the other manipulator assemblies 4 operate surgical instruments 20 for performing various procedures on the patient P.

Control assembly 6 may be located at a surgeon's console C which is usually located in the same room as operating table O so that the surgeon may speak to his/her assistant(s) A and directly monitor the operating procedure. However, it should be understood that the surgeon S can be located in a different room or a completely different building from the patient P. Control assembly 6 generally includes a support 8, a monitor 10 for displaying an image of the surgical site to the surgeon S, and one or more controller(s) 12 for controlling manipulator assemblies 4. Controller(s) 12 may include a variety of input devices, such as joysticks, gloves, trigger-guns, hand-operated controllers, voice recognition devices or the like. Preferably, controller(s) 12 will be provided with the same degrees of freedom as the associated surgical instrument assemblies 20 to provide the surgeon with telepresence, or the perception that the controller(s) 12 are integral with the instruments 20 so that the surgeon has a strong sense of directly controlling instruments 20. Position, force, and tactile feedback sensors (not shown) may also be employed on instrument assemblies 20 to transmit position, force, and tactile sensations from the surgical instrument back to the surgeon's hands as he/she operates the telerobotic system. One suitable system and method for providing telepresence to the operator is described in U.S. patent application Ser. No. 08/517,053, filed Aug. 21, 1995, which has previously been incorporated herein by reference.

Monitor 10 will be suitably coupled to the viewing scope assembly 19 such that an image of the surgical site is provided adjacent the surgeon's hands on surgeon console C. Preferably, monitor 10 will display an inverted image on a display 18 that is oriented so that the surgeon feels that he or she is actually looking directly down onto the operating site. To that end, an image of the surgical instruments 20 appears to be located substantially where the operator's hands are located even though the observation points (i.e., the endoscope or viewing camera) may not be from the point of view of the image. In addition, the real-time image is preferably transformed into a perspective image such that the operator can manipulate the end effector and the hand control as if viewing the workspace in substantially true presence. By true presence, it is meant that the presentation of an image is a true perspective image simulating the viewpoint of an operator that is physically manipulating the surgical instruments 20. Thus, a controller (not shown) transforms the coordinates of the surgical instruments 20 to a perceived position so that the perspective image is the image that one would see if the camera or endoscope was located directly behind the surgical instruments 20. A suitable coordinate transformation system for providing this virtual image is described in U.S. patent application Ser. No. 08/239,086, filed May 5, 1994, now U.S. Pat. No. 5,631,973, the complete disclosure of which is incorporated herein by reference for all purposes.

As shown in FIG. 1, a servomechanism 16 is provided for transferring the mechanical motion of controllers 12 to manipulator assemblies 4. Servomechanism 16 may be separate from, or integral with manipulator assemblies 4. Servomechanism 16 will usually provide force and torque feedback from the surgical instruments 20 to the hand-operated controllers 12. In addition, servomechanism 16 will include a safety monitoring controller (not shown) that may freeze or at least inhibit all robot motion in response to recognized conditions (e.g., exertion of excessive force on the patient, "running away" of the manipulator assemblies 4, etc.). The servomechanism preferably has a servo bandwidth with a 3 dB cut off frequency of at least 10 hz so that the system can quickly and accurately respond to the rapid hand motions used by the surgeon. To operate effectively with this system, manipulator assemblies 4 have a relatively low inertia and the drive motors 170 (see FIG. 8) have relatively low ratio gear or pulley couplings. Any suitable conventional or specialized servomechanism may be used in the practice of the present invention, with those incorporating force and torque feedback being particularly preferred for telepresence operation of the system.

Figure 7:
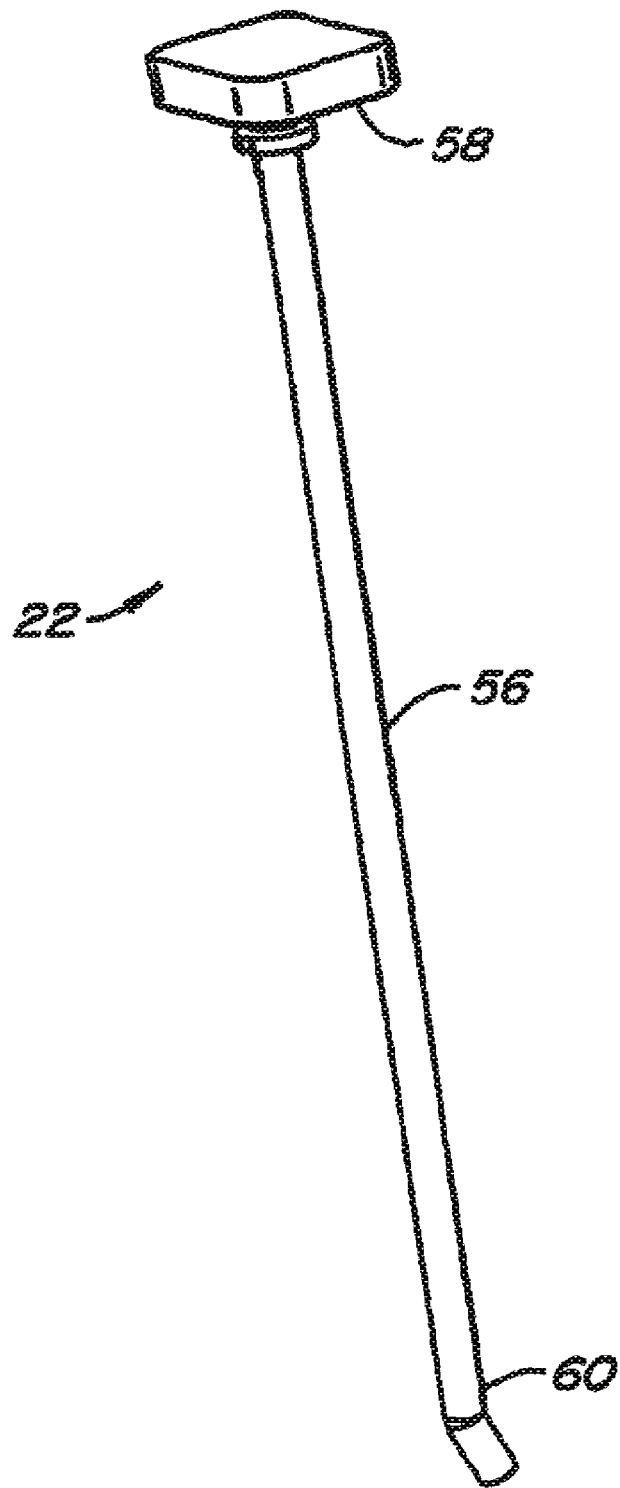
FIG. 7 is a perspective view of the wrist unit in accordance with an embodiment of the present invention.

Referring to FIG. 7, surgical instrument assemblies 20 each include a wrist unit 22 and a surgical tool 24 (FIGS. 3A and 3B) removably attached to wrist unit 22. As discussed in detail below, each wrist unit 22 generally includes an elongate shaft 56 having a proximal cap 58 and a distal wrist 60 pivotally coupled to surgical tool 24. Each wrist unit 22 is substantially the same, and will have different or the same surgical tools 24 attached thereto, depending on the requirements of the surgical procedure. Alternatively, wrist units 22 may have specialized wrists 60 designed for individual surgical tools 24 so that the wrist units 22 may be used with conventional tools 24. As shown in FIG. 1, the instrument assemblies 20 are usually assembled onto a table T or other suitable support adjacent the operating table O. According to a method of the present invention (described below), wrist units 22 and their associated surgical tools 24 can be quickly exchanged during the surgical procedure by coupling and decoupling wrist unit shafts 56 from manipulator assemblies 4.

Figure 2:
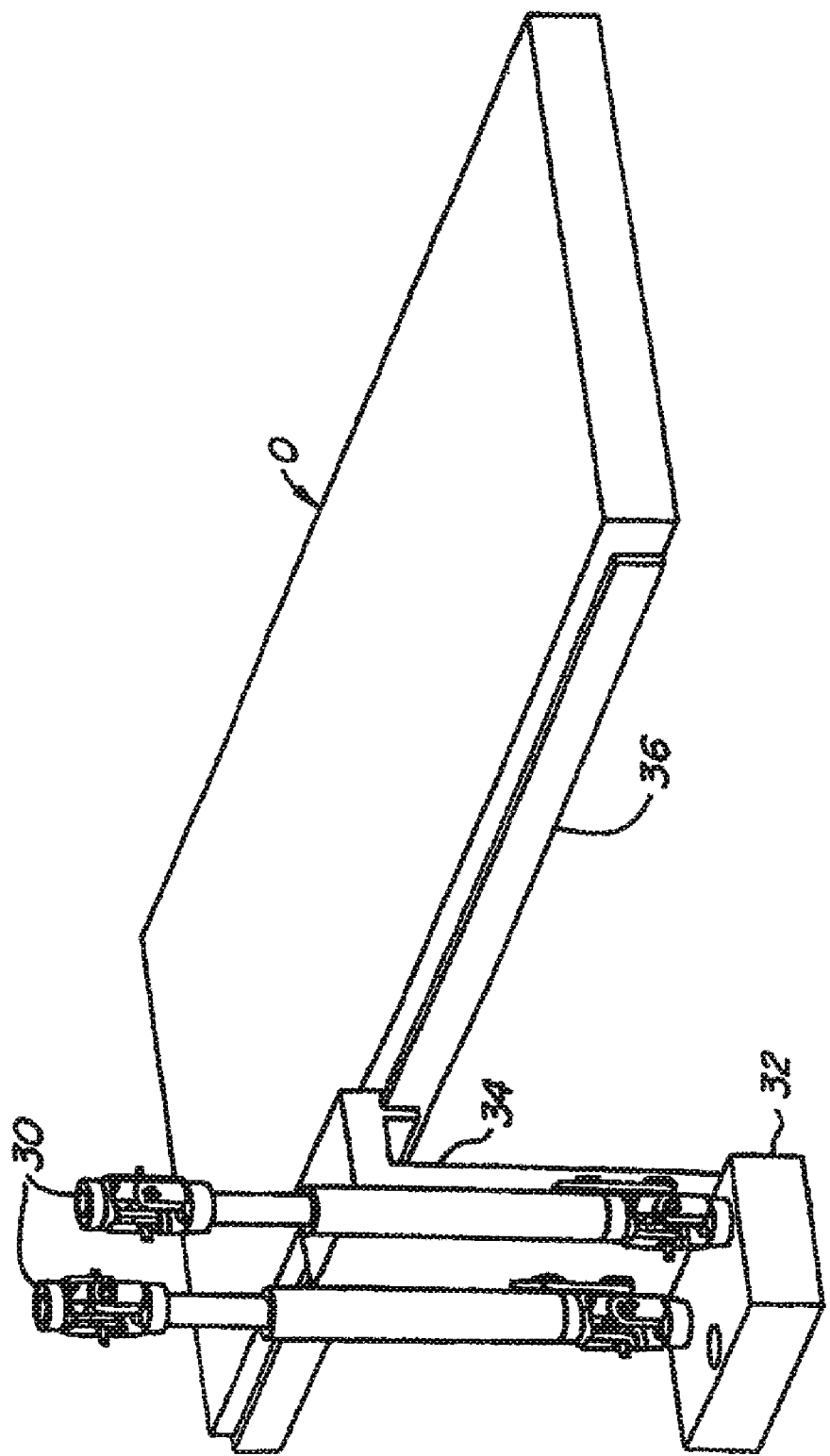
FIG. 2 is an enlarged view of the operating room of FIG. 1 illustrating a pair of mounting joints coupled to an operating table according to the present invention.

Referring to FIG. 2, each manipulator assembly 4 is preferably mounted to operating table O by a mounting joint 30. Mounting joints 30 provide a number of degrees of freedom (preferably at least 5) to assemblies 4, and they include a brake (not shown) so that assemblies 4 can be fixed at a suitable position and orientation relative to the patient. Joints 30 are mounted to a receptacle 32 for mounting joints 30 to operating table O, and for connecting each manipulator assembly 4 to servomechanism 16. In addition, receptacle 32 may connect joints 30 to other systems, such as an RF electrical power source, a suction-irrigation system, etc. Receptacle 32 includes a mounting arm 34 that is slidably disposed along an outer rail 36 of operating table O. Manipulator assemblies 4 may also be positioned over the operating table O with other mechanisms. For example, the system may incorporate a support system (coupled to the ceiling or a wall of the operating room) that moves and holds one or more manipulator assemblies 4 over the patient.

Referring now to FIGS. 3-8, manipulator assembly 4 will be described in further detail. Manipulator assembly 4 is a three-component apparatus that includes a non-sterile drive and control component, a sterilizable end effector or surgical tool (i.e., surgical instrument assembly 20), and an intermediate connector component. The intermediate connector includes mechanical elements for coupling the surgical tool 24 with the drive and control component, and for transferring motion from the drive component to the surgical tool 24. As shown in FIG. 3B, the drive and control component generally includes a drive assembly 40 and a multiple degree of freedom robotic arm 42 coupled to a mounting bracket 44, which is adapted for mounting onto mounting joints 30 (FIG. 2). Preferably, drive assembly 40 and robotic arm 42 are pivotally coupled to bracket 44 about an X-axis, which extends through a remote center of spherical rotation 45 (see FIG. 8, discussed in further detail below). Manipulator assembly 4 further includes a forearm assembly 46 fixed to a distal end 48 of arm 42, and a wrist unit adaptor 52 coupled to forearm assembly 46 for mounting wrist unit 22 and surgical tool 24 to manipulator assembly 4.

For endoscopic procedures, manipulator assembly 4 additionally includes a cannula adaptor 64 attached to a lower portion of forearm 46 for mounting a cannula 66 to manipulator assembly 4. Alternatively, cannula 66 may be an integral cannula (not shown) that is built into forearm assembly 46 (i.e., non-removable). Cannula 66 may include a force sensing element (not shown), such as a strain gauge or force-sensing resistor, mounted to an annular bearing within cannula 66. The force sensing bearing supports surgical tool 24 during surgery, allowing the tool to rotate and move axially through the central bore of the bearing. In addition, the bearing transmits lateral forces exerted by the surgical tool 24 to the force sensing element, which is connected to servomechanism 16 for transmitting these forces to controller(s) 12. In this manner, forces acting on surgical tools 24 can be detected without disturbances from forces acting on cannula 66, such as the tissue surrounding the surgical incision, or by gravity and inertial forces acting on manipulator assembly 4. This facilitates the use of manipulator assembly 4 in a robotic system because the surgeon will directly sense the forces acting against the surgical tool 24.

Figure 3A:
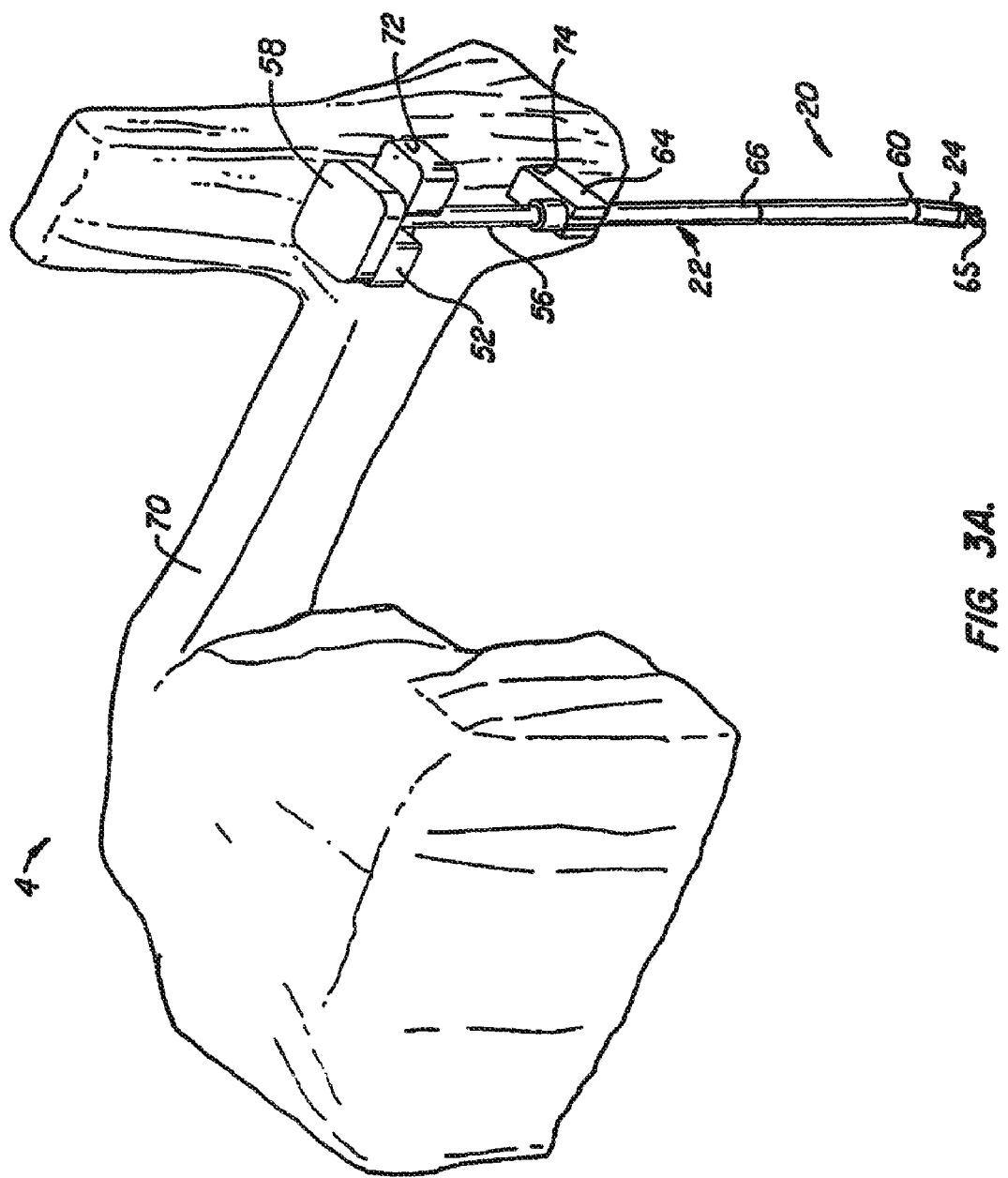
FIG. 3A is a perspective view of a robotic surgical manipulator that is partially covered by a sterile drape in accordance with an embodiment of the present invention.

As shown in FIG. 3A, manipulator assembly 4 further includes a sterile drape 70 sized to cover substantially the entire manipulator assembly 4. Drape 70 has a pair of holes 72, 74 sized and arranged so that wrist unit adaptor 52 and cannula adaptor 64 may extend through holes 72, 74 to mount wrist unit 22 and cannula 66 to manipulator assembly 4. Sterile drape 70 comprises a material configured to effectively shield manipulator assembly 4 from the surgical site so that most of the components of assembly 4 (i.e., arm 42, drive assembly 40 and forearm assembly 46) do not have to be sterilized prior to, or following the surgical procedure.

As shown in FIG. 3A, wrist unit adaptor 52 and cannula adaptor 64 extend through holes 72, 74 of drape 70 so that forearm assembly 46 and the remainder of manipulator assembly 4 remain shielded from the patient during the procedure. In one embodiment, wrist unit adaptor 52 and cannula adaptor 64 are manufactured as reusable components that will be sterilized because these components extend into the sterile field of the surgical site. Wrist unit and cannula adapters 52, 64 may be sterilized by normal methods, i.e., steam, heat and pressure, chemicals and the like. Referring again to FIG. 3B, wrist unit adaptor 52 includes an opening 80 for receiving shaft 56 of wrist unit 22. As discussed in detail below, shaft 56 can be laterally urged through opening 80 and snap-fit into adaptor 52 such that the non-exposed portion of wrist unit adaptor 52 remains sterile (i.e., remains on the sterile side of drape 70 opposite the sterile field). Wrist unit adaptor 52 may also include a latch (not shown) for securing wrist unit 22 therein. Similarly, cannula adaptor 64 includes an opening 82 for snap fitting cannula 66 thereto such that the non-exposed portion of adaptor 64 remains sterile during the surgical procedure.

Figure 4:
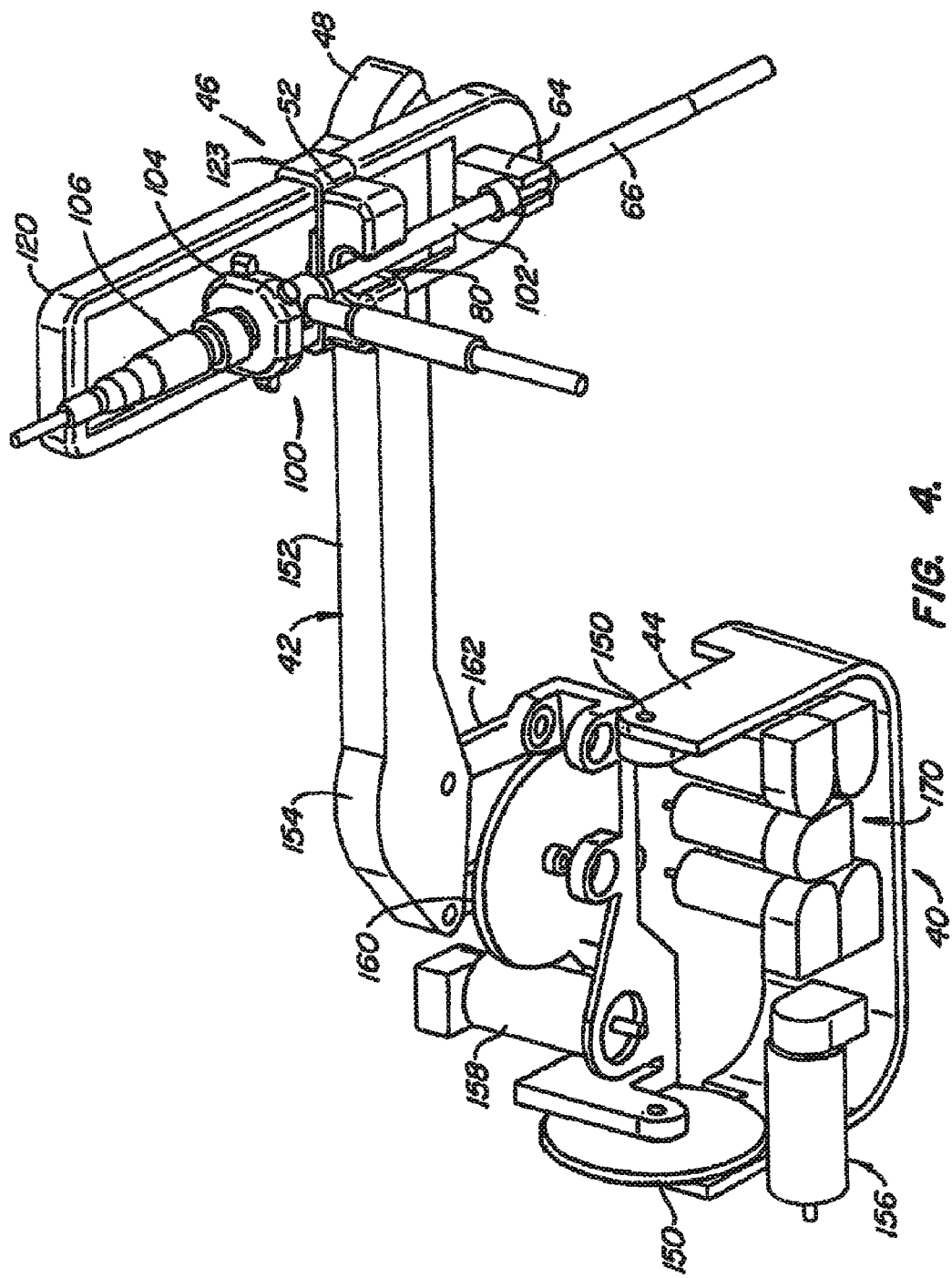
FIG. 4 illustrates the robotic surgical manipulator of FIGS. 3A-3B incorporating a camera and endoscope for viewing the surgical site.

As shown in FIG. 4, wrist unit adaptor 52 may also be configured to receive a viewing scope 100 for viewing the surgical site. For endoscopic procedures, viewing scope 100 can be a conventional endoscope, which typically includes a rigid, elongated tube 102 containing a lens system (not shown) and a camera mount 104 at the proximal end of the tube 102. A small video camera 106 is preferably attached to the camera mount 104 and connected to video monitor 10 to provide a video image of the procedure. Preferably, the scope 100 has a distal end (not shown) configured to allow lateral or angled viewing relative to tube 102. The viewing scope may also have a guidable tip that can be deflected or rotated by manipulating an actuator on a proximal end of tube 102. This type of scope is commercially available from Baxter Healthcare Corp. of Deerfield, Ill., or Origin Medsystems, Inc. of Menlo Park, Calif.

As shown in FIG. 4, viewing scope 100 further includes a scope adaptor 110 for coupling viewing scope 100 to wrist unit adaptor 52. Scope adaptor 110 is sterilizable, ETO and autoclavable, and it includes a plurality of motion feedthroughs (not shown) for transferring motion from drive assembly 40 to scope 100. In the preferred configuration, the motion includes pitch and yaw motion, rotation about the Z-axis, and movement along the Z-axis.

Figure 5:
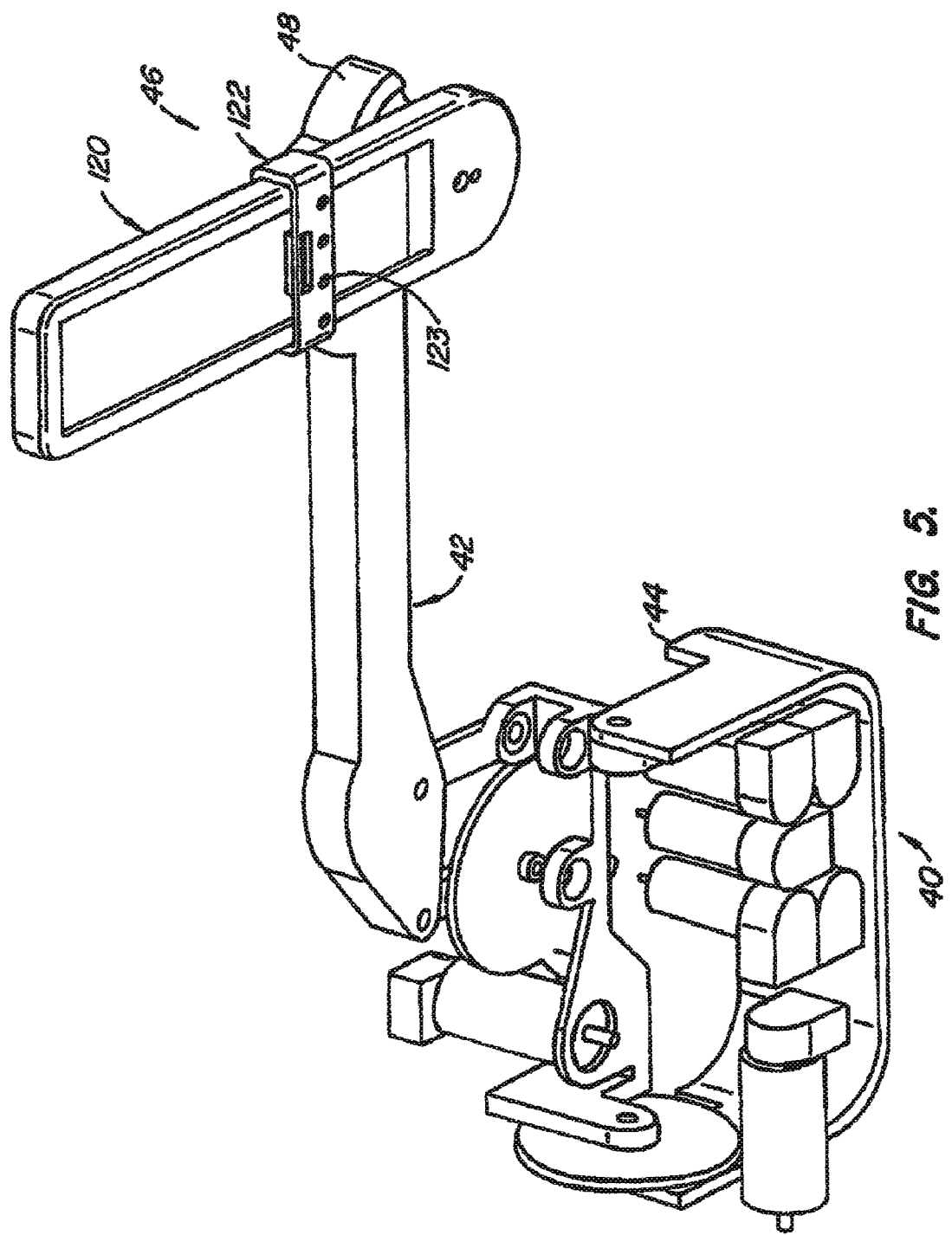
FIG. 5 is a partial view of the robotic manipulator of FIGS. 3A-3B, illustrating mechanical and electrical couplings between the arm and the wrist unit.
Figure 6:
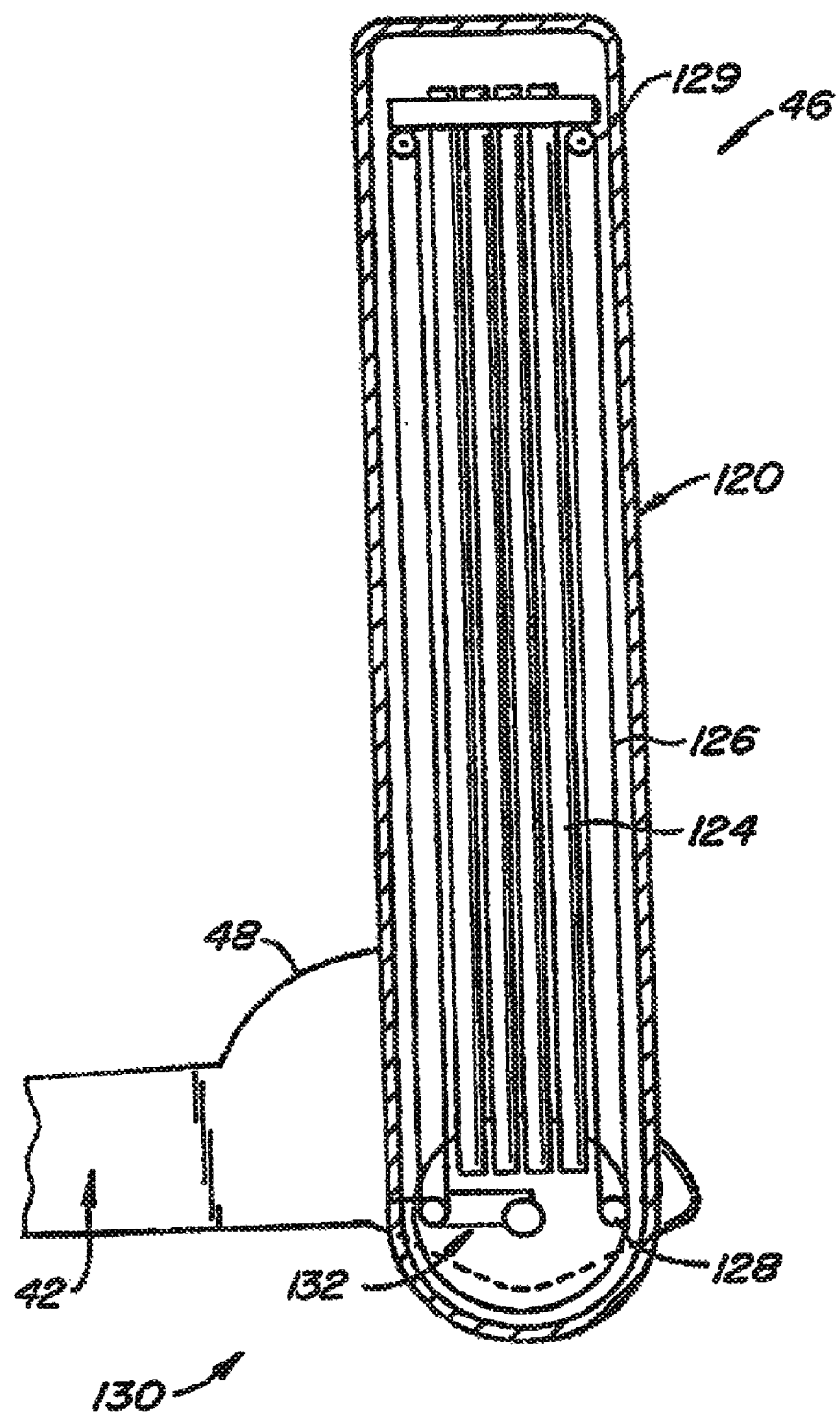
FIG. 6 is a partially cut-away sectional view of a forearm and a carriage of the manipulator of FIGS. 3A and 3B.

Referring now to FIGS. 5 and 6, forearm assembly 46 will be described in further detail. As shown in FIG. 5, forearm assembly 46 includes a housing 120 fixed to arm 42 and a movable carriage 122 slidably coupled to housing 120. Carriage 122 slidably mounts wrist unit adaptor 52 to housing 120 for moving wrist unit adaptor 52 and wrist unit 20 in the Z-direction. In addition, carriage 122 defines a number of openings 123 for transferring motion and electrical signals from forearm assembly 46 to wrist unit adaptor 52. As shown in FIG. 6, a plurality of rotatable shafts 124 are mounted within housing 120 for transferring motion from arm 42 through openings 123 to wrist unit adaptor 52 and wrist unit 22. Rotating shafts 124 preferably provide at least four degrees of freedom to wrist unit 22, including yaw and pitch motion of surgical tool 24 about wrist 60 of wrist unit 22, rotation of wrist unit 22 about the Z-axis and actuation of tool 24. The system may also be configured to provide more or less degrees of freedom, if desired. Actuation of tool 24 may include a variety of motions, such as opening and closing jaws, graspers or scissors, applying clips or staples and the like. Motion of wrist unit 22 and tool 24 in the Z direction is provided by a pair of carriage cable drives 126 extending between rotatable pulleys 128, 129 on either end of forearm housing 120. Cable drives 126 function to move carriage 122 and wrist unit 22 in the Z direction relative to forearm housing 120.

As shown in FIG. 6, distal end 48 of arm 42 includes a coupling assembly 130 having a plurality of motion feed-throughs 132 for transferring motion from arm 42 to forearm assembly 46. In addition, coupling assembly 130 includes a number of electrical connectors (not shown) for transferring electrical signals from arm 42 to wrist unit 22. Similarly, wrist unit adaptor 52 includes a plurality of motion feed-throughs (not shown) and electrical connections (not shown) for transferring motion, and for sending and receiving electrical signals to and from wrist unit 22 (e.g., for sending and receiving force and torque feedback signals from the surgical site to controllers 12). The components on either side of coupling assembly 130 and wrist unit adaptor 52 have a finite range of motion. Usually, this range of motion will be at least 1 revolution and preferably greater than 1 revolution. These ranges of motion are aligned with each other when the forearm assembly 46 is mechanically coupled to the coupling assembly 130 and when wrist unit adaptor 52 is mechanically coupled to the forearm 46.

Referring to FIG. 7, wrist unit 22 will now be described in further detail. As shown, wrist unit 22 includes a hollow shaft 56 having a cap 58 attached to its proximal end and a wrist 60 attached to its distal end. Wrist 60 includes a coupling (not shown) for removably coupling a variety of surgical tools 24 to shaft 56. Shaft 56 is rotatably coupled to cap 58 for providing rotation of shaft 56 and tool 24 about the longitudinal axis of shaft 56 (i.e., the Z axis). Cap 58 houses a mechanism (not shown) for transferring motion from wrist unit adaptor 52 to drive cables (not shown) within shaft 56. The drive cables are suitably coupled to drive pulleys within shaft 56 to pivot tool 24 about wrist 60, and to actuate end effectors 140 on tool 24. Wrist 60 may also be operated by other mechanisms, such as differential gears, push-rods, or the like.

Tool 24 is removably coupled to wrist 60 of wrist unit 22. Tool 24 will preferably include an end effector 65 (FIGS. 3A and 3B) having a tactile sensor array (not shown) for providing tactile feedback to the surgeon. Tool 24 may include a variety of articulated tools, such as jaws, scissors, graspers, needle holders, micro dissectors, staple appliers, tackers, suction irrigation tools, clip appliers, that have end effectors driven by wire links, eccentric cams, push-rods or other mechanisms. In addition, tool 24 may comprise a non-articulated instrument, such as cutting blades, probes, irrigators, catheters or suction orifices. Alternatively, tool 24 may comprise an electrosurgical probe for ablating, resecting, cutting or coagulating tissue. In the latter embodiment, wrist unit 22 will include a conductive element, such as a proximal banana plug coupled to a lead wire or rod extending through shaft 56 to tool 24.

Figure 8:
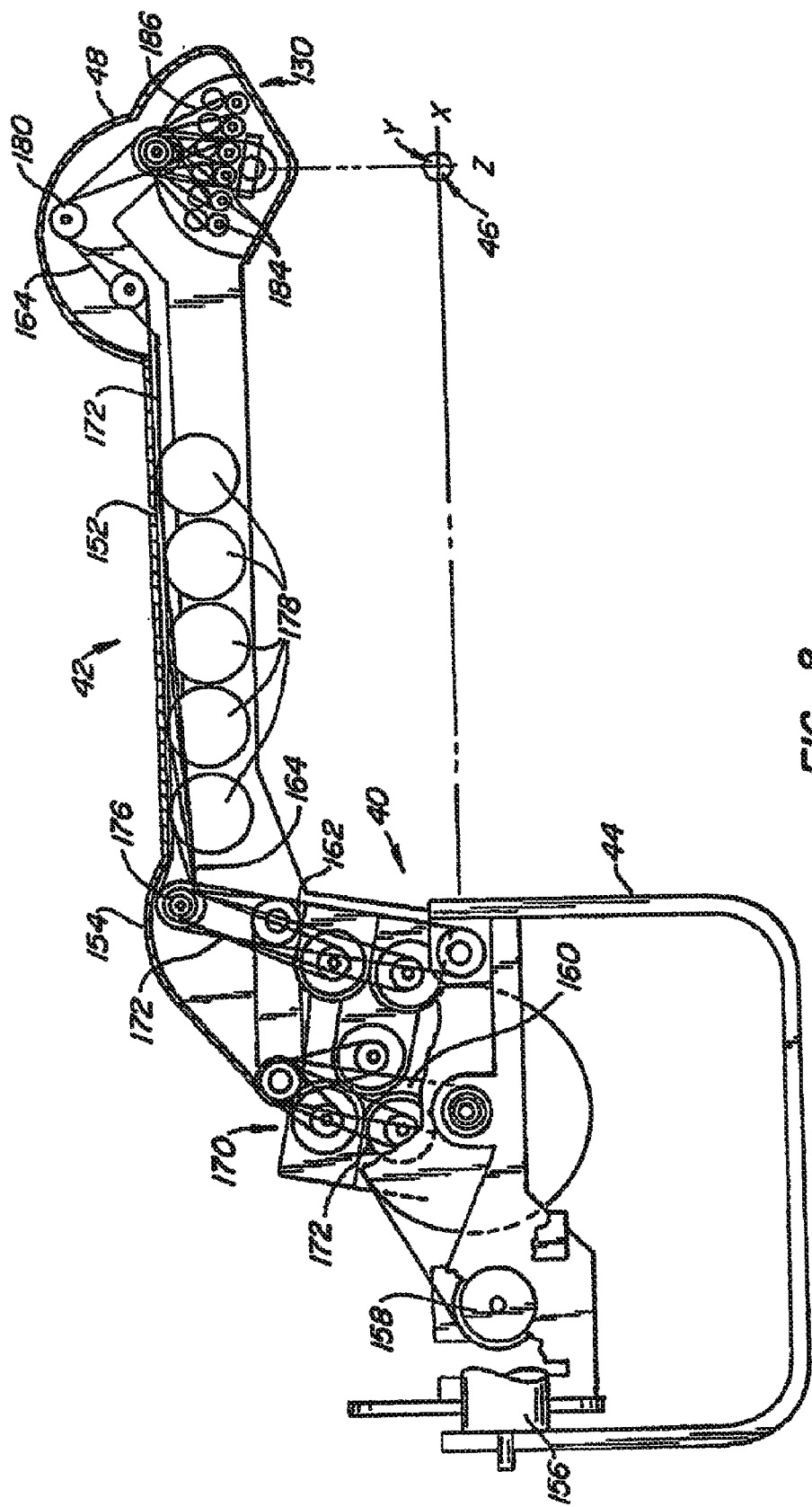
FIG. 8 is a side cross-sectional view of a portion of the robotic manipulator, illustrating the arm and the drive assembly.

Referring to FIGS. 4 and 8, a specific configuration of the drive and control component of the present invention (i.e., the robotic arm 42 and drive assembly 40) will be described in further detail. As discussed above, arm 42 and drive assembly 40 are rotatably coupled about a pair of pins 150 extending from mounting bracket 44. Arm 42 preferably comprises an elongate, substantially rigid body 152 with a distal end 48 coupled to forearm assembly 48 and a proximal end 154 pivotally coupled to drive assembly 40 and bracket 44 for rotation about pitch and yaw or the X and Y axes (note that the Y axis is perpendicular to the page and extends through point 45, see FIG. 8). Arm 40 may have other configurations, such as an elbow arm (similar to the human arm), prismatic arm (straight extendable) or the like. A stationary yaw motor 156 is mounted to mounting bracket 44 for rotating arm 42 and drive assembly 40 about the X-axis. Drive assembly 40 also includes a pitch motor 158 coupled to arm 42 for rotating arm about the Y axis. A pair of substantially rigid linkage elements 160, 124 extend from bracket 44 to robotic arm 42 to pivotally couple arm 42 to bracket 44 about Y-axis. One of the linkage elements 160 is pivotally coupled to arm 42, and the other linkage element 124 is pivotally coupled to a third linkage element 164 extending parallel to arm 42. Preferably, robotic arm 42 is a channel shaped rigid element that at least partially houses the third linkage element 164. The linkage elements 160, 124 and 164 and arm 42 form a parallelogram linkage in which the members are connected together in a parallelogram for relative movement only in the plane formed by the members.

The Z-axis of wrist unit 22 held at the distal end 48 of arm 42 intersects the x axis of the parallelogram linkage described above. Wrist unit 22 has a remote center of spherical rotation about the position indicated by the numeral 45 in FIG. 8. Thus, the distal end of wrist unit 22 can be rotated about its own axis or the X and Y axes while the remote center of rotation 45 remains at the same location. A more complete description of a remote center positioning device can be found in U.S. patent application Ser. No. 08/504,301, filed Jul. 20, 1995, now U.S. Pat. No. 5,931,832, the complete disclosure of which is incorporated herein by reference for all purposes. It should be noted that arm 42 and drive assembly 40 may be used with a broad range of positioning devices other than that described above and shown in FIG. 8, such as a stereotaxic positioner, a fixed gimbal, or the like.

Referring again to FIG. 8, drive assembly 40 further includes a plurality of drive motors 170 coupled to arm 42 for rotation therewith. Pitch and yaw motors 156, 158 control the motion of arm 42 (and drive motors 170) about the X and Y axes and drive motors 170 control the motion of wrist unit 22 and surgical tool 24. Preferably, at least five drive motors 170 are coupled to arm 42 for providing at least five degrees of freedom to wrist unit 22. Drive motors 170 will preferably include encoders (not shown) for responding to servomechanism 16 and force sensors (not shown) for transmitting force and torque feedback to the surgeon S. As discussed above, the five degrees of freedom preferably include movement of carriage 122 and wrist unit 22 in the Z-direction, rotation of wrist unit 22 about the Z-axis, pitch and yaw rotation of surgical tool 24 around wrist 60 and actuation of tool 24.

As shown, cables 172 extend from each motor 170 around a motor drive pulley 174, an idler pulley 176 within arm 42 and along a relatively large pot capstan 178 to minimize the effect of friction torque on cables 172. The cables 172 each extend around another idler pulley 180 at distal end 48 of arm 42, around a coupling drive pulley 182 and back to the motor 170. The cables 172 will preferably be tensioned at the motor drive pulley 174 and anchored there as well as at the coupling drive pulley 182. As shown in FIG. 8, coupling drive pulley 182 is connected to a plurality of smaller pulleys 184 within coupling assembly 130 via a plurality of cables 186 for transferring motion from the motors 170 to wrist unit adaptor 52.

A method for performing a surgical procedure on a patient according to the present invention will now be described with reference to FIGS. 1-8. As shown in FIG. 2, mounting joints 30 are attached to receptacle 32, which is attached to the operating table O by sliding mounting arm 34 along rail 36. Each manipulator assembly 4 is then attached to its respective mounting joint 30 and articulated into the proper position and orientation relative to the patient P. Receptacles 32 are then coupled to servomechanism 16 and other systems that may be required during the surgical procedure, such as an RF power supply, a suction/irrigation system, etc. Sterile drapes 70 are placed over the manipulator assemblies 4 before, during, or after the patient has been anesthetized (FIG. 3A). To prepare for the surgical procedure, manipulator assemblies 4 may or may not be chemically cleaned prior to covering them with drapes 70. Wrist unit adapters 52, cannula adapters 64, and scope adapters 110 are snapped onto forearm assemblies 46 of manipulator assemblies 4 (see FIGS. 3B and 5). The number and relative positions of scope adapters 110 and wrist unit adapters 52 will, of course, depend on the individual surgical procedure (e.g., cannula adapters 64 may not be required for open surgical procedures).

During the surgical procedure, surgical instrument assemblies 20 are coupled to their respective manipulator assemblies 4 by laterally urging each respective wrist unit shaft 56 through opening 80 of wrist unit adaptor 52. Each wrist unit 22 will have suitable identification means (not shown) to quickly and easily indicate what type of tool 24 is connected to the wrist unit 22. When the surgeon wishes to change surgical tools 24, he or she manipulates controller(s) 12 so that carriage 122 moves to a top or proximal position of travel along forearm assembly 46 (see FIG. 3B). In this position, surgical tool 24 is within cannula 66 or during open procedures, removed from the surgical site. The assistant(s) A then pulls upward on wrist cap 58 to release the latch (not shown), thereby allowing wrist unit 22 to slide further upwards and out of cannula 66. The assistant(s) A may then pull wrist unit 22 laterally to decouple it from wrist unit adaptor 52. When wrist unit 22 is no longer coupled to adaptor 52, the control mechanism understands that the system is in "tool change mode", and drives carriage 122 to the proximal position if it has not already been moved there by the surgeon.

Figure 3B:
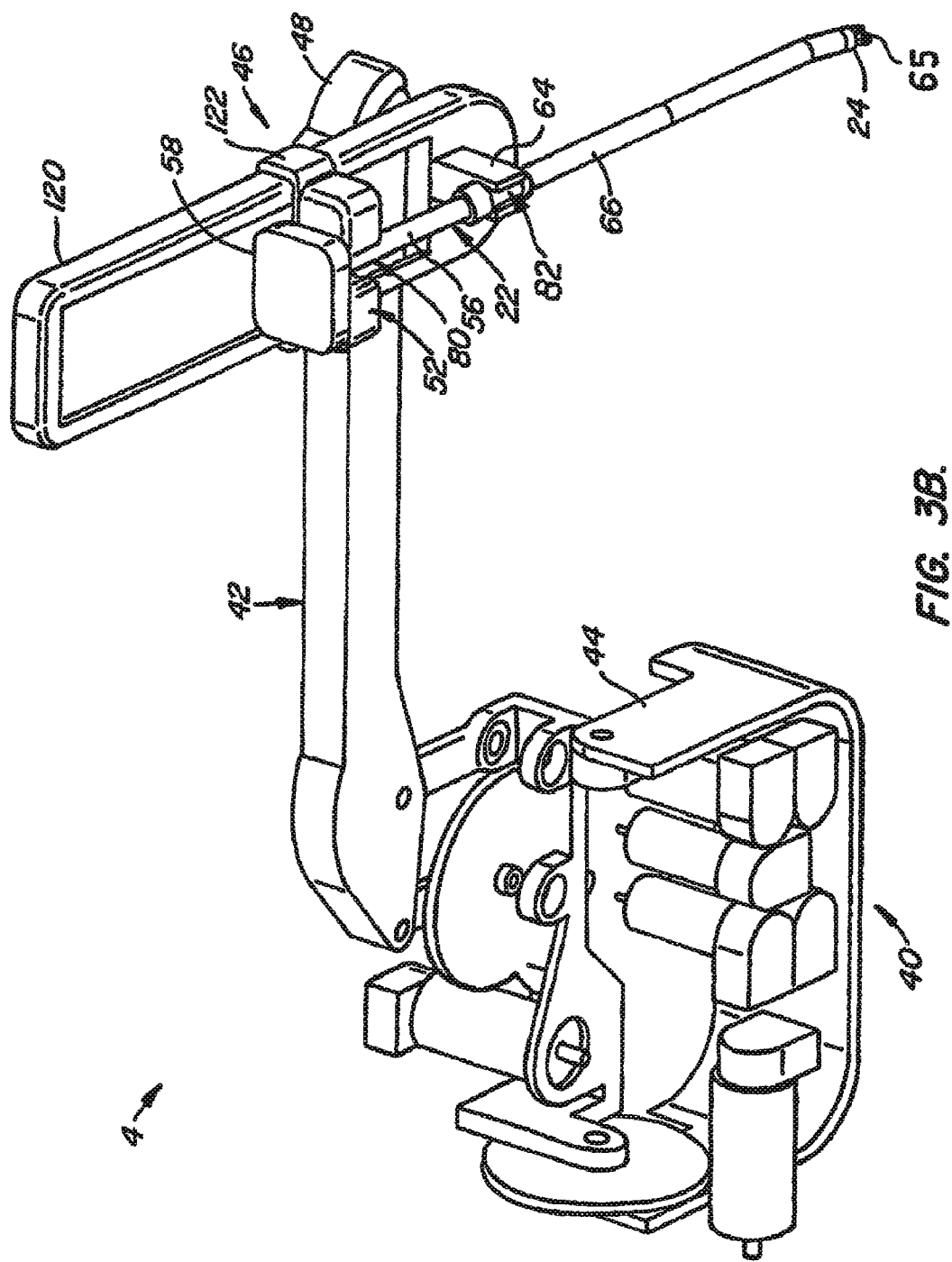
FIG. 3B is a perspective view of the robotic surgical manipulator of FIG. 3A without the sterile drape to illustrate a multiple degree of freedom arm coupling a driving assembly with a wrist unit and a surgical tool.

To couple another surgical instrument assembly 20 to manipulator assembly 4, the assistant(s) A grabs another assembly 20 from table T, laterally urges wrist unit shaft 56 into opening 80 of wrist unit adaptor 52, and then moves wrist unit 22 downward so that surgical tool 24 resides within cannula 66 (see FIGS. 1 and 3B). This downward movement of wrist unit 22 automatically mates the electrical couplings and motion feed-throughs (not shown) within wrist cap 58 and wrist unit adaptor 52. The system may include a control mechanism configured to lock carriage 122 travel at the top or proximal position, e.g., by actuating a brake (not shown), until the couplings are mated and wrist unit 22 is no longer being moved downward. At this point, the surgeon S may continue the surgical procedure.

The system and method of the present invention preferably includes a mechanism for counting the number of times wrist unit 22 is decoupled and coupled from wrist unit adaptor 52. In this manner, the manufacturer may limit the number of times wrist unit 22 can be used. In a specific configuration, an integrated circuit chip (not shown) is housed within wrist cap 58. The circuit chip counts the number of times wrist unit 22 is coupled to wrist unit adaptor 52, e.g., 20 times, and a warning shows up on the surgeon's console C. The control system then downgrades the performance of the system by reducing the load it can deliver or increasing apparent backlash.

Referring now to FIGS. 9A-9B and 10A-10B, a robotic surgical system 200 including a robotic surgical manipulator 204 that is fully covered by a sterile drape 270 is shown in accordance with another embodiment of the present invention. The present invention provides a sterile adaptor integrated with a sterile drape for draping portions of a telerobotic surgical system to maintain a sterile barrier between the sterile surgical field and the non-sterile robotic system while also providing an interface for transferring mechanical and electrical energy and signals between a surgical instrument and the robotic system. Advantageously, the present invention allows a user to repeatedly and easily install and remove surgical instruments on the system while maintaining a sterile barrier between the sterile surgical instrument and the non-sterile robotic system.

Figure 9A:
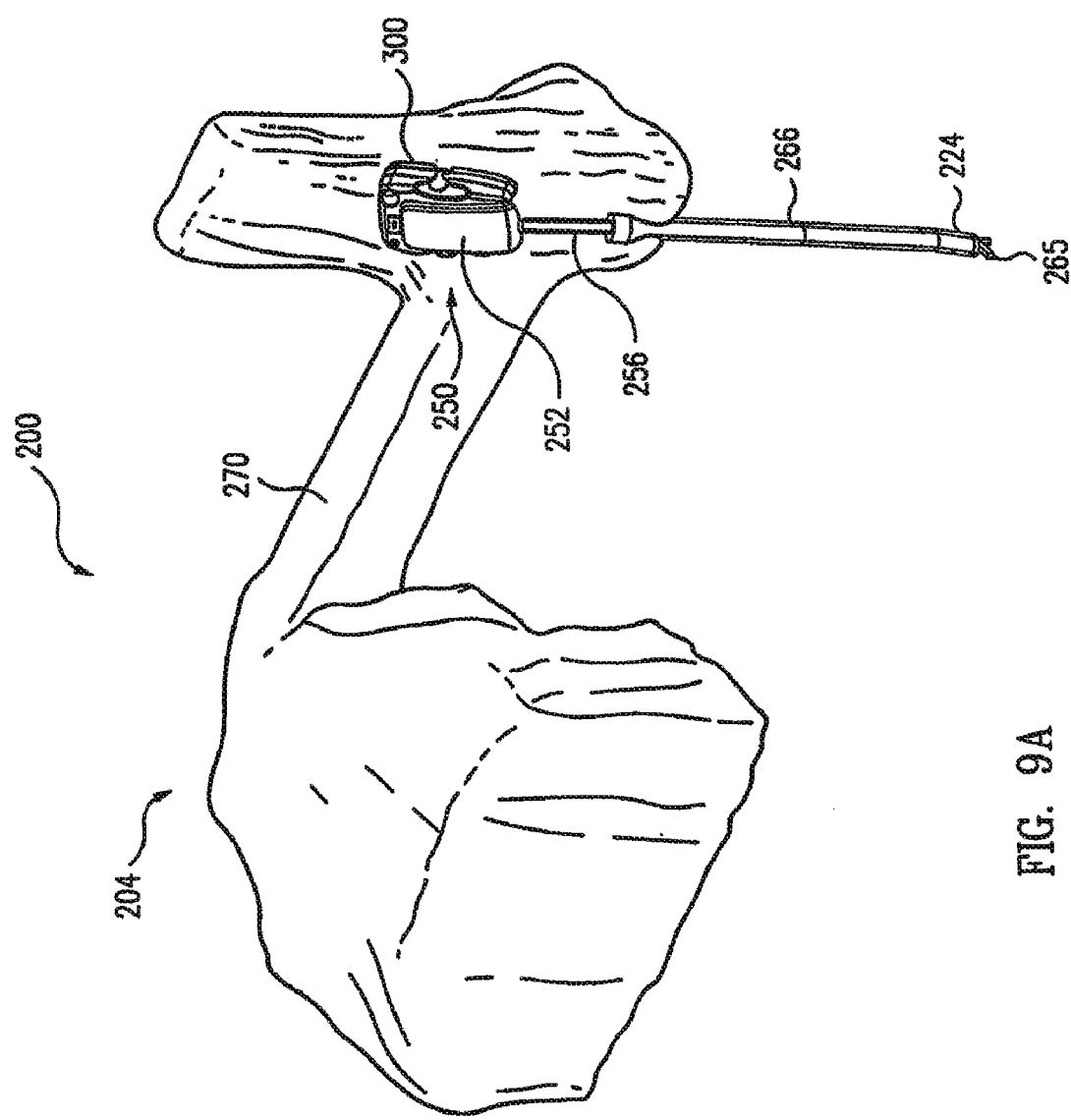
FIG. 9A is a perspective view of a sterile drape with installed surgical instrument on an instrument sterile adaptor (ISA) fully covering a robotic surgical manipulator in accordance with one embodiment of the present invention.
Figure 9B:
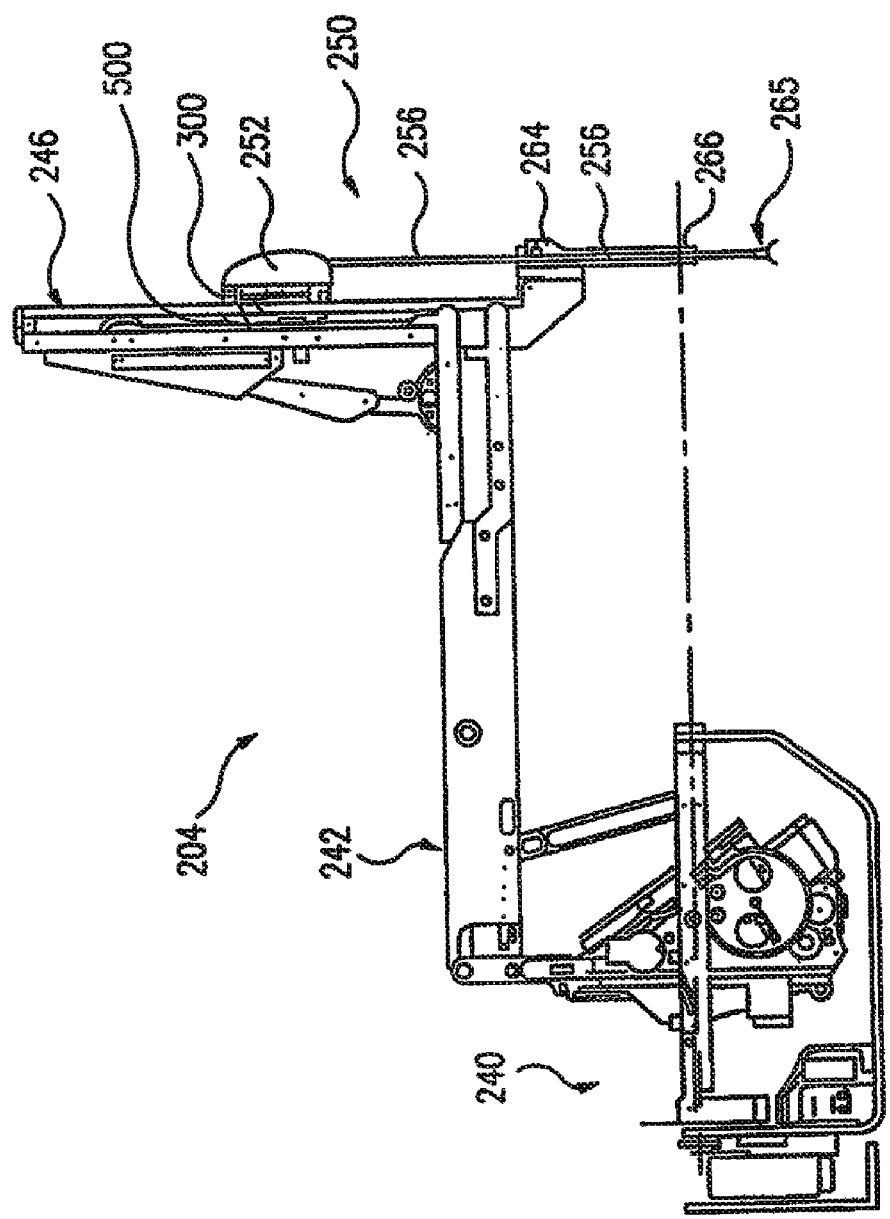
FIG. 9B is a side view of the surgical manipulator, installed surgical instrument, and integrated instrument sterile adaptor of FIG. 9A without a sterile drape portion.
Figure 10A:
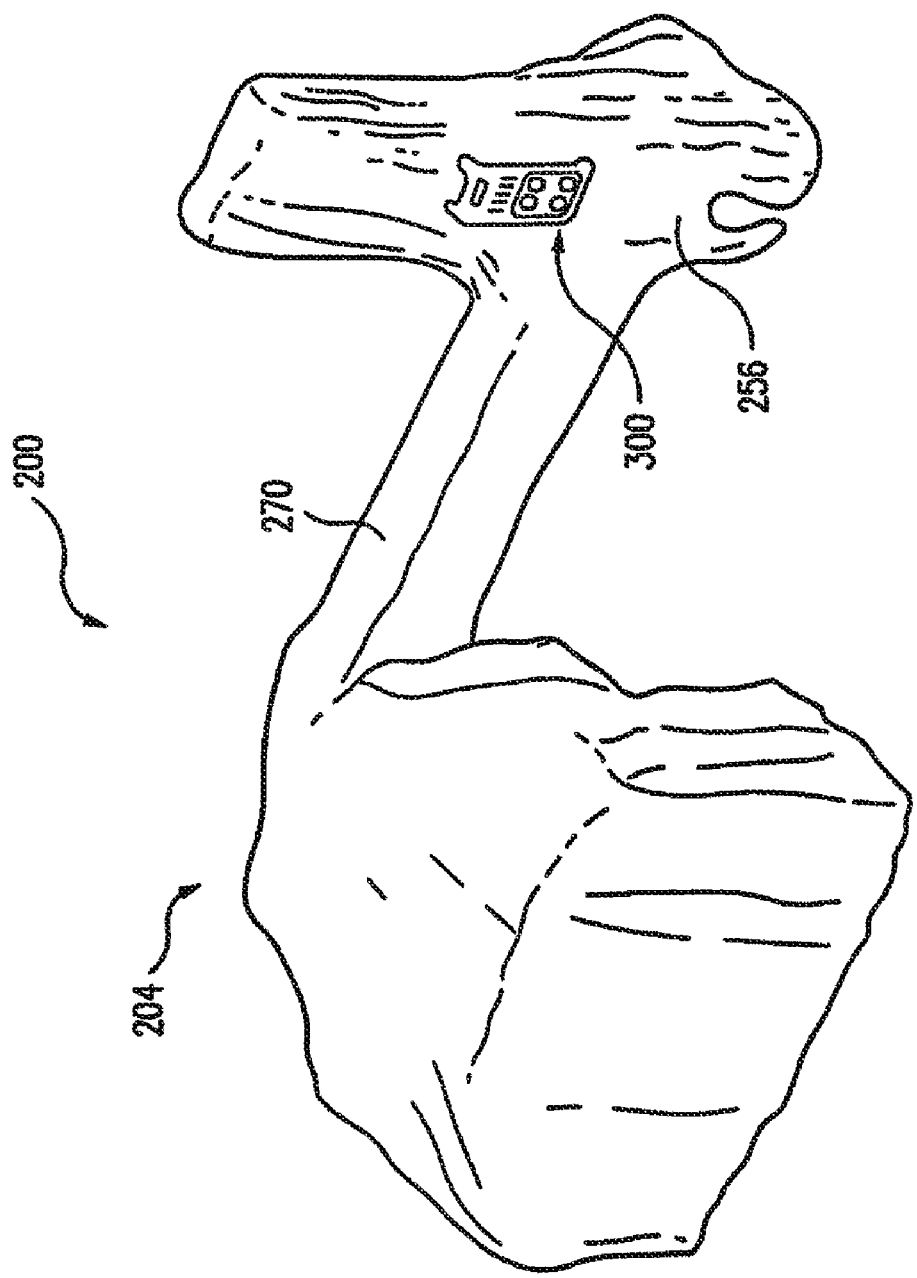
FIG. 10A is a perspective view of the sterile drape of FIG. 9A without the surgical instrument and surgical accessory in accordance with another embodiment of the present invention.
Figure 10B:
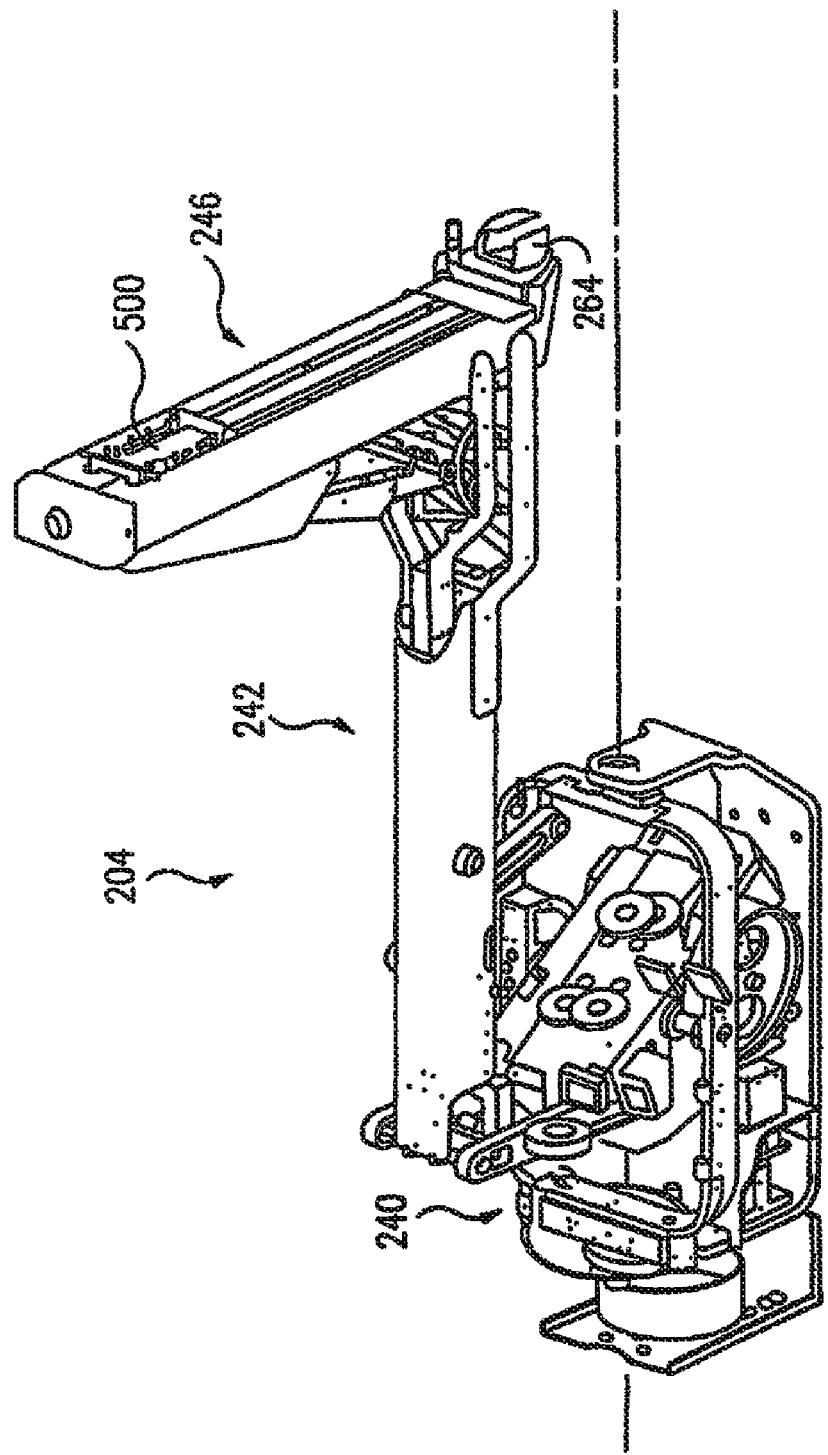
FIG. 10B is a perspective view of the surgical manipulator and accessory clamp of FIG. 10A without the sterile drape.

FIG. 9A shows a surgical instrument 250 installed on a instrument sterile adaptor (ISA) 300 integrated with sterile drape 270 in accordance with an embodiment of the present invention. ISA 300 is in turn operably coupled to an adaptor receiving portion 500 of the manipulator 204 (e.g., on the forearm 246. FIG. 9B is a side view of the robotic surgical manipulator of FIG. 9A without a sterile drape portion (except ISA 300 is shown) to illustrate a multiple degree of freedom arm coupling a driving assembly with ISA 300, an operably coupled surgical tool or instrument 250, a surgical accessory clamp 264, and an operably coupled surgical accessory 266. FIGS. 10A and 10B illustrate ISA 300 (integrated with sterile drape 270) and accessory clamp 264 without surgical instrument 250 and without surgical accessory 266, FIG. 10B being shown without drape 270. In one embodiment, ISA 300 may be permanently attached to the sterile drape by means of a film adhesive material which is impulse heat sealed and/or attached using adhesive film to the sterile drape.

System 200 is similar to the system shown and described above with respect to FIGS. 1-8 but adaptors (e.g., a wrist unit adaptor or a cannula adaptor) do not extend through holes in drape 270 to interface with a surgical instrument in the sterile field. Instead, ISA 300 is integrated with the sterile drape 270, and a portion of drape 270 effectively shields accessory clamp 264 from the sterile field of the surgery such that manipulator 204 is substantially fully covered by drape 270 during the procedure. In one embodiment, the drape is completely disposable.

Advantageously, ISA 300 and accessory clamp 264 are not required to be sterilized or replaced prior to or after a surgical procedure, thus allowing for cost savings, and since there is substantially full coverage by the sterile drape, system 200 is better shielded from the sterile field allowing for greater insulation of the system equipment and protection for the patient.

The same or similar manipulator assembly 4 including drive assembly 40, arm 42, forearm assembly 46, wrist unit adaptors 52, wrist units 22, and tools 24 (with the same or similar functionality) described above may be used within system 200 and with ISA 300 and accessory clamp 264, and repeated description of the same or similar part(s) is omitted. However, a different drive assembly 240, arm 242, forearm assembly 246, and interface 252 to actuate tool 224 with shaft 256 and end effectors 265 is illustrated in FIGS. 9A-9B and 10A-10B. Embodiments of drive assembly 240, arm 242, forearm assembly 246, and other applicable parts are described for example in U.S. Pat. Nos. 6,331,181, 6,491,701, and 6,770,081, the full disclosures of which (including disclosures incorporated by reference therein) are incorporated herein by reference for all purposes.

Embodiments of applicable surgical instruments 250, interfaces 252, adaptors, tools, or accessories are also described for example in U.S. Pat. Nos. 6,331,181, 6,491,701, and 6,770,081, the full disclosures of which (including disclosures incorporated by reference therein) are incorporated by reference herein for all purposes. It is noted that various surgical instruments may be used in accordance with the present invention, including but not limited to articulated tools with end effectors, such as jaws, scissors, graspers, needle holders, micro-dissectors, staple appliers, tackers, suction irrigation tools, and clip appliers, and non-articulated tools, such as cutting blades, cautery probes, irrigators, catheters, and suction orifices. Such surgical instruments are commercially available from Intuitive Surgical, Inc. of Sunnyvale, Calif.

Figure 11A:
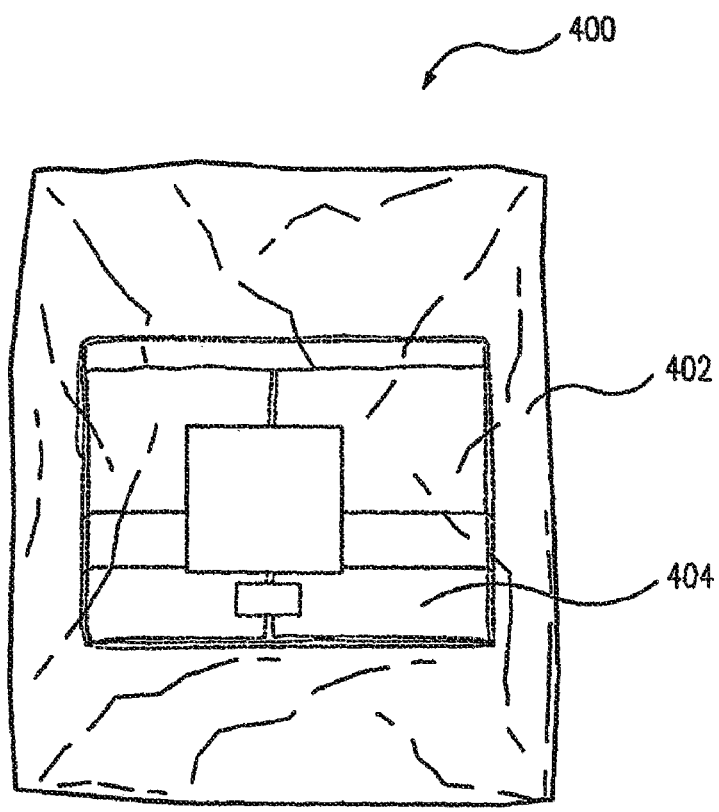

Referring now to FIGS. 11A-11M, a patient side manipulator (PSM) drape package 400 including a PSM drape 404 that is part of sterile drape 70 (described above with reference to FIG. 3A) is shown. PSM drape 404 may be a connected or disconnected section of sterile drape 70. FIG. 11A shows PSM drape package 400 including a PSM drape pouch 402 with PSM drape 404 folded inside. The PSM drape is designed to establish a sterile barrier between the non-sterile PSM arms and the sterile field of the surgical procedure. PSM drape 404 includes an integrated instrument sterile adaptor (ISA) 406 permanently mounted on the drape, with the complete assembly including the ISA, which is used to engage a surgical tool. Advantageously, various features of the PSM drape aid the draping and installation process.

Figure 11B:
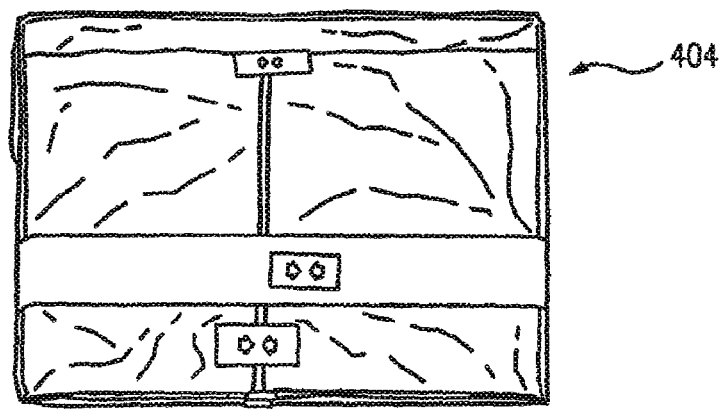
Figure 11C:
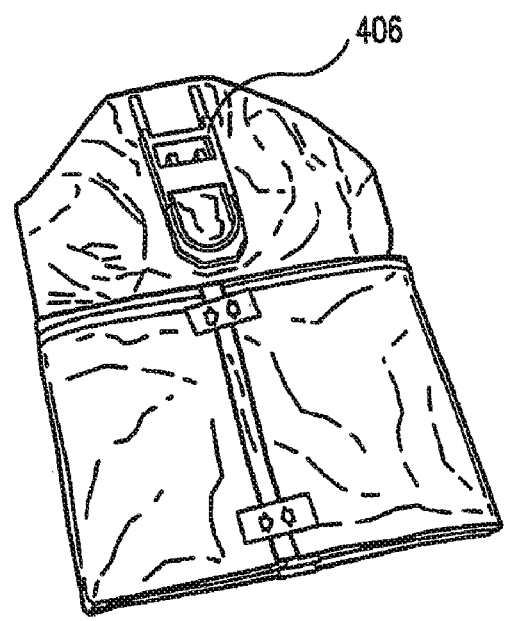
Figure 11D:
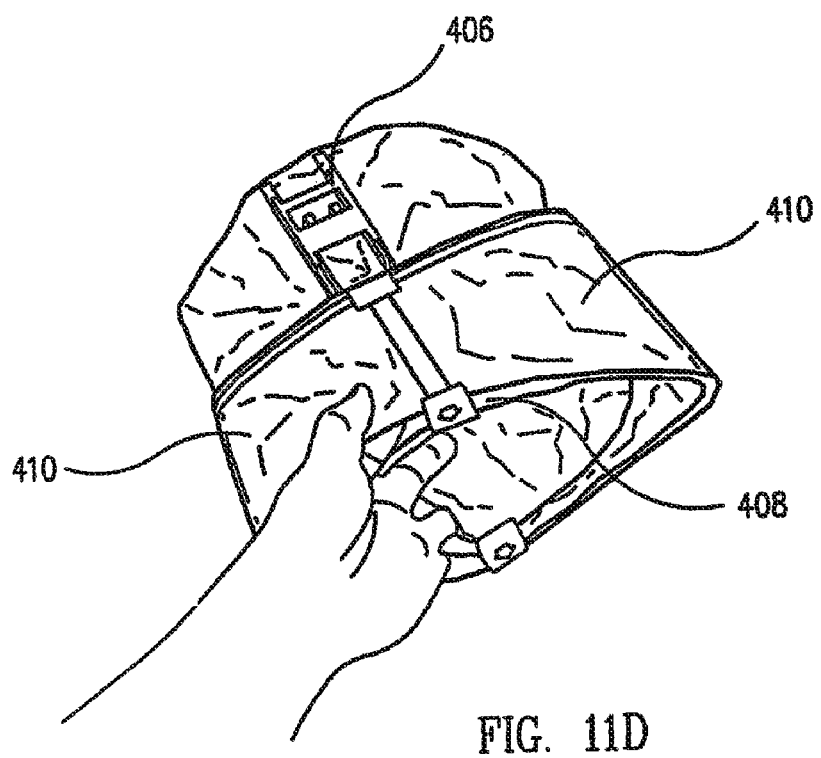
Figure 11E:
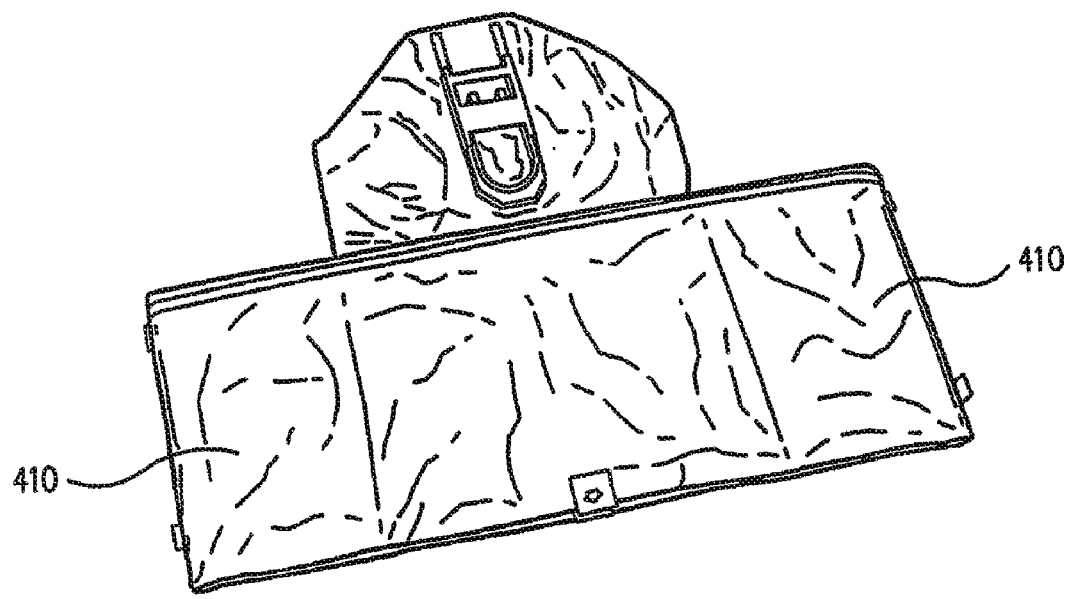
Figure 11F:
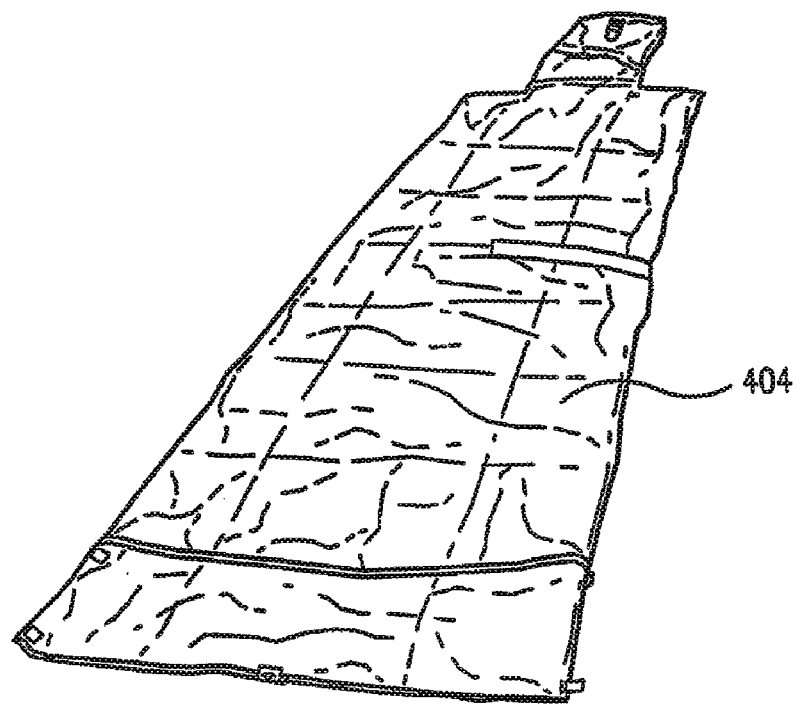

FIG. 11B shows PSM drape 404 removed from pouch 402. FIG. 11C shows an example of ISA 406 permanently mounted to PSM drape 404 proximate a closed end of PSM drape 404. FIG. 11D shows tear strips 408 that define the main hole in the folded PSM drape and folded flaps 410. FIG. 11E shows flaps 410 unfolded, and FIG. 11F shows PSM drape 404 completely unfolded. PSM drape 404 is packaged so that the folded drape can be first placed over the PSM arm and then the permanently mounted ISA 406 is attached to the PSM arm by first locating a front tongue feature into a bracket on the PSM arm followed by swinging the other end of the sterile adaptor until it engages a latch on the PSM arm. PSM drape 404 is maintained in this initial position by using tear strips 408 which allow for the controlled unfolding of the drape by tearing when pulled on with the necessary force. The user pulls the drape along the length of the PSM arm by placing their hands in integral cuffs 412 (FIG. 11G) and pulling the drape along the PSM arm.

FIGS. 11G1 and 11G2 show an integral cuff 412 at the open end of PSM drape 404, the edge of cuff 412 including a blue tape 411. The sterile scrub nurse may place his or her hands into the cuff when pulling the PSM drape along the PSM arm, and by using the cuff, the user is assured that their hands are not touching something that is non-sterile as they work their way along the PSM arm. Blue tape 411 acts as a physical marker on the drape to designate the sterile and non-sterile ends. By having this marker, a non-sterile person can know to pull on the non-sterile side when assisting the sterile scrub nurse.

Figure 11H:
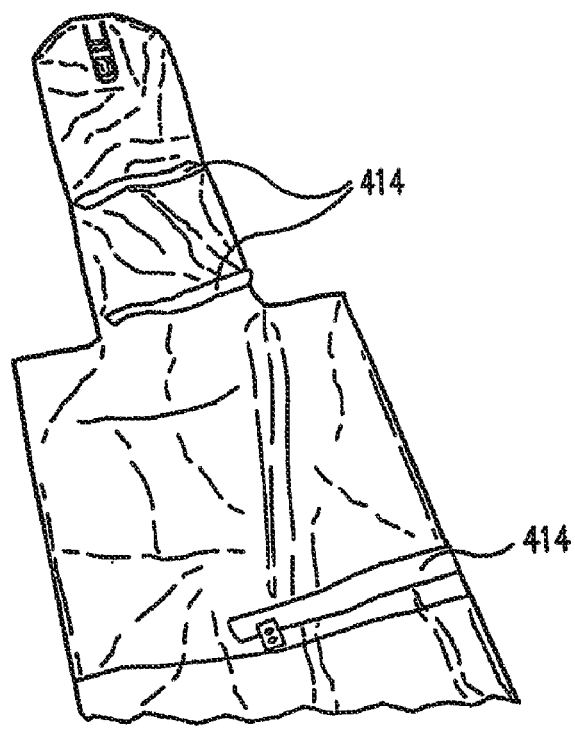

FIG. 11H shows straps 414 on the drape to help control the drape and reduce the visual size of the drape (i.e., reduce the volume of or space taken up by the unfolded drape). One strap is proximate the cannula mount area, another strap is proximate a "link 3" of the PSM arm, and another strap is along a "setup arm" (e.g., arm 42 of FIGS. 4 and 5) onto which the PSM arm is mounted.

Figure 11I:
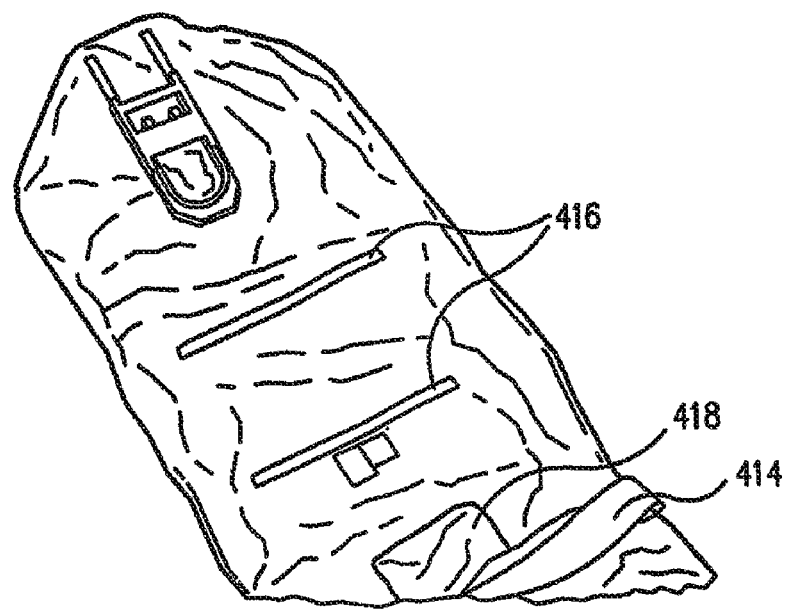

FIG. 11I shows strips 416 along the insertion axis and a cannula mount pouch 418. A cannula mount pouch that may be used is disclosed in co-pending U.S. patent application Ser. No. 11/240,087, filed Sep. 30, 2005, the contents of which have been previously incorporated by reference herein. Strips 416 are malleable strips on the drape in an insertion axis area. Strips 416 are attached to the drape between the sterile adaptor and the cannula mount area. Once the drape is installed on the PSM arm, the user can deform the malleable strips 416 to help fold back excess drape material. By being able to fold back and secure excess drape material, the drape can be made to closely fit the shape of the PSM arm. Advantageously, this reduces the visual size of the system and thereby allows more visibility of the patient and their surroundings to the surgeon or other user(s). Strips 416 are also sufficiently malleable to be able to open up to allow the system to achieve maximum range of motion without tearing the drape.

Figure 11J:
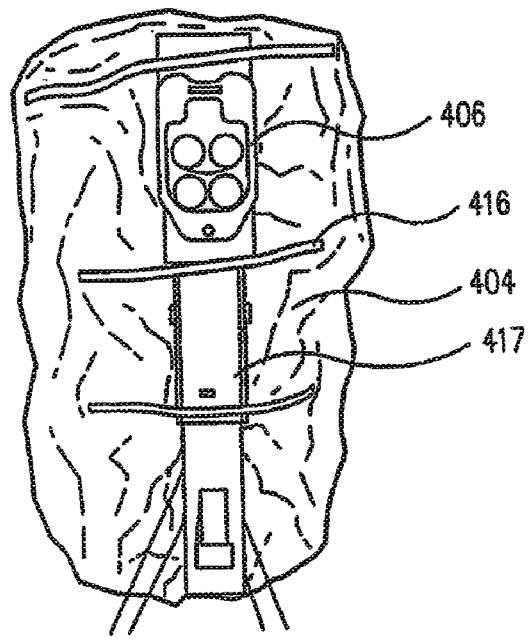
Figure 11K:
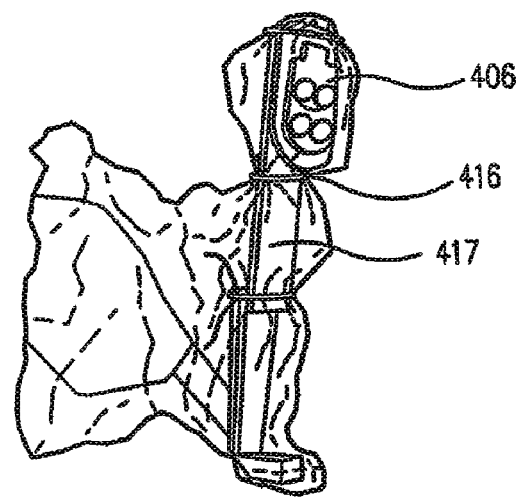
Figure 11L:
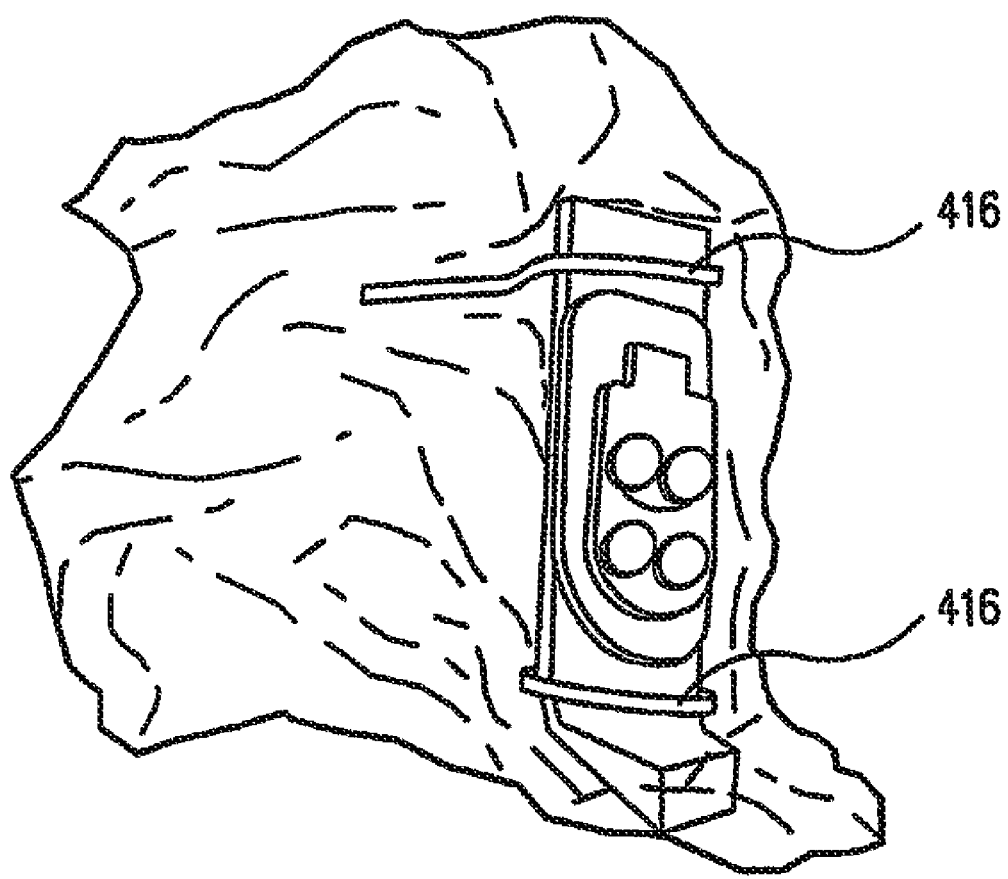

FIG. 11J shows PSM drape 404 over a portion of PSM arm 417 and a sterile adaptor 406 in place prior to strips 416 being bent back by the user. FIG. 11K shows strips 416 after being bent back by the user such that PSM drape 404 more closely fits the shape of the PSM arm, thereby reducing the size of the system. FIG. 11L shows another view of the strips 416 which are pliable enough to be opened for maximum range of motion and which can be reshaped by the user as desired during the procedure.

Drape 400 described above is preferably comprised of material of sufficient rigidity and strength to allow proper placement over a PSM arm and to resist tearing even under application of cyclical loads in various directions, but are preferably comprised of material of sufficient flexibility to allow movement with the active sections of the manipulator arms. Drape 400 may be comprised of various durable materials, and in one example is comprised of polyethylene, polyurethane, polycarbonate, or mixtures thereof. In one embodiment, drape 400 can be vacuum formed as part of a single drape or as separate drapes that can be attached to the main sterile drape 70 via adhesive, heat, RF welding, or other means. In another embodiment, drape 400 may be used as disconnected drapes (but possibly adjacent to one another or with overlap) to cover different portions of the surgical robot system.

ISA 300, adaptor receiving portion 500, and installation/engagement between ISA 300 and adaptor receiving portion 500 and between surgical instrument 250 and ISA 300 will now be described in greater detail.

Figure 12A:
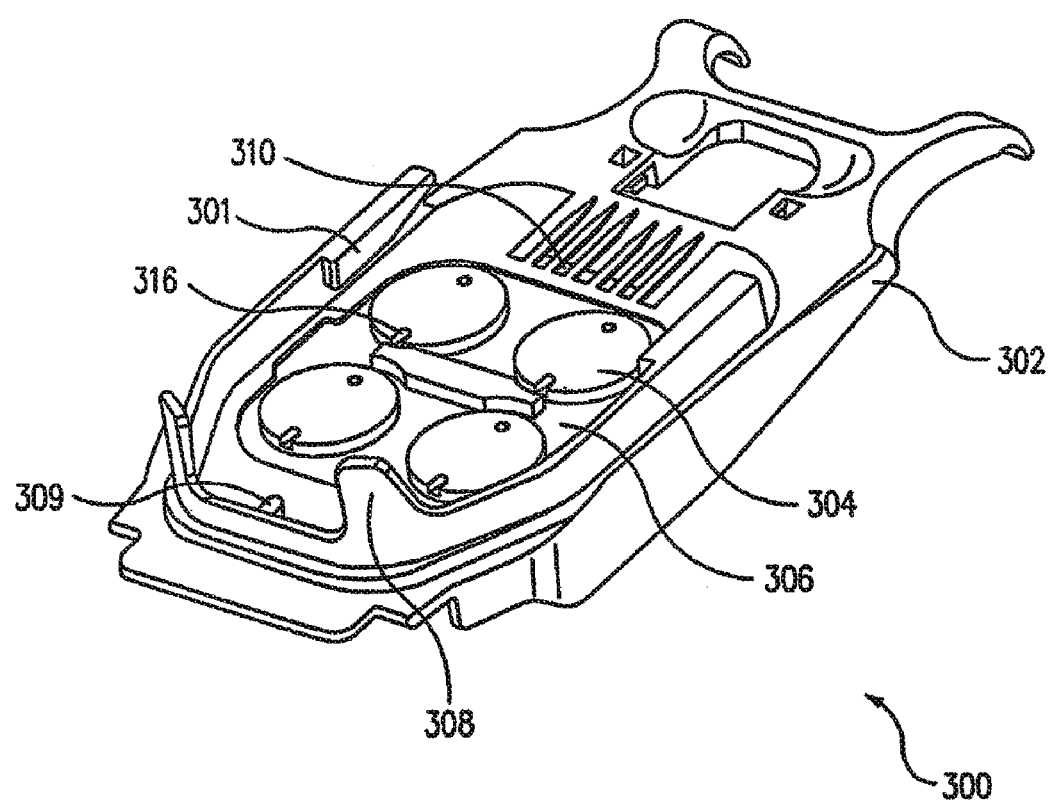
FIGS. 12A, 12B, and 12C illustrate a top perspective view, a bottom perspective view, and a sectional view of the ISA, respectively, in accordance with an embodiment of the present invention.
Figure 12B:
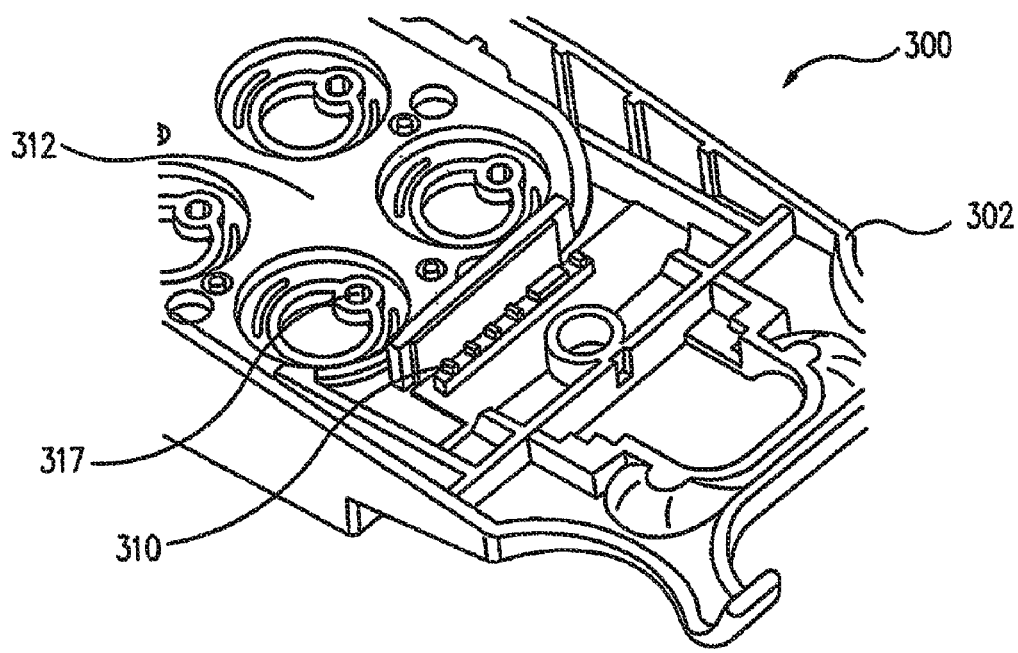
Figure 12C:
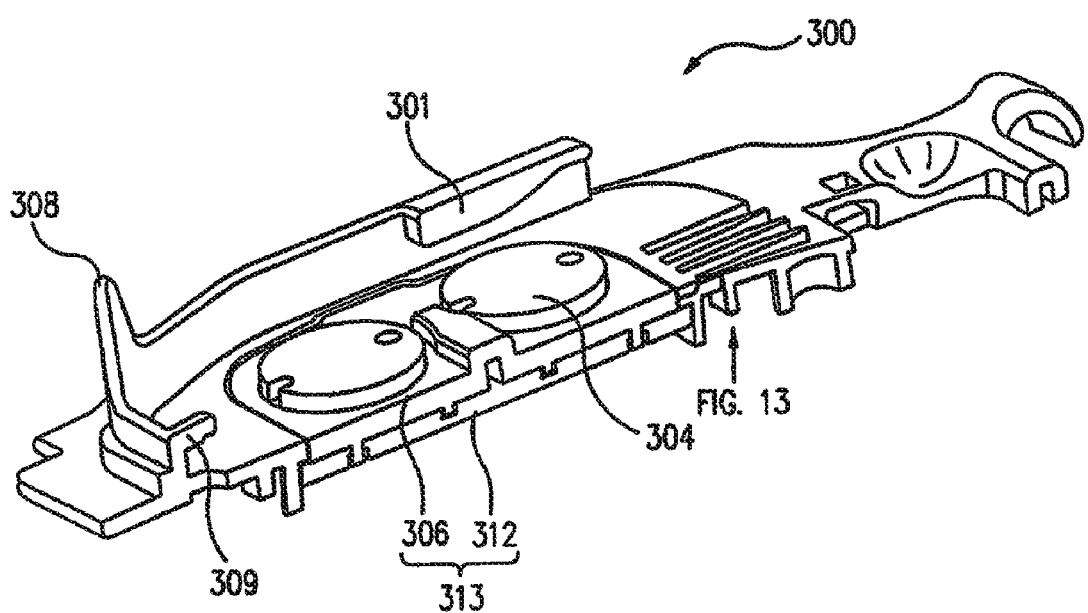

Referring to FIGS. 12A, 12B, and 12C, a top perspective view, a bottom perspective view, and a sectional view of ISA 300, respectively, are illustrated in accordance with an embodiment of the present invention. ISA 300 includes a housing 302, a disc 304, a top retractor plate 306, an instrument stop feature 308 of housing 302, a rail feature 301 of housing 302, a contact 310, and a bottom retractor plate 312. Top retractor plate 306 and bottom retractor plate 312 form a retractor plate assembly 313 which moves relative to housing 302. Discs 304 are captured inside of retractor plate assembly 313 and move relative to the assembly.

Figure 13:
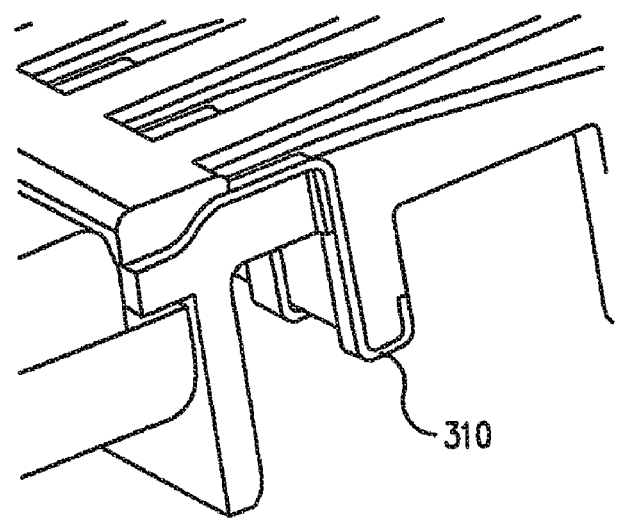
FIG. 13 illustrates a close up section view of an electrical contact of the ISA in accordance with an embodiment of the present invention.

FIG. 13 illustrates a close up section view of a contact 310, which is insert molded into the housing in one embodiment.

Figure 14A:
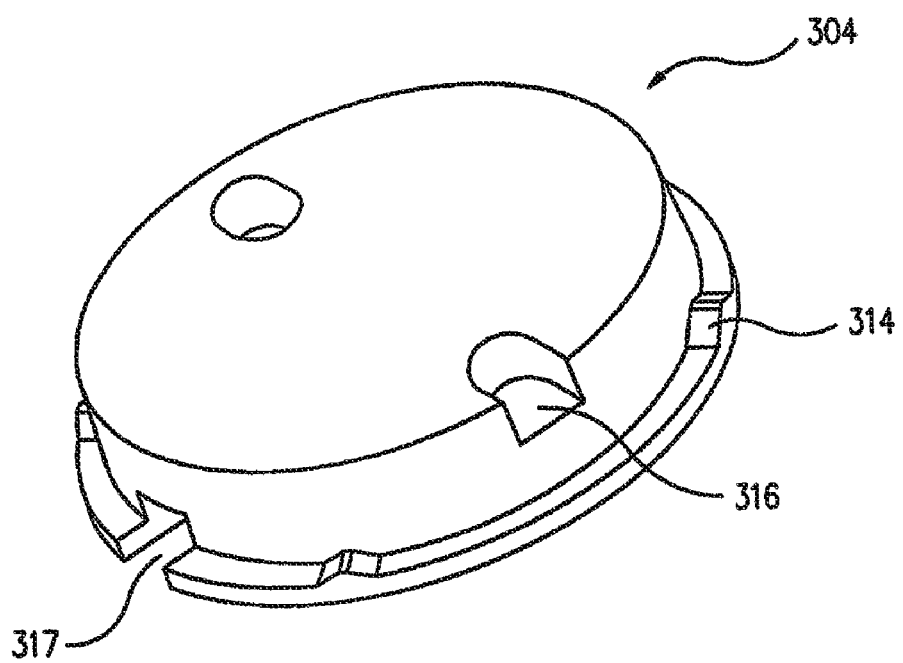
FIGS. 14A and 14B illustrate close up perspective top and bottom views of a disc of the ISA, respectively, in accordance with an embodiment of the present invention.
Figure 14B:
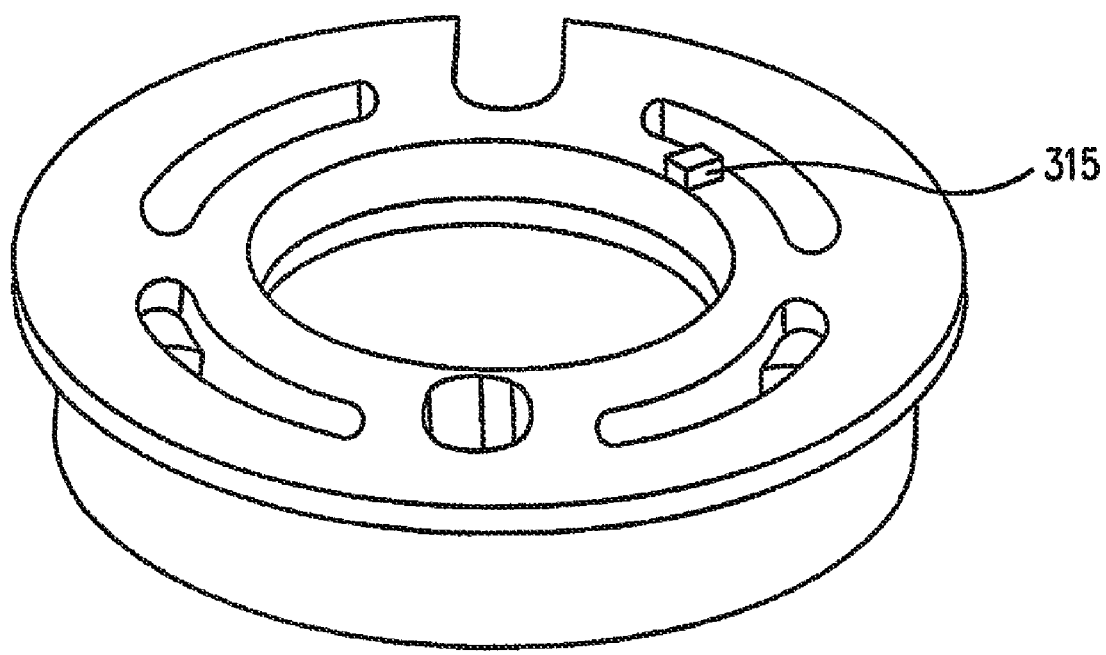

FIGS. 14A and 14B illustrate close up perspective top and bottom views of disc 304, respectively, which includes a tooth 314 at the base of disc 304, a hole 316 in the body of disc 304 for accepting pins 253 of a surgical instrument 250 (see FIGS. 17D and 17E), a hole 317 in the bottom of disc 304 for receiving pins 505 of spring loaded inputs 504 (see FIG. 16), and a tab 315 for moving disc 304 out of a dead zone, in accordance with an embodiment of the present invention. In this embodiment ISA 300 includes four discs 304 with each disc 304 including four teeth 314 and two holes 316. The four teeth 314 are placed 90 degrees apart in one embodiment. It is noted that in other embodiments, more or less discs, teeth, and slots are possible but need to operably couple to an adaptor receiving portion on the manipulator and a surgical instrument.

Figure 15A:
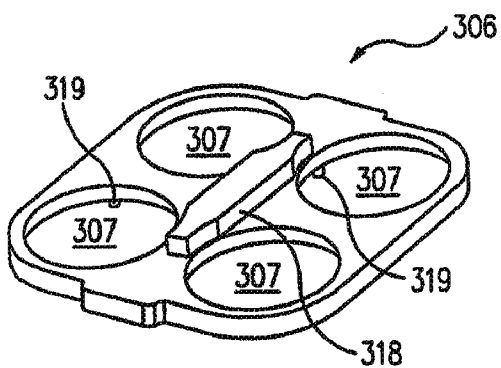
FIGS. 15A and 15B illustrate top and bottom perspective views of a top retractor plate of the ISA in accordance with an embodiment of the present invention.
Figure 15B:
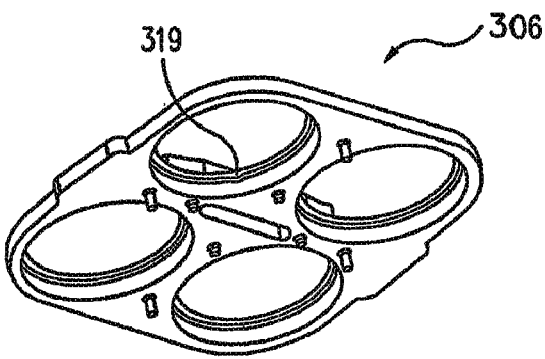

FIGS. 15A and 15B illustrate top and bottom perspective views of top retractor plate 306 in accordance with an embodiment of the present invention. Top retractor plate 306 includes a bar 318 for engaging the retractor plate and the retractor plate assembly and a tooth 319 for mating with a tooth 314 of disc 304 depending on relative position. As shown, top retractor plate 306 includes four apertures 307 for the four discs 304

Figure 16:
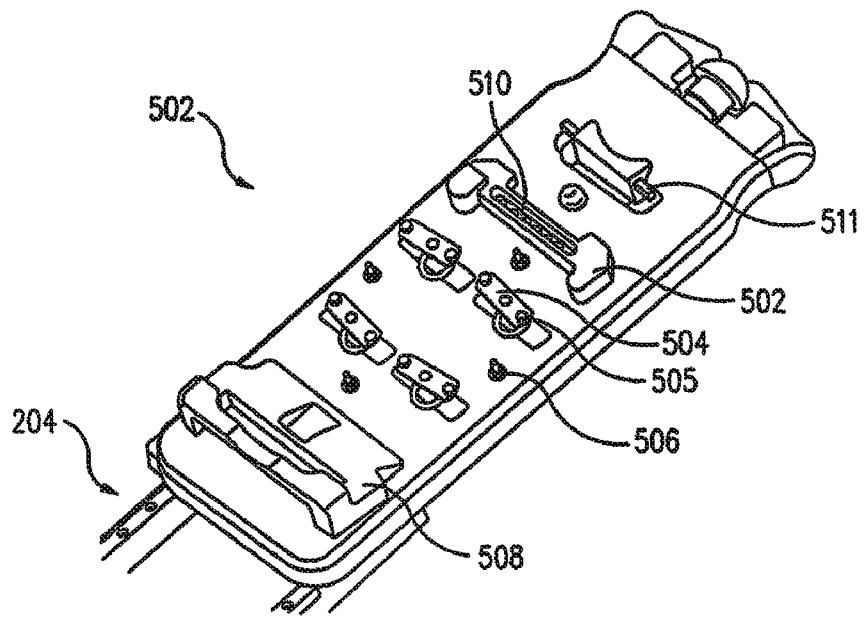
FIG. 16 illustrates a perspective view of an adaptor receiving portion of a manipulator in accordance with an embodiment of the present invention

FIG. 16 illustrates a perspective view of an adaptor receiving portion 500 of a manipulator 204 (e.g., a PSM) in accordance with an embodiment of the present invention. Adaptor receiving portion 500 includes a shroud 502 to isolate electrical contacts 510, a spring loaded input 504 having a pin 505, a spring plunger 506, and a bracket 508 to hold ISA 300 in place. In this embodiment, adaptor receiving portion 500 includes four spring loaded inputs 504 with each having two pins 505, and four spring plungers 506.

Referring now to FIGS. 17A through 17F, installation/engagement of ISA 300 to adaptor receiving portion 500, installation/engagement of surgical instrument 250 to ISA 300, and removal of surgical instrument 250 from ISA 300 are illustrated in accordance with an embodiment of the present invention.

Figure 17A:
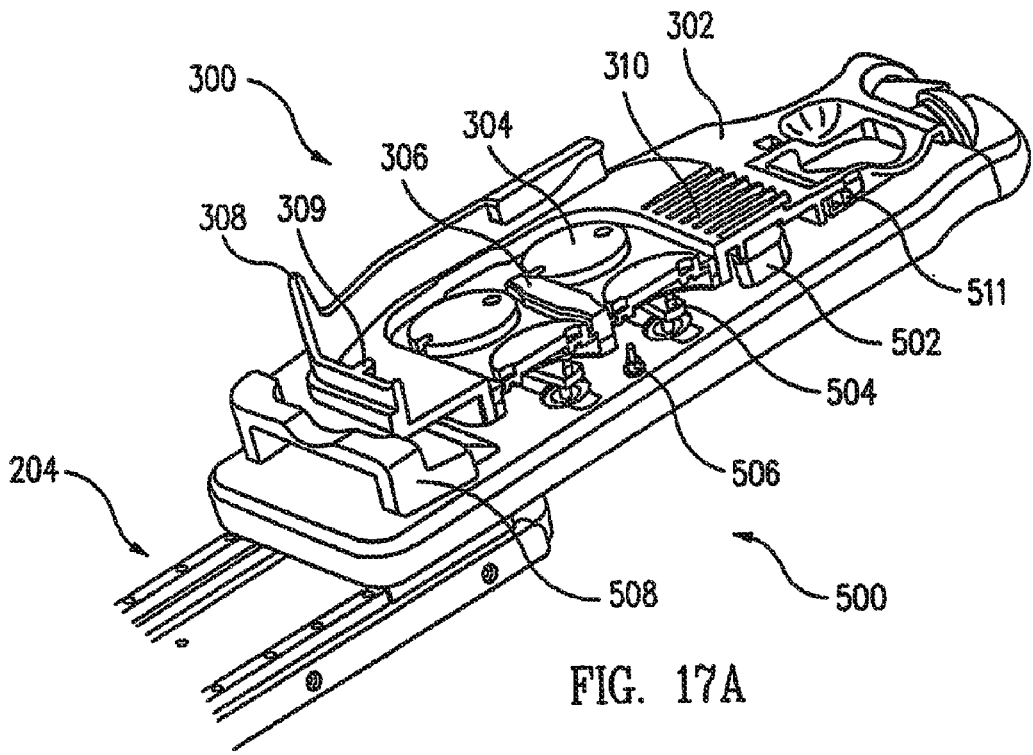
FIGS. 17A through 17F show installation/engagement of the ISA to the adaptor receiving portion, installation/engagement of the surgical instrument to the ISA, and removal of the surgical instrument from the ISA in accordance with an embodiment of the present invention.

FIG. 17A shows ISA 300 installed and engaged with adaptor receiving portion 500 of manipulator 204. ISA contacts 310 are coupled to manipulator contacts 510, discs 304 are engaged with spring loaded inputs 504, bottom retractor plate 312 is engaged with spring plungers 506, and instrument stop feature 308 mates with bracket 508. Instrument stop feature 308 allows for stopping of the instrument (for patient safety) if the user misses the rails 301 when installing the instrument onto the ISA. The instrument is fully stopped by bar 318 on top retractor plate 306 when installed. Prior to installation, spring loaded inputs 504 and spring plungers 506 are at their most extended position, and discs 304 of the ISA are free to rotate to any random location within the retractor plate assembly. In one embodiment, to install ISA 300 onto adaptor receiving portion 500, the user places the front section of the ISA housing into a bracket and swings the back end down thereby engaging a latch 511.

In this installed but pre-engaged position, discs 304 are pressed upward against top retractor plate 306 by spring loaded inputs 504, and retractor plate assembly 313 is pressed upward by spring loaded inputs 504 and spring plungers 506. In each disc location (aperture 307 of retractor plate 306), there is one tooth 319 on the retractor plate 306 which engages with teeth 314 of disc 304. The teeth configuration has multiple functions, one of which is to push discs 304 out of a "dead zone" which is an angular orientation where the holes 317 in the bottom of disc 304 are in a position where they may not mate with pins 505 of spring loaded inputs 504 since they do not rotate through a full 360 degrees. Another function of the teeth configuration is to prevent disc 304 from rotating more than 90 degrees during the sterile adaptor engagement sequence.

During the engagement sequence, disc teeth 314 mesh with retractor plate teeth 319 as spring loaded inputs 504 are activated to impart movement of disc 304 through friction between pins 505 and the bottom surface of disc 304 and through contact with tab 315. The presence of the four teeth 314 stops this rotational motion of disc 304, and pins 505 are allowed to line up with holes 317 of disc 304 as the spring loaded inputs 504 rotate relative to disc 304. As holes 317 on the bottom of disc 304 and pins 505 of spring loaded inputs 504 align, discs 304 drop onto spring loaded inputs 504. At this point, the teeth 319 of top retractor plate 306 clear the teeth 314 of disc 304 as disc 304 is dropped down, thereby allowing disc 304 to move freely through 360 degrees relative to retractor plate 306. When discs 304 are engaged onto spring loaded inputs 504, ISA 300 is engaged with adaptor receiving portion 500.

In one embodiment, the engagement sequence happens in milliseconds after installation of ISA 300 onto adaptor receiving portion 500. As ISA 300 is swung down into position, electrical contacts 310 engage electrical contacts 510 (e.g., pins) such that two initially open circuits on the manipulator 204 are closed, which activates the ISA engagement sequence. It is noted that the insert-molded contact 310 in housing 302 may have multiple electrical paths (vias) which engage with contacts on the adaptor receiving portion 500, and which are also used to establish communication with a surgical instrument 250 via instrument electrical contacts 255 (FIG. 17C).

Figure 17B:
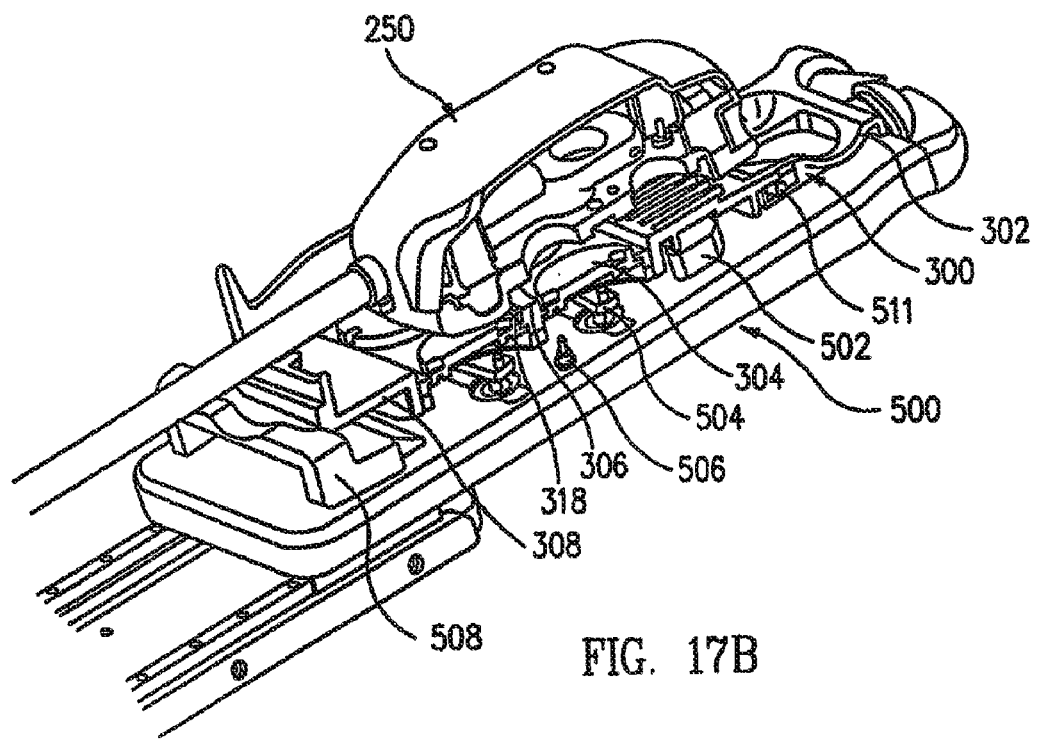
Figure 17C:
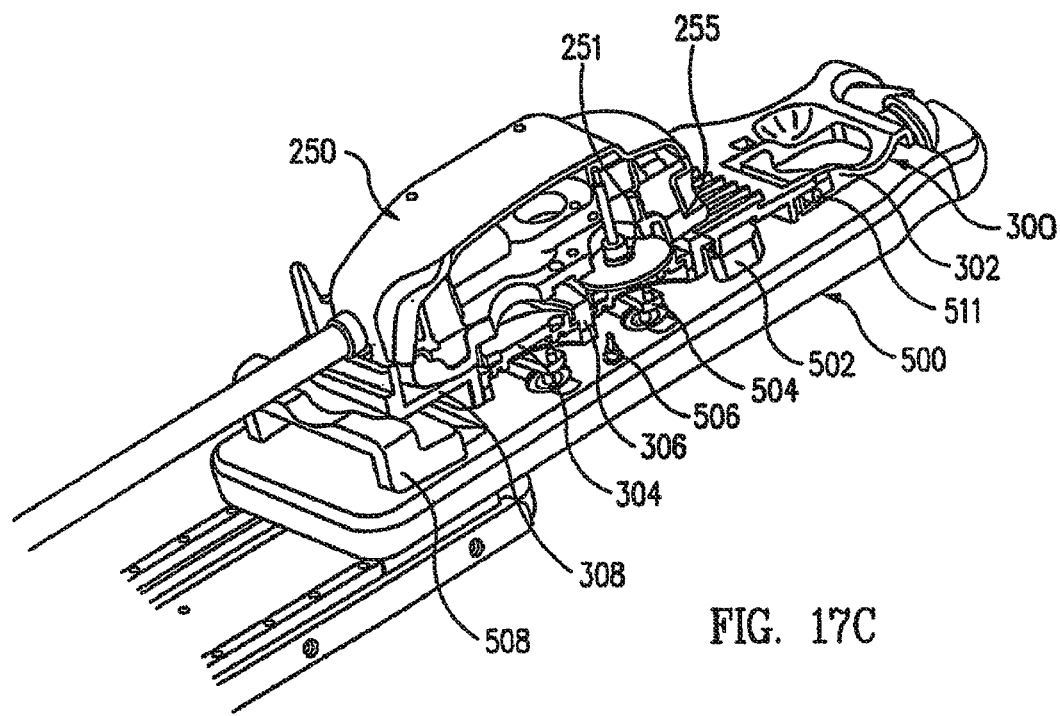

FIG. 17B shows surgical instrument 250 partially installed, and FIG. 17C shows surgical instrument 250 fully installed and engaged with ISA 300. Initially, as the user installs surgical instrument 250 onto ISA 300, retractor plate assembly 313 is pushed down toward adaptor receiving portion 500 as top retractor plate 306 is pressed down by instrument 250 engaging center bar 318. Prior to electrical engagement between instrument 250 and ISA 300, a chamfer on bar 318 engages a chamfer on the bottom of instrument 250, and as these two chamfers are aligned, the instrument is pulled into its home position due to the spring force of the spring loaded inputs and spring plungers. As the instrument is pulled into its home position; retractor plate assembly 313 begins to rise up into the surgical instrument, and in substantially the same motion, the electrical contacts 255 of instrument 250 come into contact with electrical contacts 310 of ISA 300. When instrument 250 is installed onto ISA 300, top retractor plate 306 is pressing on the bottom of the instrument and bar 318 is inside a clearance slot in the instrument housing. Prior to instrument engagement, discs 304 and spring loaded inputs 504 are pressed away from the instrument since the inputs on the instrument are not engaged with the holes 316 on the top of disc 304.

Figure 17D:
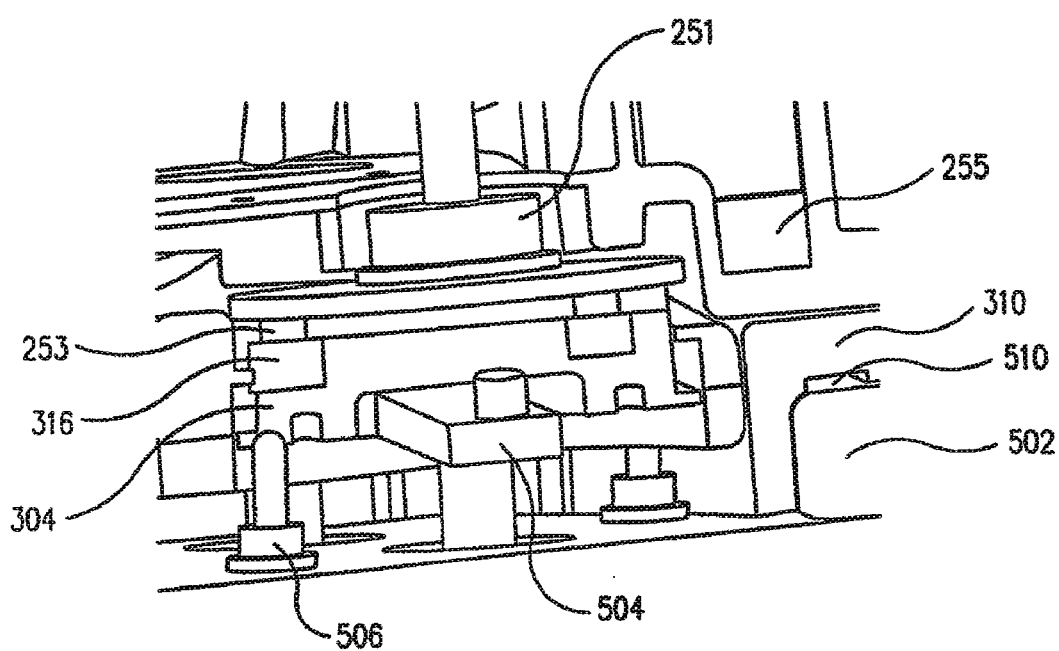
Figure 17E:
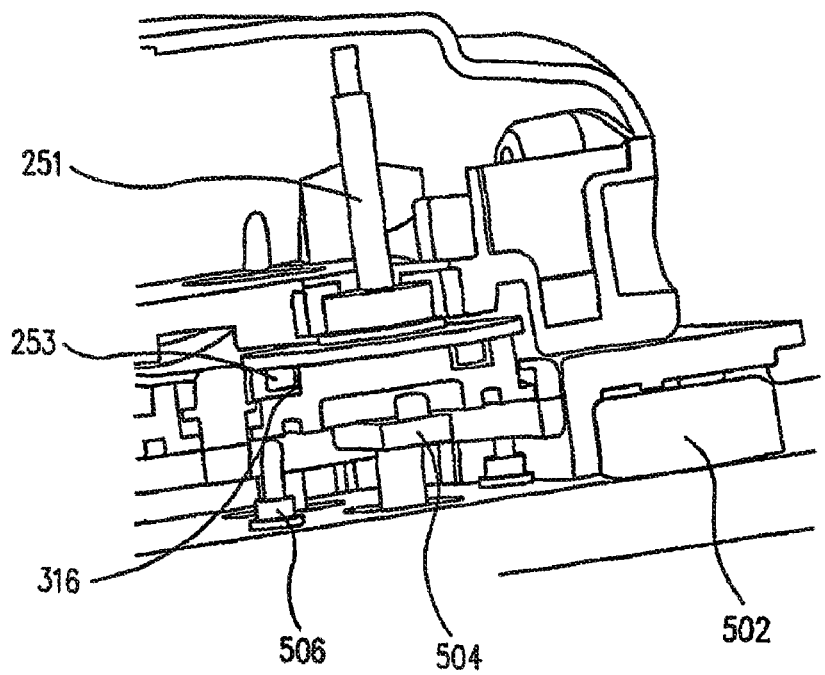

FIGS. 17D and 17E illustrate an engagement sequence of disc 304 with instrument 250. In FIG. 17D, disc 304 is not engaged with instrument 250 until disc 304 rotates to align with instrument disc 251, which is initially in a random position. As previously mentioned with respect to the engagement sequence between ISA 300 and adaptor receiving portion 500, as the electrical contacts of the instrument engage the contacts 310 of ISA 300, a normally open circuit on the ISA is closed which activates the instrument engagement sequence. Spring loaded inputs 504 and discs 304 rotate together as an assembly until the holes 316 of disc 304 engage with the pins 253 of instrument disks 251. When the holes are aligned with the pins, disc 304 and spring loaded inputs 504 is allowed to move upwards. FIG. 17E shows instrument disk 251 having a pin 253 which engages with hole 316 of ISA disk 304. At this point instrument 250 is considered engaged with ISA 300. It is noted that other contacts on ISA 300 may transmit electrical signals between the surgical system and instrument RTI board.

When the instrument is fully installed, it is held in position at three points along its housing. Two points are at the rail features 301 along the sides of the instrument, and a third point is at the center hold down tab 309 along the front center of the instrument. Advantageously, by holding down the instrument at three locations, the instrument is not over-constrained and installation and removal is made easier.

Figure 17F:
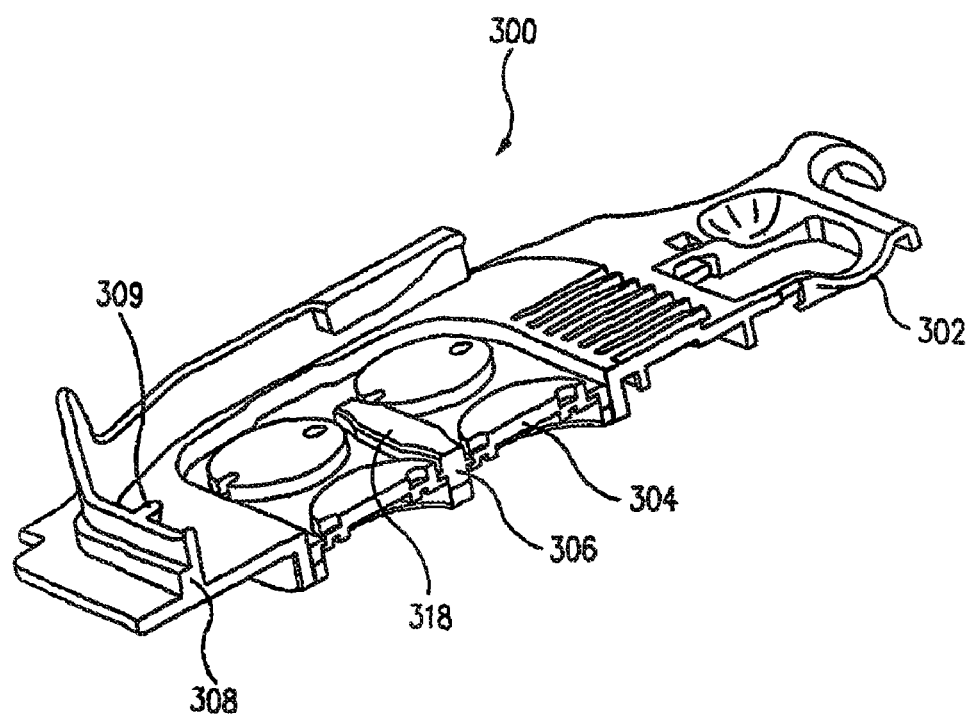

FIG. 17F illustrates removal of instrument 250 (not shown) from ISA 300. When the user wants to remove the instrument, levers on either side are squeezed and the instrument is pulled back out of the ISA. The levers on the instrument act on the center bar 318 of the top retractor plate, which in turn pushes the retractor plate down away from the instrument. As the retractor plate moves further away, the discs 304 are disengaged from the pins of the instrument allowing for removal of the instrument.

Figure 18:
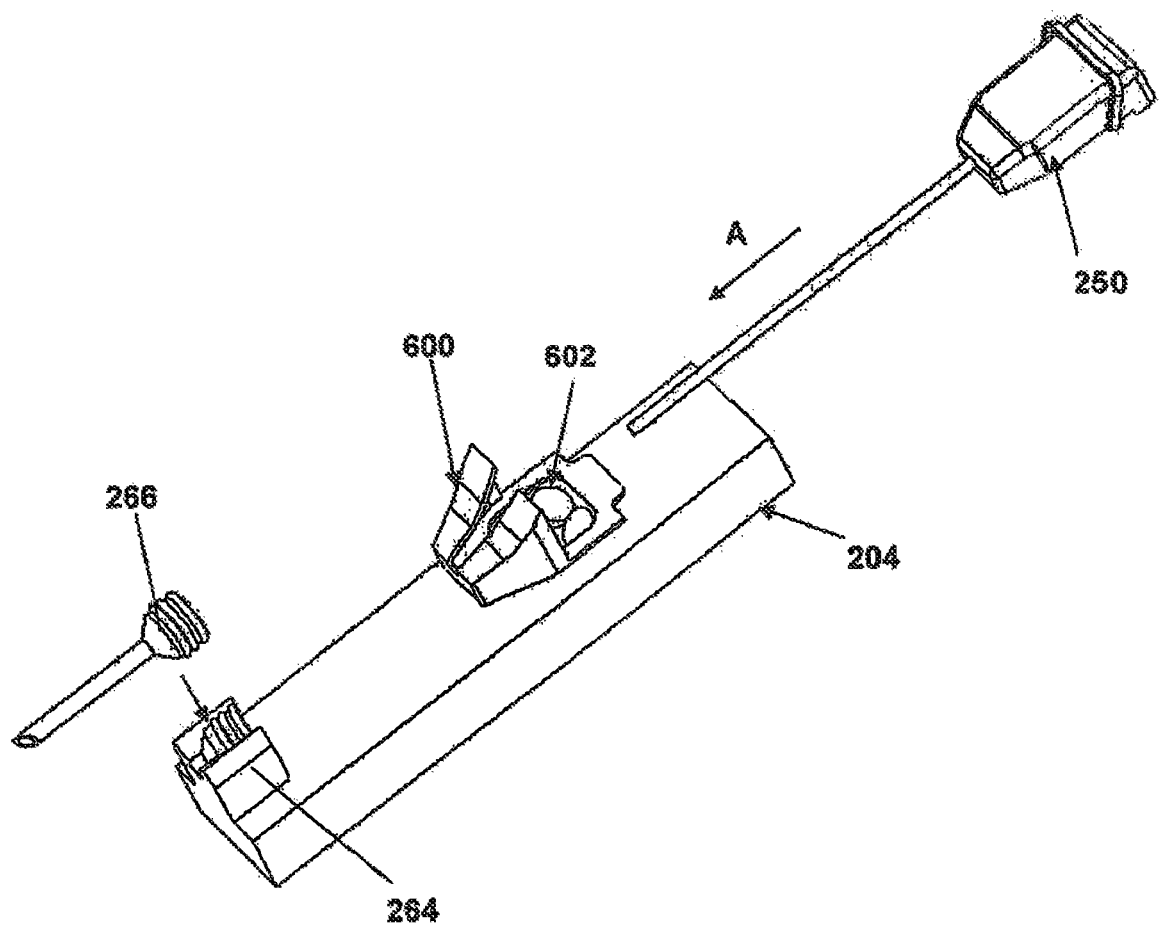
FIG. 18 illustrates some basic features of an ISA in accordance with another embodiment of the present invention.

Referring now to FIG. 18, basic features of an ISA 600 are illustrated in accordance with another embodiment of the present invention. ISA 600 is incorporated into a sterile drape (not shown) and in particular is used to cover substantially the entirety of a patient side manipulator (PSM) arm 204. A drape interface is between an instrument 250 and PSM arm 204 where the instrument and PSM arm interface proximate area 602, thereby providing a substantially sealed sterile field from the non-sterile robotic arm. Instrument 250 is inserted onto ISA 600 with a motion generally along the insertion axis "A" (shown by the arrow). Features at the front, back, and sides of ISA 600 may secure or retain the instrument to the arm 204, and the connection between the instrument and the ISA is able to withstand axial and radial loads relative to the drape interface of the ISA. A "wedge" design of the ISA housing may be used to guide the instrument onto the ISA to allow for more initial misalignment of the instrument while still achieving a positive connection. A surgical accessory 266 for operably coupling to an accessory clamp 264 is also shown.

The sterile adaptor of the present invention provides an attachment method and apparatus between a sterilized instrument and a non-sterile robotic arm. This attachment must still allow the transmission of the instrument wrist axes (innerpitch, inner-yaw, roll, and instrument grasping) and the transmission of electrical sensors/signals without breaching sterility. Another key concept with this adaptor is to clearly define (mechanically) the engagement sequence of the adaptor onto the robot arm and the instrument onto the adaptor. This clear definition will make the engagement predictable and therefore allow for a reliable detection of the engagement. All of the different design concepts have specifically defined engagement sequences to properly connect the instrument to the sterile adaptor/robot arm that are similar however the transmission of the axes varies greatly. Also, with these designs the desire is to make them efficiently enough to incorporate them directly into the full arm drape and therefore make them disposable. To support this requirement much complexity has been moved out of the sterile interface and into either the instrument or the robot arm. Some examples are the removal of the PCA on the sterile adaptor and use of vias, removal of the springs for the sterile adaptor and using spring loaded inputs on the robot arm, and redesigning the parts in the sterile adaptor so they can be molded.

Several different methods and apparatus were researched and prototyped to improve on the mechanical engagement and sterile barrier. These different embodiments are described below.

Referring now to FIG. 19, another ISA known as a "swash plate" embodiment is illustrated in accordance with an embodiment of the present invention. An ISA 700 includes a drape interface 704 including a drape portion in the area 702. An instrument 250, including instrument inputs 280, front tabs 291, and back tab 292, may be operably coupled to ISA 700.

FIG. 20 illustrates the interface of a sterile drape portion 701 between an instrument input 280 and drape interface 704, and FIG. 21 illustrates instrument input 280 in accordance with this embodiment of the present invention. Drape interface 704 includes a base 705 and an internal bearing that creates a rotating disk 708 including an indent 706 in one embodiment. Instrument input 280 includes a main shaft 282, an internal bearing 284, a rotating disk 288, and a nub 286 on the rotating disk 288. Although drape portion 701 is between input 280 and interface 704 to effectively maintain a sterile field, rotating disks 288 and 708 of input 280 and interface 704, respectively, can rotate 360 degrees and transmit torque with the drape portion 701 flexing in an up-and-down direction without tearing. Instrument input 280 drops down into place and is aligned with nub 286, which may be spherical or a portion of a cone in one example, and that mates with indent 706 on rotating disk 708 of drape interface 704. Nub 286 helps to keep the input of the instrument and the input of the robot arm (PSM) aligned even while torque is being transmitted. In this embodiment, each of a plurality of drape interfaces 704 operably couples to a respective instrument input 280.

Figure 22A:
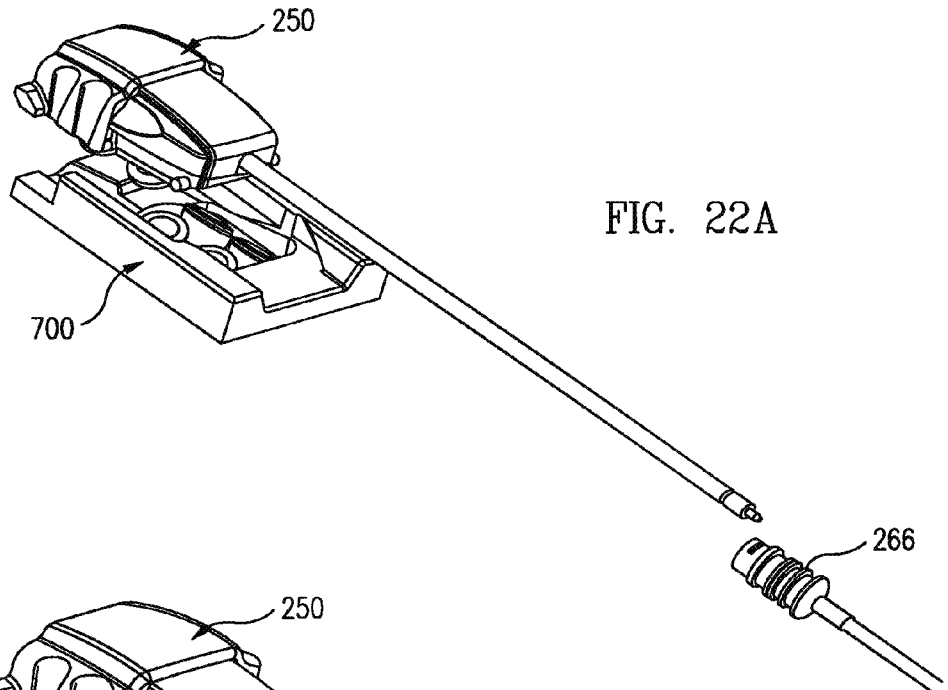
FIGS. 22A-22C and 23A-23C illustrate an engagement sequence of an instrument and the ISA of this embodiment.
Figure 22B:
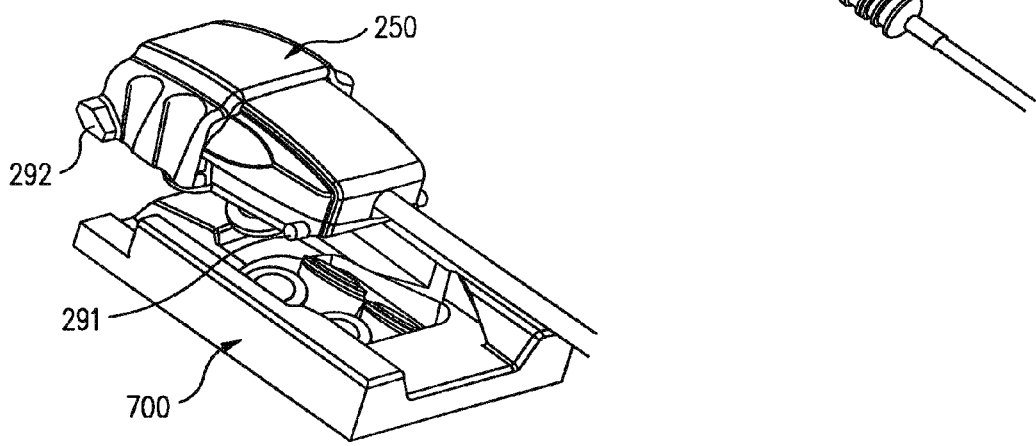
Figure 22C:
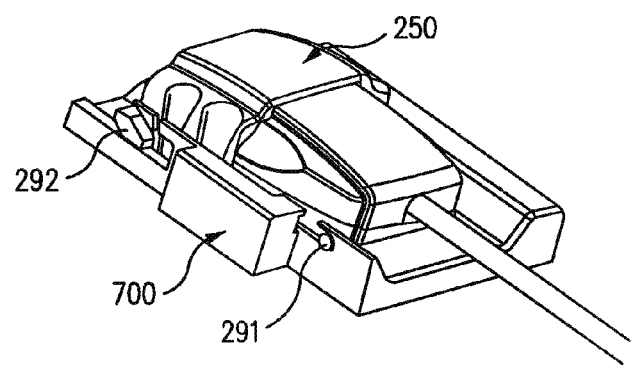
Figure 23A:
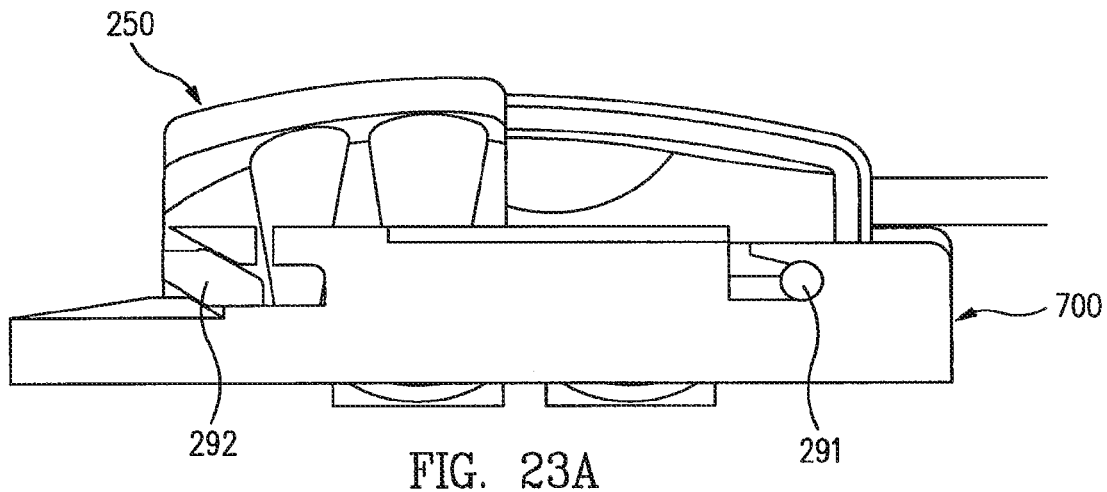
Figure 23B:
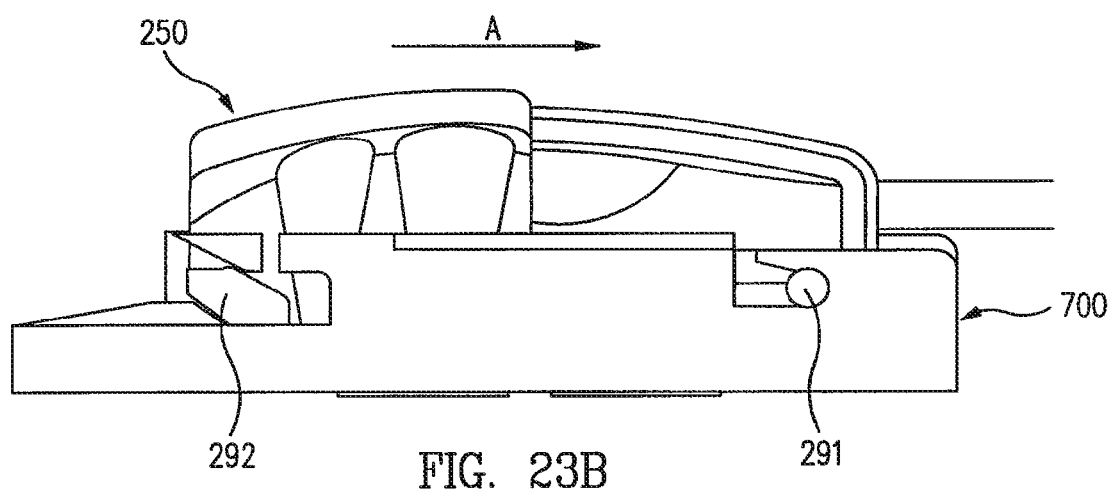
Figure 23C:
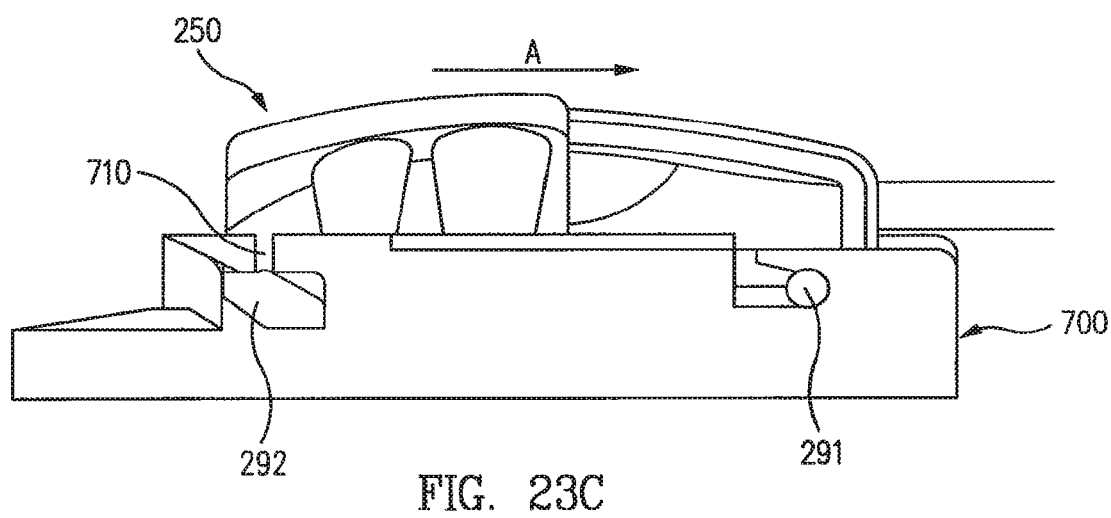

FIGS. 22A-22C and 23A-23C illustrate an engagement sequence of an instrument 250 to the ISA 700 of this embodiment. In FIG. 22A, the tip of instrument 250 is first placed into surgical accessory 266 (e.g., a cannula). Then, front tabs 291 are inserted into ISA 700, as shown in FIG. 22B. Finally, back tab 292 is slid into place on ISA 700, as shown in FIG. 22C. FIG. 23A shows the front tabs 291 inserted into ISA 700 while back tab 292 is initially extended and held up by a bump. FIG. 23B shows back tab 292 continuing to slide forward as instrument 250 slides forward (shown by arrow A) and the instrument 250 dropping into place on ISA 700. FIG. 23C shows a nub in the instrument housing tab 292 snapping into a groove 710 in ISA 700 for final contact engagement.

Figure 24A:
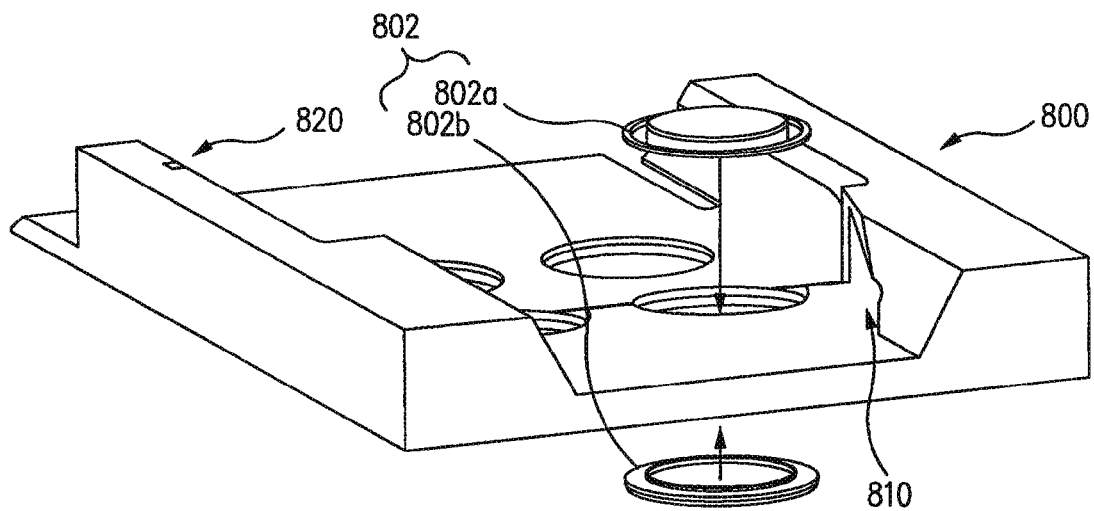
FIGS. 24A and 24B illustrate another ISA in accordance with an embodiment of the present invention.
Figure 24B:
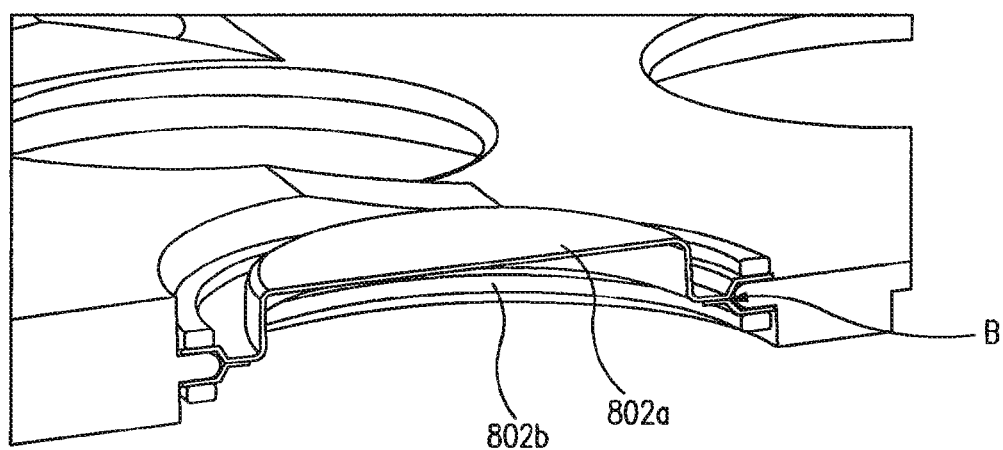
Figure 25A:
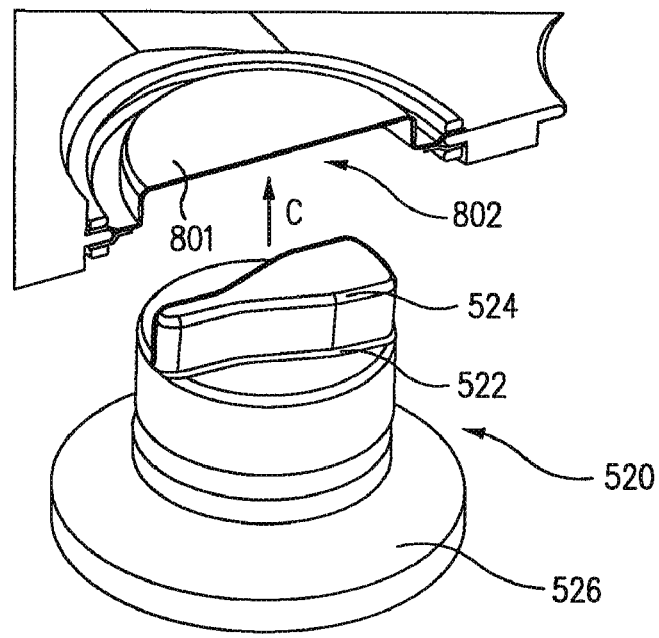
FIGS. 25A-25C illustrate a PSM input and a drape interface of the ISA in accordance with this embodiment of the present invention.

Referring now to FIGS. 24A and 24B, another ISA known as a "flask input" embodiment is illustrated in accordance with an embodiment of the present invention. An ISA 800 includes separate drape interfaces 802 for each PSM input 520 (FIG. 25A). FIG. 24A shows an exploded view of one of four drape interfaces 802, and FIG. 24B shows a close-up sectional view of a drape interface area, in particular an area B where the drape interface is assembled (e.g., by welding).

Figure 25B:
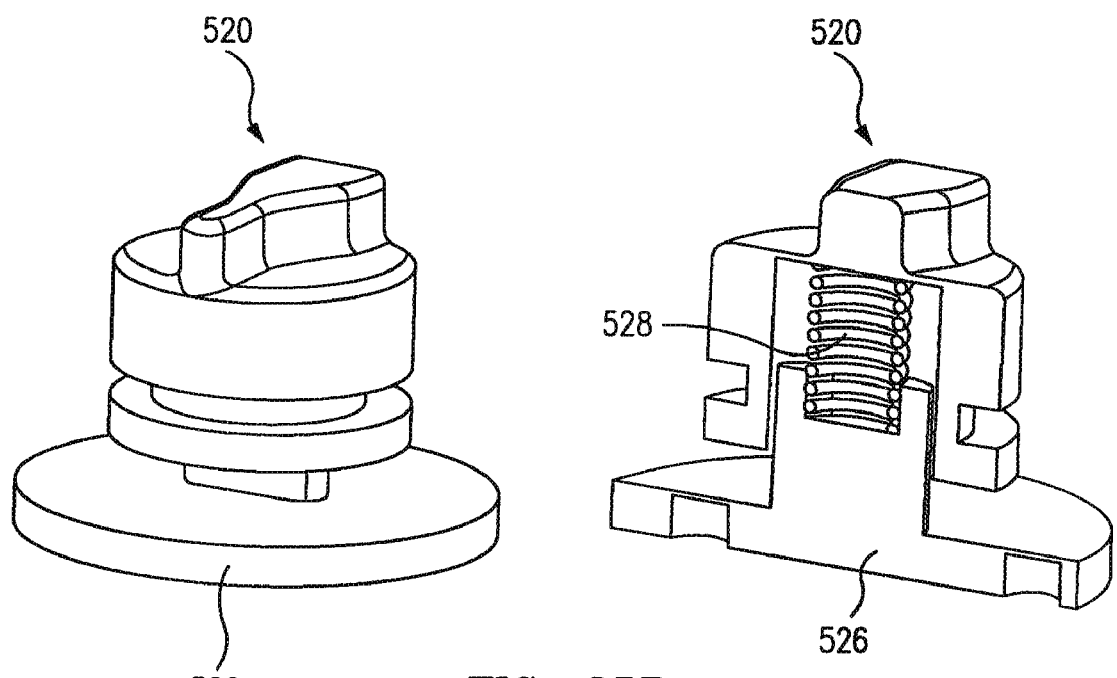
Figure 25C:
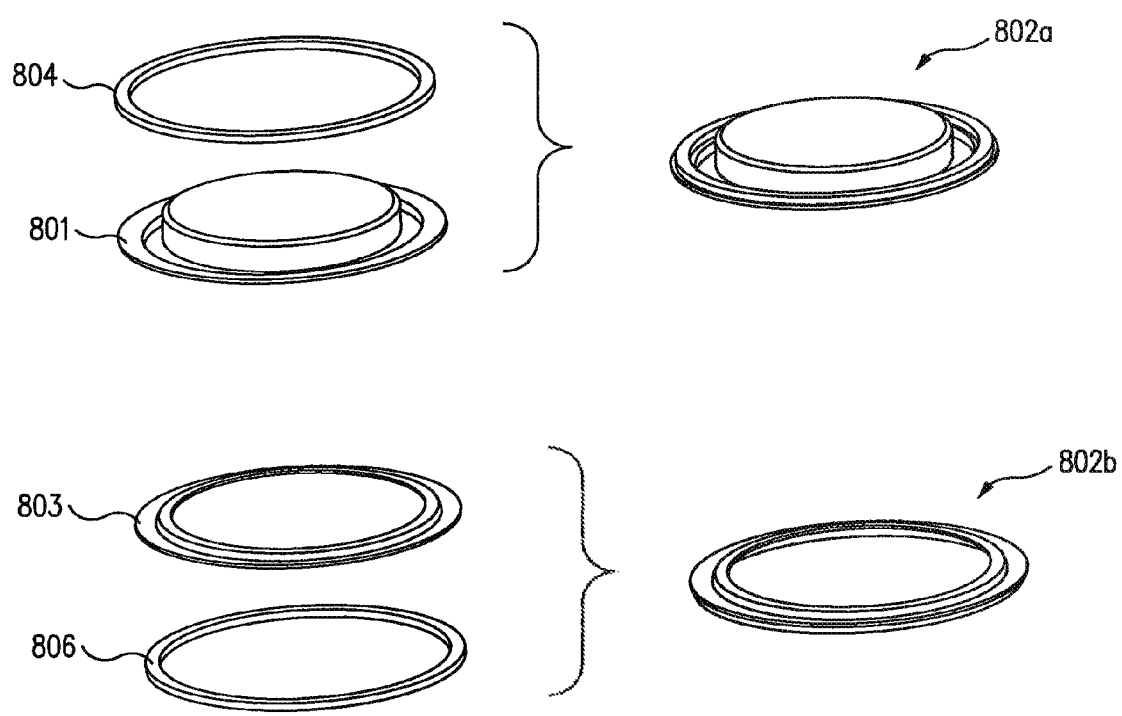

FIGS. 25A-25C illustrate PSM input 520 and drape interface 802 in greater detail in accordance with this embodiment of the present invention. PSM input 520 includes alignment features 522 and 524 for coupling to instrument inputs (not shown) in a particular orientation but with minimal sharp edges to minimize or reduce drape tearing while allowing for input misalignment. PSM input 520 (FIG. 25B) further includes a spring 528 and a plate 526 for providing a spring-loaded input. A drape interface 802 (FIG. 25C) includes a top portion 802a and a bottom portion 802b in this embodiment. Top portion 802a includes a ring 804 and a drape portion 801 which are assembled together, and bottom portion 802b includes a ring 806 and a liner 803 which are assembled together. During the attachment of drape portion 801 to ring 804, the drape may be placed on a form to create an extended pocket. Top portion 802a and bottom portion 802b are placed on either side of the ISA housing and assembled along area B, which may be done by various means and methods, including but not limited to welding and bonding (FIG. 25A).

As further shown by arrow "C" in FIG. 25A, PSM input 520 is pressed into drape interface 802 during installation of the ISA 800 to the PSM, and the drape portion 801 deforms into a shape covering the top surface of PSM input 520. Advantageously, ISA 800 is easily engaged to the PSM since the membrane does not have to line up with specific features on the PSM inputs. PSM inputs simply need to be positioned within the rings of drape interface 802.

Figure 26A:
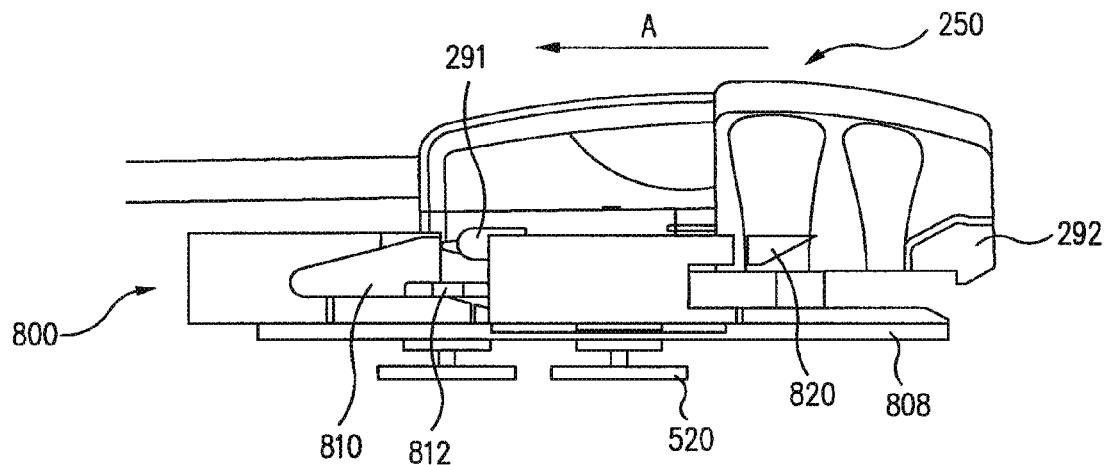
FIGS. 26A-26E illustrate an engagement sequence of an instrument and the ISA of this embodiment.
Figure 26B:
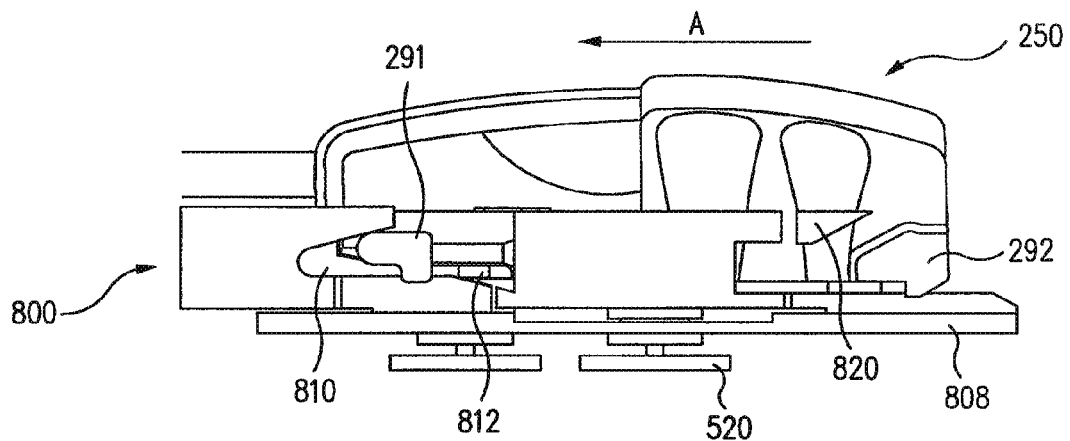
Figure 26C:
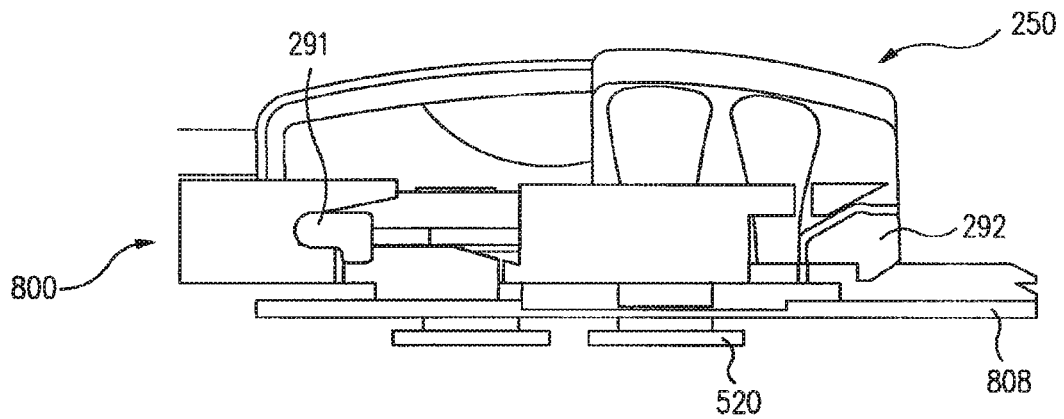
Figure 26D:
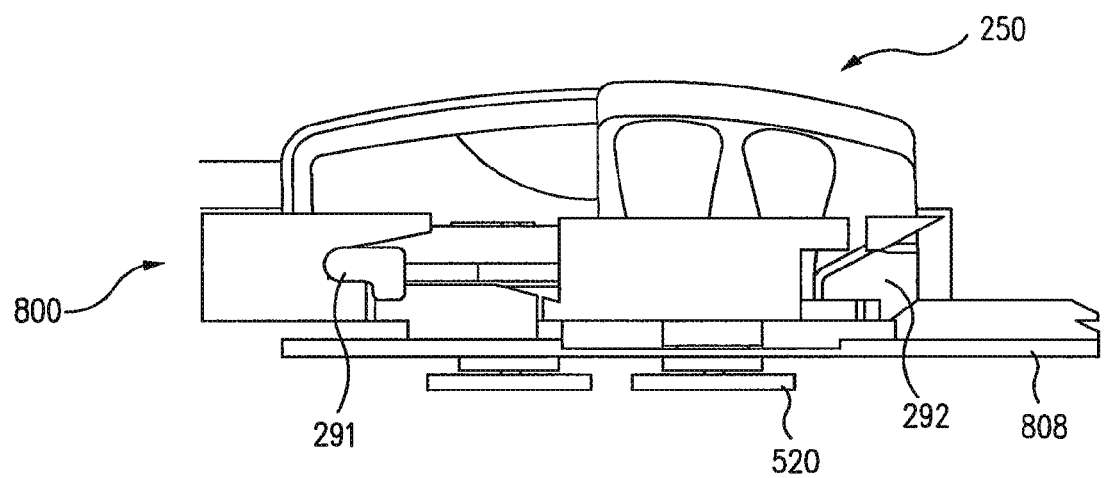
Figure 26E:
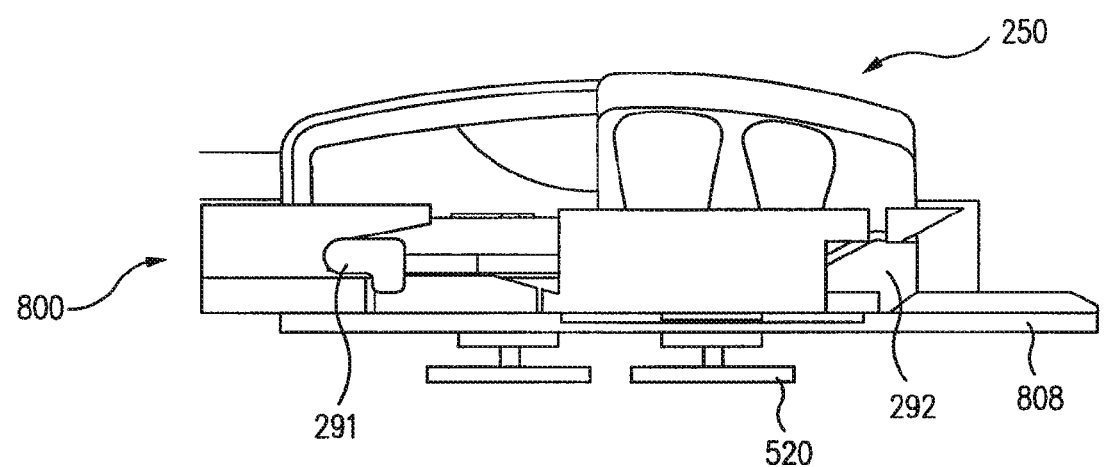

FIGS. 26A-26E illustrate an engagement sequence of an instrument 250 and the ISA 800 of this embodiment. The instrument tip 250 is first inserted into a surgical accessory, such as a cannula. Then, front tabs 291 are inserted into the ISA 800 and moved toward the front of the ISA 800 (shown by arrow A) to be eventually captured by a front wedge portion 810 of the ISA housing (FIG. 26A). Front tabs 291 push against slide plates 812 to actuate retractor plate 808 downwards away from the ISA 800 and instrument 250 to insure that the PSM inputs are not caught on the instrument inputs, and back tabs 292 are captured by a back wedge portion 820 of the ISA housing (FIG. 26B). Actuation of the retractor plate 808 moves all four PSM inputs 520 downwards away from instrument 250 (FIG. 26C). Once the front tab 291 is in place, the slide lever moves into place (FIG. 26D). Finally, both front and back tabs 291 and 292 move into recesses in the ISA housing that allow the retractor plate 808 to move back up towards the instrument 250, and the electrical contacts between the instrument and ISA are connected. It is noted that each of the plurality of drape interfaces operably couples to a respective PSM input and an instrument input although not all of the drape interfaces may have been illustrated above.

Figure 27A:
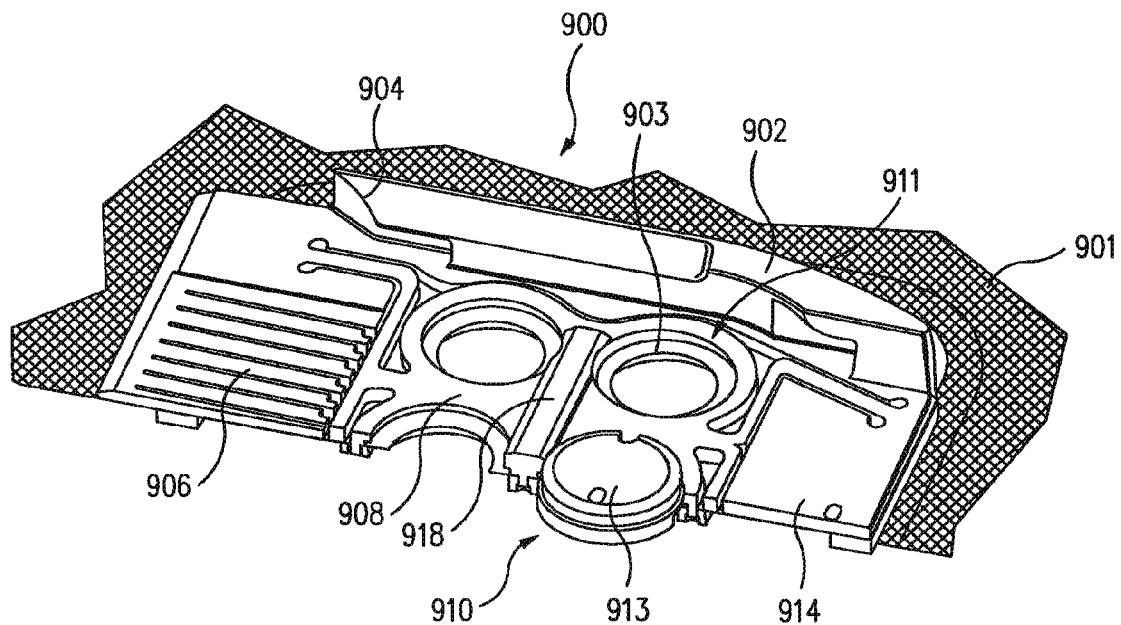
FIGS. 27A and 27B illustrate top and bottom perspective views of another ISA in accordance with an embodiment of the present invention.
Figure 27B:
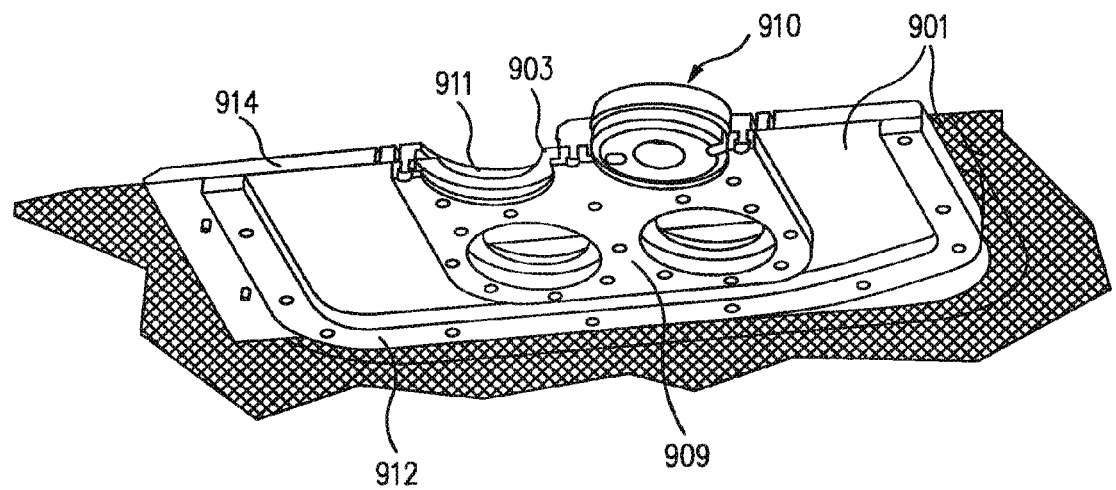

Referring now to FIGS. 27A and 27B, top and bottom sectional perspective views of another ISA known as an "X-spring" embodiment is illustrated in accordance with an embodiment of the present invention. An ISA 900 includes retaining members 902 and 904 (two other retaining members, not shown, are opposite 902 and 904), and electrical contacts 906 for engaging electrical contacts on the PSM and/or the surgical instrument. ISA 900 further includes a top retractor plate 908, a bottom retractor plate 909, drape interfaces 910 including ISA inputs 913, ISA input apertures 911, and a retainer 912 for holding a drape portion 901 in place.

Retaining members 902 and 904 are used to capture an instrument onto the ISA and in one example, four main corners are used to retain a surgical instrument. In a further example, back retaining members are wider apart than front retaining members to create a wedge effect such that the surgical instrument is guided to a retained position moving from the back toward the front of the ISA.

Drape 901 is sandwiched between layers of the ISA, in particular between ISA housing 914 and retainer 912, and between top retractor plate 908 and bottom retractor plate 909. Drape 901 includes a drape hole 903 that is aligned and concentric with ISA input aperture 911.

Figure 28A:
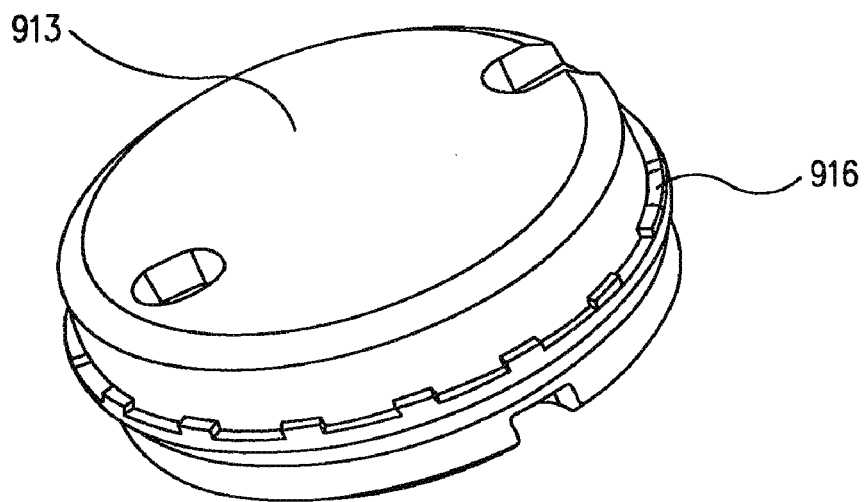
FIGS. 28A and 28B illustrate views of an ISA input in accordance with this embodiment of the present invention.
Figure 28B:
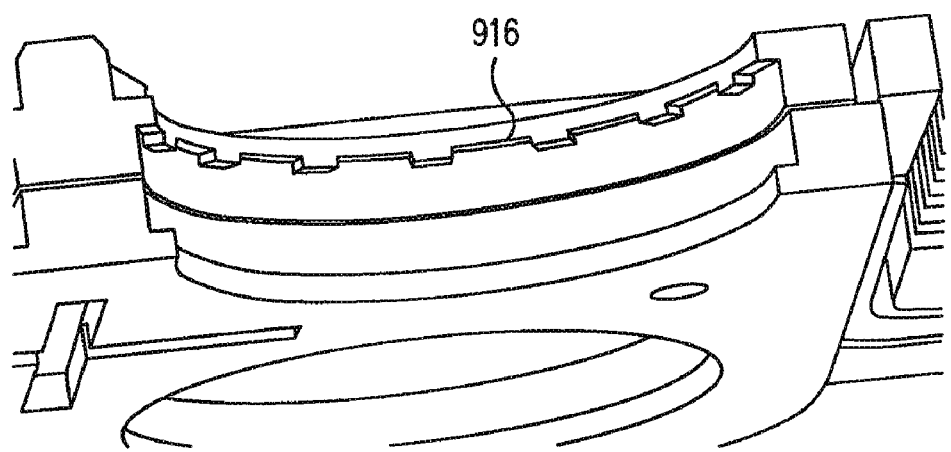

FIGS. 28A and 28B illustrate views of an ISA input of drape interface 910 in accordance with this embodiment of the present invention. Each of the inputs 913 fits within an input aperture 911 and includes mating grooves 916. Each of the inputs 913 have a wider section that is caught between the top and bottom sections of the retractor plate, 908 and 909, respectively, to be retained within the input aperture 911. Groove 916 (FIG. 28A) fits snuggly in aperture 911 and creates a tortuous path to prevent fluid from passing through the ISA and reaching the robot arm. The edges of drape hole 903 in the drape 901 is aligned with groove 916 of the input.

In one example, bottom retractor plate 909 retains drape interfaces 910, holds drape 901 in place, keeps top retractor plate 908 from moving above the housing 914 top surface, and increases the stiffness of the top retractor plate 908.

Figure 29:
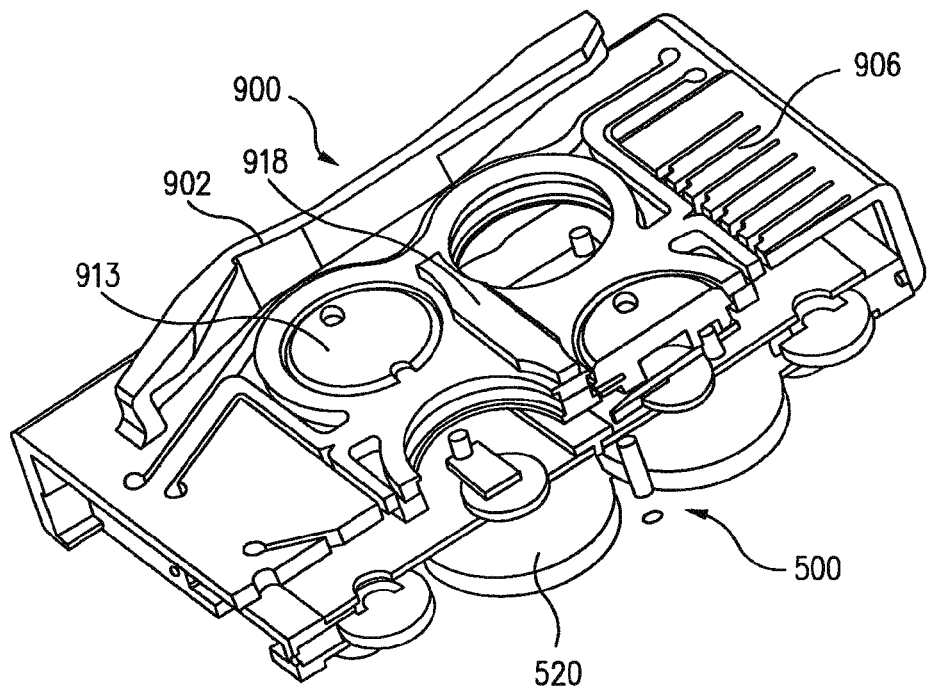
FIG. 29 illustrates a sectional view of the ISA over an adaptor receiving portion of a PSM in accordance with this embodiment of the present invention.
Figure 30:
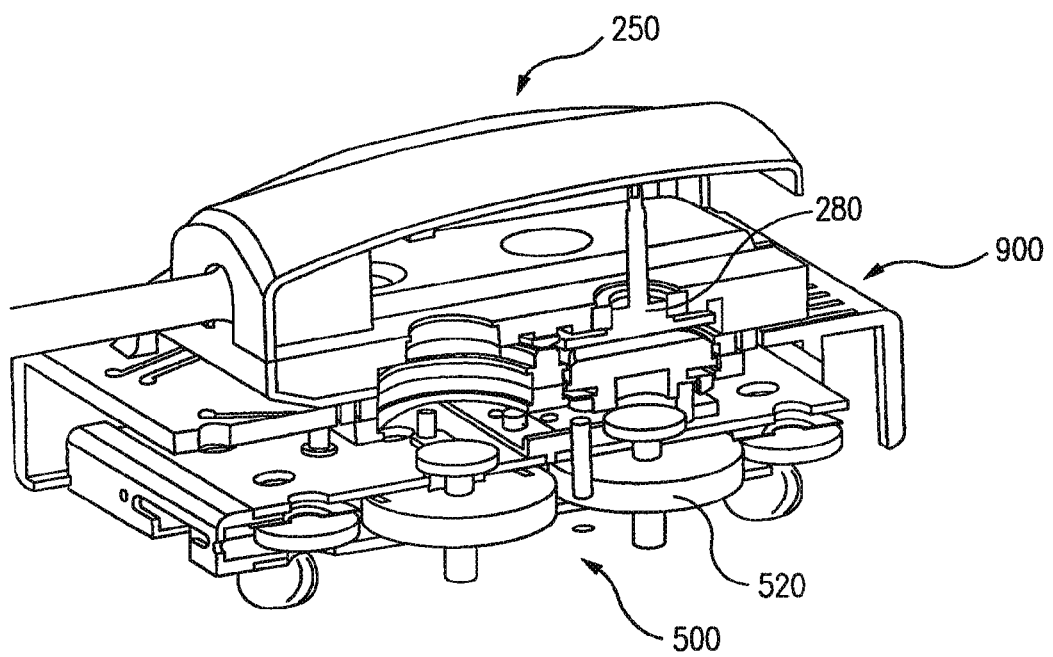
FIG. 30 illustrates a sectional view of an instrument, ISA, and adaptor receiving portion of a PSM operably coupled together in accordance with this embodiment of the present invention.

FIG. 29 illustrates a sectional view of the ISA 900 over an adaptor receiving portion 500 of a PSM (including inputs 520) in accordance with this embodiment of the present invention, and FIG. 30 illustrates a sectional view of an instrument 250 (including inputs 280) operably coupled to the assembly of FIG. 29 in accordance with this embodiment of the present invention.

Figure 31A:
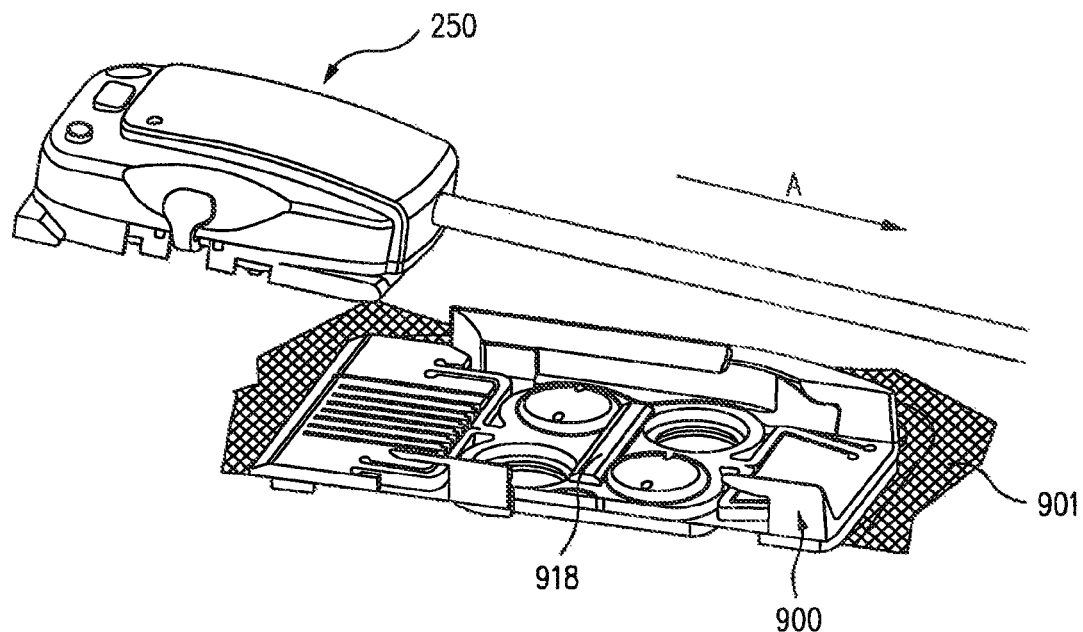
FIGS. 31A-31E illustrate an engagement sequence of an instrument and the ISA of this embodiment.
Figure 31B:
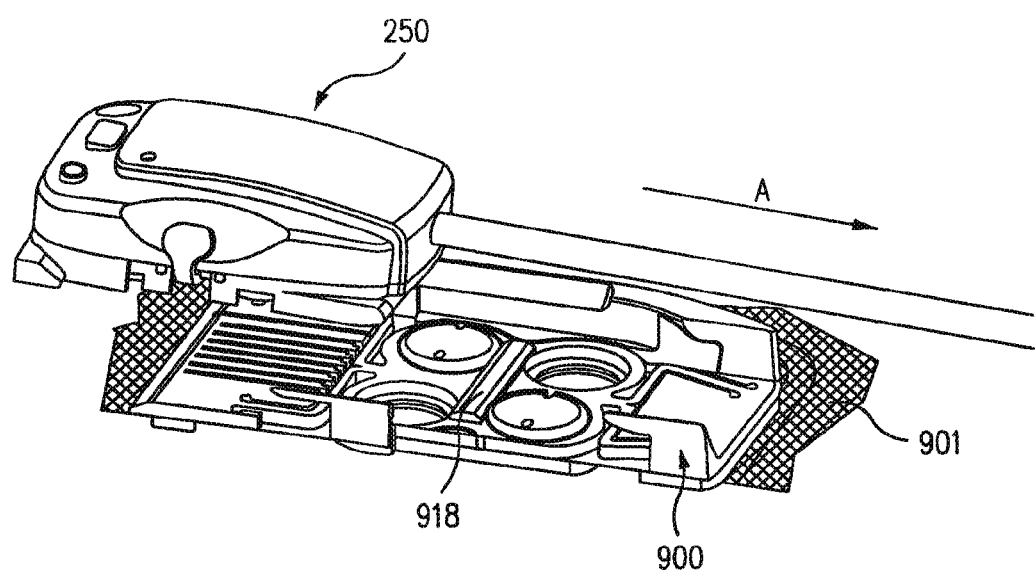
Figure 31C:
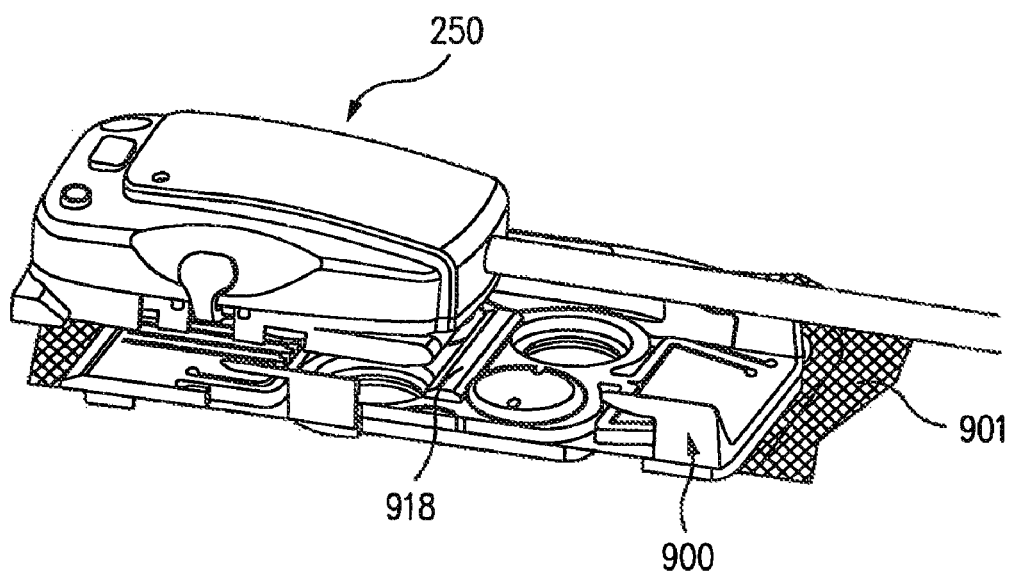
Figure 31D:
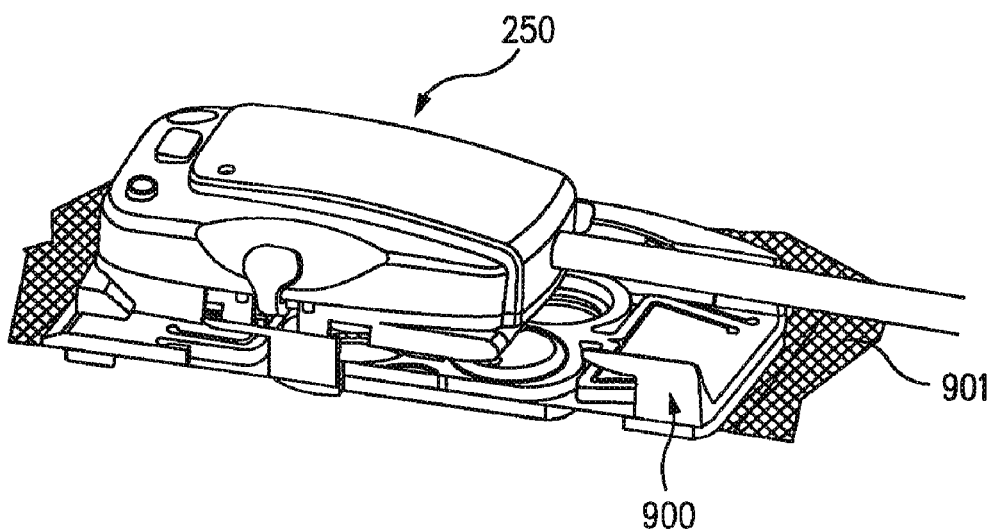
Figure 31E:
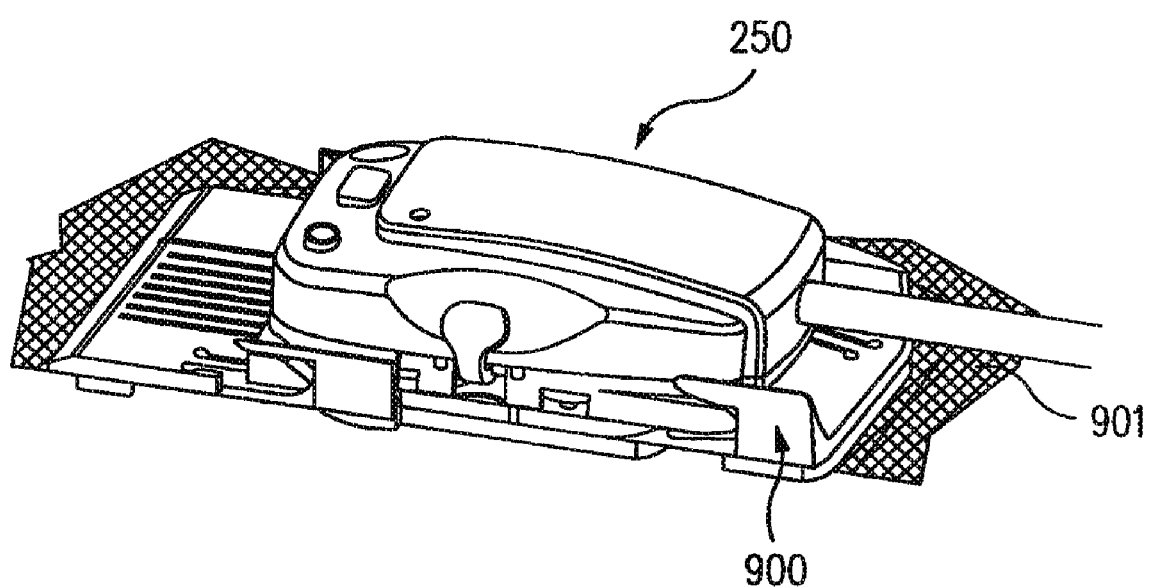

FIGS. 31A-31E illustrate an engagement sequence of an instrument 250 and the ISA 900 of this embodiment. The instrument tip 250 is first inserted into a surgical accessory, such as a cannula (not shown) and the instrument is moved toward the front of the ISA 900 from the back of the ISA 900 shown by arrow A (FIGS. 31A and 31B). As the instrument is positioned over the ISA 900, the instrument starts pushing down on a bar 918 of top retractor plate 908 to move the retractor plate and ISA inputs away from the instrument and to insure that the instrument inputs are not caught on the ISA inputs (FIGS. 31C and 31D). When the front and back tabs of the instrument are properly inserted, the center bar 918 of the top retractor plate moves up into a recess in the instrument, and the instrument inputs are over the ISA inputs, ready for engagement between the inputs (FIG. 31E). It is noted that each of the plurality of drape interfaces operably couples to a respective PSM input and an instrument input although not all of the drape interfaces may have been illustrated above.

Advantageously, the adaptors, drapes, and surgical systems of the present invention provide for improved installation and interfacing of a surgical instrument with a manipulator arm, improved robustness of the sterile field, and increased visualization of the patient by reducing the size of the drapes with more form fitting features.

Embodiments described above illustrate but do not limit the invention. It should also be understood that numerous modifications and variations are possible in accordance with the principles of the present invention. For example, the number of pins, slots, disks, and teeth may vary but must allow for operable coupling between the ISA, manipulator arm, and surgical instrument. Accordingly, the scope of the invention is defined only by the following claims.

We claim:

1. A sterile adaptor, comprising:
   a rigid exterior surface adapted to couple to a sterile surgical instrument in a sterile field;
   a rigid interior surface adapted to couple to a non-sterile manipulator arm of a robotic surgical system; and
   a drape interface including a flexible drape material positioned between a rotatable input of the surgical instrument and a rotatable input of the manipulator arm, the drape interface adapted to transmit torque from the manipulator arm rotatable input to the surgical instrument rotatable input through the flexible drape material.

2. The adaptor of claim 1, wherein the exterior surface includes retaining structures forming a wedge shape narrowing from a proximal end to a distal end.

3. The adaptor of claim 1, wherein the drape interface includes two rings with the flexible drape material therebetween.

4. The adaptor of claim 1, further comprising a plurality of drape interfaces, wherein each drape interface is adapted to receive an input of the surgical instrument and an input of the manipulator arm.

5. The adaptor of claim 4, further comprising a retractor plate including the plurality of drape interfaces.

6. The adaptor of claim 5, wherein the retractor plate includes a top plate and a bottom plate with the flexible drape material therebetween.

7. The adaptor of claim 1, further comprising an electrical contact adapted to pass electrical signals between the manipulator arm and the surgical instrument.

8. A sterile adaptor, comprising:
- a rigid exterior surface adapted to couple to a sterile surgical instrument in a sterile field;
- a rigid interior surface adapted to couple to a non-sterile manipulator arm of a robotic surgical system; and
- a drape interface including a flexible drape material positionable between a rotatable input of the surgical instrument and a rotatable input of the manipulator arm, the drape interface adapted to transmit torque from the manipulator arm rotatable input to the surgical instrument rotatable input through the flexible drape material, wherein the drape interface includes a rotating disk with an indent for receiving the input of the surgical instrument.

9. A sterile drape to cover a non-sterile portion of a robotic surgical system, the sterile drape comprising:
- a flexible exterior surface adapted to be positioned adjacent to a sterile field for performing a surgical procedure;
- a flexible interior surface adapted to receive a non-sterile manipulator arm of the robotic surgical system; and
- a sterile adaptor including:
  - a rigid exterior surface adapted to couple to a sterile surgical instrument in the sterile field;
  - a rigid interior surface adapted to couple to the non-sterile manipulator arm; and
  - a drape interface having a flexible drape material positioned between a rotatable input of the surgical instrument and a rotatable input of the manipulator arm, the drape interface adapted to transmit torque from the manipulator arm rotatable input to the surgical instrument rotatable input through the flexible drape material.

10. The sterile drape of claim 9, wherein the drape is comprised of a material selected from the group consisting of polyethylene, polyurethane, polycarbonate, and similar elastic durable materials.

11. The sterile drape of claim 9, wherein the flexible exterior surface and the flexible interior surface are coupled to a larger drape.

12. The sterile drape of claim 9, wherein the drape interface includes two attached rings to retain a drape section therebetween.

13. The sterile drape of claim 9, wherein the sterile adaptor further includes a plurality of drape interfaces, with each drape interface adapted to receive an input of the surgical instrument and an input of the manipulator arm.

14. The sterile drape of claim 9, wherein the sterile adaptor includes an electrical contact adapted to interface between an electrical contact on the manipulator arm and an electrical contact on the surgical instrument.

15. A sterile drape to cover a non-sterile portion of a robotic surgical system, the sterile drape comprising:
- a flexible exterior surface adapted to be positioned adjacent to a sterile field for performing a surgical procedure;
- a flexible interior surface adapted to receive a non-sterile manipulator arm of the robotic surgical system; and
- a sterile adaptor including:
  - a rigid exterior surface adapted to couple to a sterile surgical instrument in the sterile field;
  - a rigid interior surface adapted to couple to the non-sterile manipulator arm; and
  - a drape interface having a flexible drape material positionable between a rotatable input of the surgical instrument and a rotatable input of the manipulator arm, the drape interface adapted to transmit torque from the manipulator arm rotatable input to the surgical instrument rotatable input through the flexible drape material, wherein the drape interface includes a rotating disk with an indent for receiving an input of the surgical instrument.

16. A robotic surgical system for performing a procedure within a sterile field, the system comprising:
- a manipulator arm in a non-sterile field;
- a surgical instrument in the sterile field; and
- a sterile drape over the manipulator arm to shield the manipulator arm from the sterile field, the sterile drape including a sterile adaptor having:
  - a rigid exterior surface coupled to the surgical instrument in the sterile field;
  - a rigid interior surface coupled to the manipulator arm in the non-sterile field; and
  - a drape interface having a flexible drape material positioned between a rotatable input of the surgical instrument and a rotatable input of the manipulator arm, the drape interface adapted to transmit torque from the manipulator arm rotatable input to the surgical instrument rotatable input through the flexible drape material.

17. The system of claim 16, wherein the surgical instrument is selected from the group consisting of articulated tools with end effectors, such as jaws, scissors, graspers, needle holders, micro-dissectors, staple appliers, tackers, suction irrigation tools, and clip appliers, and non-articulated tools, such as cutting blades, cautery probes, irrigators, catheters, and suction orifices.

18. The system of claim 16, wherein the drape interface includes a rotating disk with an indent for receiving an input of the surgical instrument.

19. The system of claim 16, wherein the drape interface includes two attached rings to retain a drape section therebetween.

20. The system of claim 16, wherein the sterile adaptor further includes a plurality of drape interfaces, with each drape interface adapted to receive an input of the surgical instrument and an input of the manipulator arm.

* * * * *